(12) United States Patent
Doty

(10) Patent No.: US 8,277,505 B1
(45) Date of Patent: Oct. 2, 2012

(54) DEVICES FOR PROVIDING UP TO SIX-DEGREES OF MOTION HAVING KINEMATICALLY-LINKED COMPONENTS AND METHODS OF USE

(76) Inventor: Keith L. Doty, Gainesville, FL (US)

( * ) Notice: Subject to any disclaimer, the term of this patent is extended or adjusted under 35 U.S.C. 154(b) by 0 days.

(21) Appl. No.: 13/157,539

(22) Filed: Jun. 10, 2011

(51) Int. Cl.
 *A61F 2/44* (2006.01)
(52) U.S. Cl. .................................. 623/17.11; 623/17.14
(58) Field of Classification Search ..... 623/17.11–17.16
 See application file for complete search history.

(56) References Cited

U.S. PATENT DOCUMENTS

| | | | |
|---|---|---|---|
| 4,309,777 A | 1/1982 | Patil | |
| 4,349,921 A | 9/1982 | Kuntz | |
| 4,595,663 A | 6/1986 | Krohn et al. | |
| 4,714,469 A | 12/1987 | Kenna | |
| 4,759,766 A | 7/1988 | Buettner-Janz et al. | |
| 4,759,769 A | 7/1988 | Hedman et al. | |
| 4,846,840 A | 7/1989 | Leclercq et al. | |
| 4,863,476 A | 9/1989 | Shepperd | |
| 4,932,975 A | 6/1990 | Main et al. | |
| 4,936,848 A | 6/1990 | Bagby | |
| 4,946,378 A | 8/1990 | Hirayama et al. | |
| 4,961,740 A | 10/1990 | Ray et al. | |
| 4,997,432 A | 3/1991 | Keller | |
| 5,002,576 A | 3/1991 | Furhmann et al. | |
| 5,024,670 A | 6/1991 | Smith et al. | |
| 5,037,438 A | 8/1991 | Davidson | |
| 5,047,055 A | 9/1991 | Bao et al. | |
| 5,071,437 A | 12/1991 | Steffee | |
| 5,080,675 A | 1/1992 | Lawes et al. | |
| 5,258,031 A | 11/1993 | Salib et al. | |
| 5,258,043 A | 11/1993 | Stone | |
| 5,306,307 A | 4/1994 | Senter et al. | |
| 5,306,308 A | 4/1994 | Gross et al. | |
| 5,306,309 A | 4/1994 | Wagner et al. | |
| 5,308,412 A | 5/1994 | Shetty et al. | |

(Continued)

FOREIGN PATENT DOCUMENTS

WO WO-94/04100 A1 3/1994

(Continued)

OTHER PUBLICATIONS

Bao, Q.-B. et al., "Artificial disc technology," *Neurosurgical Focus*, American Association of Neurological Surgeons, Oct. 2000, pp. 1-7, vol. 9, No. 4.

(Continued)

*Primary Examiner* — Eduardo C Robert
*Assistant Examiner* — Jacqueline Johanas
(74) *Attorney, Agent, or Firm* — Saliwanchik, LLoyd & Eisenschenk

(57) ABSTRACT

The subject invention provides a modular six-degrees-of-freedom spatial mechanism for spinal disc prosthesis, with up to three independent rotational and up to three independent translational degrees-of-freedom. The prosthesis can maintain non-separable, and non-restrictive, mechanical linkage by establishing a linked series, or chain, of kinematic pairs (joints) between components. In embodiment, a superior plate links to a planar pair (two independent degrees of translational freedom), which links to spherical pair (three independent degrees of rotational freedom), which links to a prismatic pair (one independent degree of translational freedom), which links to an inferior plate, completing the jointed kinematic chain. The kinematic pairs can be lower (surface contact) or higher (point, line, and/or curve contact) order pairs, or combinations. The subject invention can enforce the kinematic constraints to realize the kinematic pairs and can also limit the range of operation of the degrees of freedom for each pair.

42 Claims, 22 Drawing Sheets

U.S. PATENT DOCUMENTS

| | | |
|---|---|---|
| 5,314,477 A | 5/1994 | Marnay |
| 5,314,478 A | 5/1994 | Oka et al. |
| 5,320,644 A | 6/1994 | Baumgartner |
| 5,401,269 A | 3/1995 | Büttner-Janz et al. |
| 5,415,704 A | 5/1995 | Davidson |
| 5,425,773 A | 6/1995 | Boyd et al. |
| 5,458,642 A | 10/1995 | Beer et al. |
| 5,674,296 A | 10/1997 | Bryan et al. |
| 5,676,701 A | 10/1997 | Yuan et al. |
| 5,782,832 A | 7/1998 | Larsen et al. |
| 5,827,328 A | 10/1998 | Buttermann |
| 5,865,846 A | 2/1999 | Bryan et al. |
| 6,001,130 A | 12/1999 | Bryan et al. |
| 6,019,792 A | 2/2000 | Cauthen |
| 6,156,067 A | 12/2000 | Bryan et al. |
| 6,179,874 B1 | 1/2001 | Cauthen |
| 6,315,797 B1 | 11/2001 | Middleton |
| 6,368,350 B1 | 4/2002 | Erickson et al. |
| 6,395,032 B1 | 5/2002 | Gauchet |
| 6,419,706 B1 | 7/2002 | Graf |
| 6,626,943 B2 | 9/2003 | Eberlein et al. |
| 6,645,248 B2 | 11/2003 | Casutt |
| 6,656,224 B2 | 12/2003 | Middleton |
| 6,669,732 B2 | 12/2003 | Serhan et al. |
| 6,682,562 B2 | 1/2004 | Viart et al. |
| 6,726,721 B2 | 4/2004 | Stoy et al. |
| 6,733,532 B1 | 5/2004 | Gauchet et al. |
| 6,736,850 B2 | 5/2004 | Davis |
| 6,740,118 B2 | 5/2004 | Eisermann et al. |
| 6,749,635 B1 | 6/2004 | Bryan |
| 6,770,095 B2 | 8/2004 | Grinberg et al. |
| 6,802,867 B2 | 10/2004 | Manasas et al. |
| 6,827,740 B1 | 12/2004 | Michelson |
| 6,833,006 B2 | 12/2004 | Foley et al. |
| 6,960,232 B2 | 11/2005 | Lyons et al. |
| 6,964,686 B2 | 11/2005 | Gordon |
| 6,966,929 B2 | 11/2005 | Mitchell |
| 6,981,989 B1 | 1/2006 | Fleischmann et al. |
| 6,989,032 B2 | 1/2006 | Errico et al. |
| 6,994,727 B2 | 2/2006 | Khandkar et al. |
| 7,001,433 B2 | 2/2006 | Songer et al. |
| 7,011,685 B2 | 3/2006 | Arnin et al. |
| 7,014,658 B2 | 3/2006 | Ralph et al. |
| 7,022,138 B2 | 4/2006 | Mashburn |
| 7,022,139 B2 | 4/2006 | Errico et al. |
| 7,044,969 B2 | 5/2006 | Errico et al. |
| 7,048,763 B2 | 5/2006 | Ralph et al. |
| 7,060,100 B2 | 6/2006 | Ferree et al. |
| 7,066,960 B1 | 6/2006 | Dickman |
| 7,101,400 B2 | 9/2006 | Thramann et al. |
| 7,122,055 B2 | 10/2006 | Ralph et al. |
| 7,156,876 B2 | 1/2007 | Moumene et al. |
| 7,163,559 B2 | 1/2007 | Errico et al. |
| 7,186,268 B2 | 3/2007 | Errico et al. |
| 7,195,644 B2 | 3/2007 | Diaz et al. |
| 7,198,643 B2 | 4/2007 | Zubok et al. |
| 7,208,014 B2 | 4/2007 | Ralph et al. |
| 7,214,244 B2 | 5/2007 | Zubok et al. |
| 7,223,290 B2 | 5/2007 | Errico et al. |
| 7,258,699 B2 | 8/2007 | Errico et al. |
| 7,261,739 B2 | 8/2007 | Ralph et al. |
| 7,270,680 B2 | 9/2007 | Ralph et al. |
| 7,270,681 B2 | 9/2007 | Cauthen |
| 7,273,496 B2 | 9/2007 | Mitchell |
| 7,276,082 B2 | 10/2007 | Zdeblick et al. |
| 7,291,171 B2 | 11/2007 | Ferree |
| 7,314,487 B2 | 1/2008 | Ralph et al. |
| 7,316,714 B2 | 1/2008 | Gordon et al. |
| 7,331,994 B2 | 2/2008 | Gordon et al. |
| 7,331,995 B2 | 2/2008 | Eisermann et al. |
| 7,338,525 B2 | 3/2008 | Ferree |
| 7,361,192 B2 | 4/2008 | Doty |
| 7,442,211 B2 | 10/2008 | de Villiers et al. |
| 7,531,001 B2 | 5/2009 | de Villiers et al. |
| 7,582,115 B2 | 9/2009 | Weber |
| 7,695,516 B2 | 4/2010 | Zeegers |
| 7,713,302 B2 | 5/2010 | Ralph et al. |
| 7,731,754 B2 | 6/2010 | de Villiers et al. |
| 7,799,080 B2 | 9/2010 | Doty |
| 2002/0111681 A1 | 8/2002 | Ralph et al. |
| 2003/0014110 A1 | 1/2003 | Ralph et al. |
| 2003/0014112 A1 | 1/2003 | Ralph et al. |
| 2004/0167626 A1 | 8/2004 | Geremakis et al. |
| 2004/0260396 A1 | 12/2004 | Ferree et al. |
| 2005/0015152 A1 | 1/2005 | Sweeney |
| 2005/0192670 A1 | 9/2005 | Zubok et al. |
| 2005/0234555 A1 | 10/2005 | Sutton et al. |
| 2005/0240270 A1 | 10/2005 | Zubok et al. |
| 2005/0273169 A1 | 12/2005 | Purcell |
| 2006/0036324 A1 | 2/2006 | Sachs et al. |
| 2006/0136062 A1 | 6/2006 | DiNello et al. |
| 2006/0235525 A1 | 10/2006 | Gil et al. |
| 2006/0235529 A1 | 10/2006 | Ralph et al. |
| 2007/0150062 A1 | 6/2007 | Zubok et al. |
| 2008/0015699 A1 | 1/2008 | Voydeville |
| 2008/0021557 A1 | 1/2008 | Trieu |
| 2008/0027547 A1 | 1/2008 | Yu et al. |
| 2008/0058940 A1 | 3/2008 | Wu et al. |
| 2008/0065211 A1 | 3/2008 | Albert et al. |
| 2008/0077242 A1 | 3/2008 | Reo et al. |
| 2008/0077244 A1 | 3/2008 | Robinson |
| 2008/0077246 A1 | 3/2008 | Fehling et al. |
| 2010/0070033 A1 | 3/2010 | Doty |
| 2010/0076558 A1 | 3/2010 | de Villiers et al. |
| 2010/0324688 A1 | 12/2010 | Doty |

FOREIGN PATENT DOCUMENTS

| | | |
|---|---|---|
| WO | WO-2004/054477 A1 | 7/2004 |
| WO | WO-2007/076194 A2 | 7/2007 |
| WO | WO-2010/147795 A2 | 12/2010 |

OTHER PUBLICATIONS

Bao, Q-B. et al., "The artificial disc: theory, design and materials," *Biomaterials*, 1996, pp. 1157-1167, vol. 17, No. 12.

Bogduk, N. et al., "Biomechanics of the cervical spine. I: Normal kinematics," *Clinical Biomechanics*, 2000, pp. 633-648, vol. 15.

Bogduk, N. et al., "A biological basis for instantaneous centres of rotation of the vertebral column," *Proceedings of the Institution of Mechanical Engineers*, 1995, pp. 177-183, vol. 209.

Van Mameren, H. et al., "Cervical Spine Motion in the Sagittal Plane II: Position of Segmental Averaged Instantaneous Centers of Rotation—A Cineradiographic Study," *Spine*, 1992, pp. 467-474, vol. 17, No. 5.

Panjabi, M.M. "Instantaneous Center of Rotation and Instability of the Cervical Spine: A Clinical Study," *Spine*, Mar. 1997, pp. 647-648, vol. 22, No. 6.

Panjabi, M.M. et al., "Articular Facets of the Human Spine: Quantitative Three-Dimensional Anatomy," *Spine*, 1993, pp. 1298-1310, vol. 18, No. 10.

Yoganandan, N. et al., "Chapter 5—Biomechanics of the Cervical Spine," *Principles of Spinal Surgery*, McGraw-Hill, 1996, pp. 69-83.

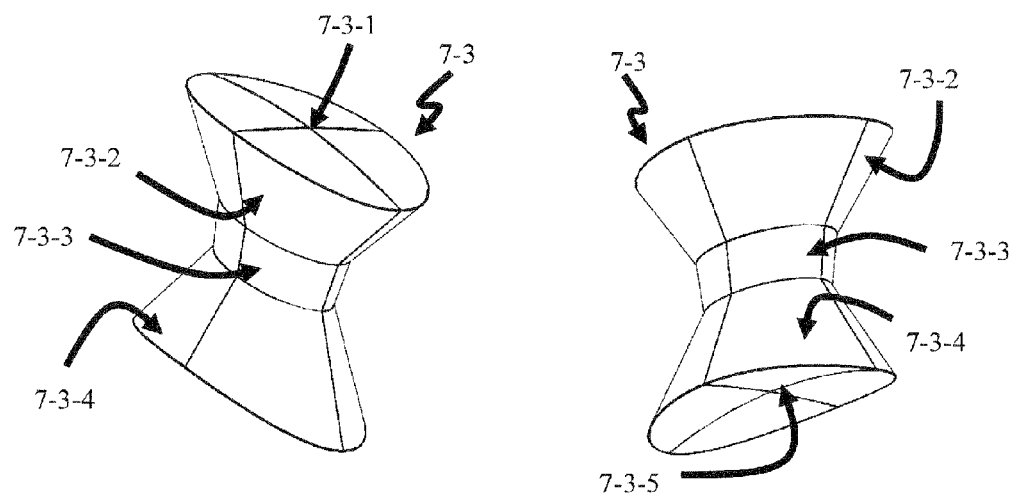
FIG. 17A  FIG. 17B
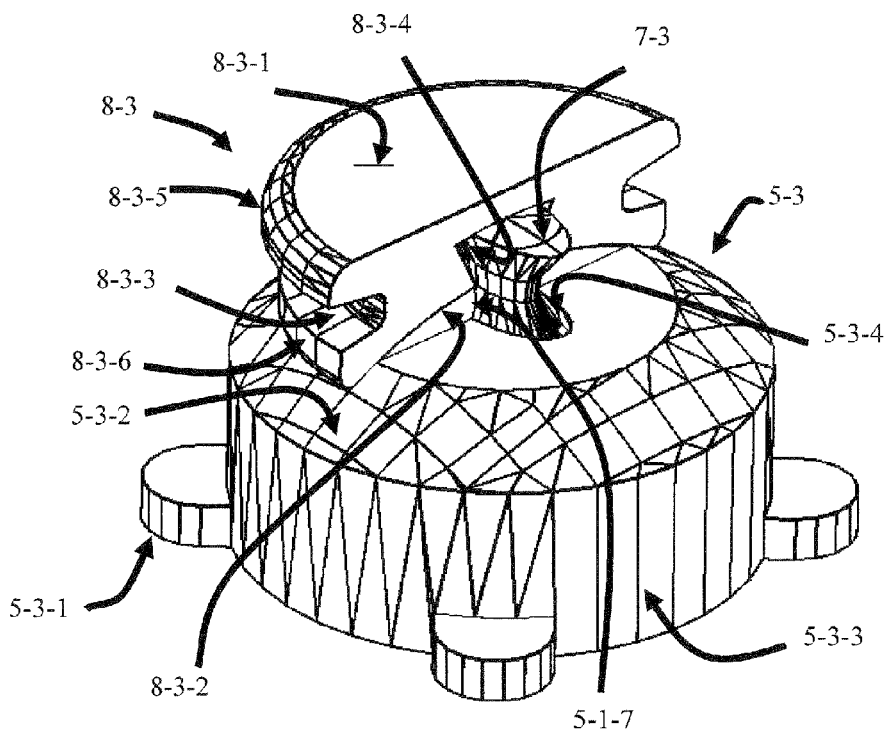
FIG. 18

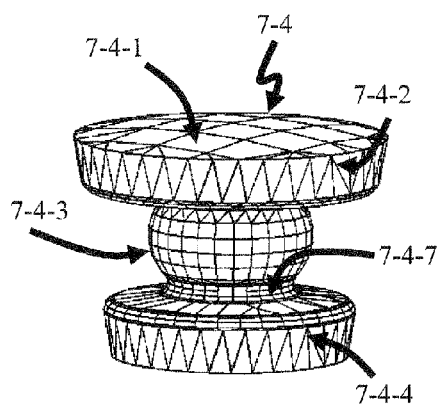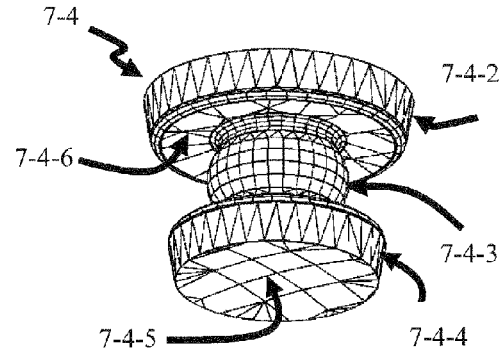
FIG. 19A    FIG. 19B
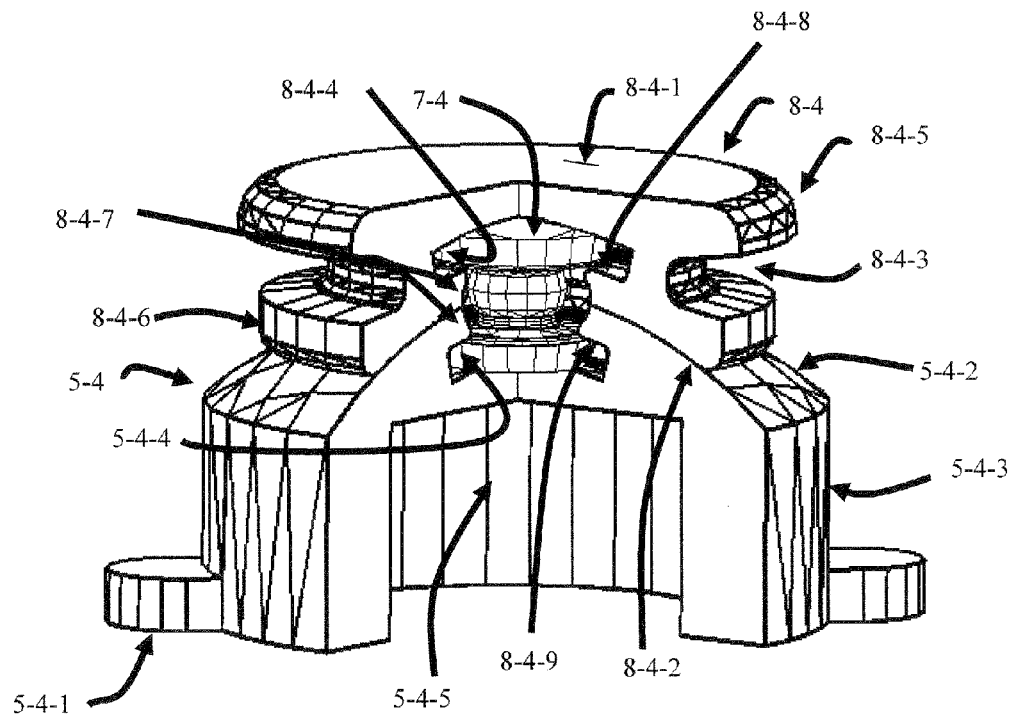
FIG. 20

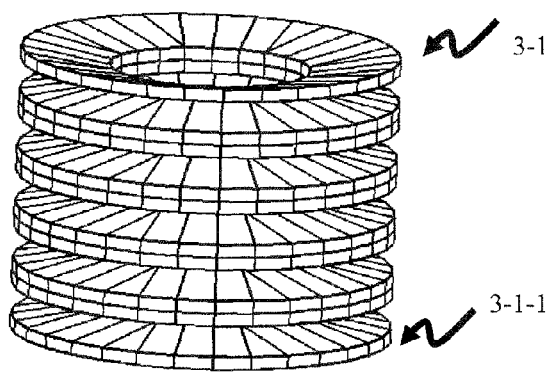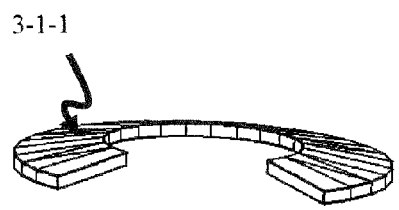
FIG. 32A  FIG. 32B
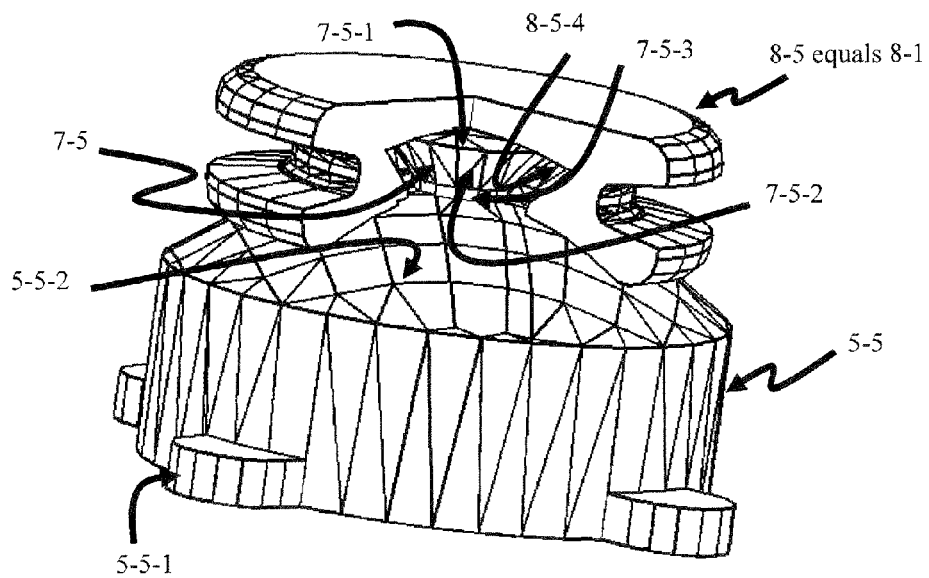
FIG. 33

DEVICES FOR PROVIDING UP TO SIX-DEGREES OF MOTION HAVING KINEMATICALLY-LINKED COMPONENTS AND METHODS OF USE

BACKGROUND OF INVENTION

Spinal disc herniation, a common ailment, often induces pain, as well as neurologically and physiologically debilitating processes for which relief becomes paramount. If conservative treatments fail, the more drastic measures of discectomies and spinal fusion may be indicated. The latter treatment, while providing short term relief, limits spinal mobility and often leads to excessive forces on facet joints adjacent to the fusion and may create further problems over time. Drastic treatments are usually unable to restore normal disc function. The loss of disc function has led to a number of disc prosthesis that attempt to provide natural motion.

The literature documents that the Instantaneous Axis of Rotation (IAR) during sagittal rotation of the superior vertebra with respect to the inferior vertebra of a Functional Spinal Unit (FSU) in the cervical spine moves significant distances during flexion and extension of the spine (Mameren H. van, Sanches H., Beursgens J., Drukker, J., "Cervical Spine Motion in the Sagittal Plane II: Position of Segmental Averaged Instantaneous Centers of Rotation—A Cineradiographic Study", *Spine* 1992, Vol. 17, No. 5, pp. 467-474). This motion varies widely between functional spinal units on an individual spine and between individuals and can depend on age, time-of-day, and the general health and condition of the intervertebral discs, facet joints and other components of the FSU and spine. A moving IAR means that the superior vertebra can both rotate and translate while moving with respect to the inferior vertebra of an FSU. Natural spinal motions place severe requirements on the design of a prosthetic disc; simple rotational joints are not able meet those requirements.

In addition, motion coupling between axial and lateral bending and other functional spinal units involved in the overall spinal motion increases the complexity and difficulty in developing a prosthetic disc replacement that realizes natural spinal motion. The complex facet surfaces in an FSU significantly influence and constrain sagittal, lateral and axial motions. The orientation of these facet surfaces vary with FSU location in the spine and induce wide variations in motion parameters and constraints. The complex motion of a superior vertebra with respect to the associated inferior vertebra of an FSU, certainly in the cervical spine, cannot be realized by a simple rotation or simple translation, or even a combination of rotation and translation along a fixed axis, and still maintain the integrity and stability of the FSU and facet joints.

Researchers have attempted to design a successful intervertebral disc for years. Salib et al., U.S. Pat. No. 5,258,031; Marnay, U.S. Pat. No. 5,314,477; Boyd et al., U.S. Pat. No. 5,425,773; Yuan et al., U.S. Pat. No. 5,676,701; and Larsen et al., U.S. Pat. No. 5,782,832 all use ball-and-socket arrangements fixed to the superior and inferior plates rigidly attached to the vertebrae of an FSU. However, these designs limit motion to rotation only about the socket when the two plates are in contact. As the literature points out (Bogduk N. and Mercer S., "Biomechanics of the cervical spine. I: Normal kinematics", *Clinical Biomechanics*, Elsevier, 15 (2000) 633-648; and Mameren H. van, Sanches H., Beursgens J., Drukker, J., "Cervical Spine Motion in the Sagittal Plane II: Position of Segmental Averaged Instantaneous Centers of Rotation—A Cineradiographic Study", Spine 1992, Vol. 17, No. 5, pp. 467-474), this restricted motion does not correspond to the natural motion of the vertebrae, either for sagittal plane motion or for combined sagittal, lateral and axial motion. Further, when the two plates, as described in the cited patents, are not in contact, the devices are unable to provide stability to the intervertebral interface, which can allow free motion and lead to disc related spondylolisthesis, FSU instability and excessive facet loading.

As a further elaboration on the many ball-and-socket configurations, consider Salib et. al. (U.S. Pat. No. 5,258,031) as an example of previous efforts to address this problem. The Salib et al. ball-and-socket arrangement only provides 3 independent axes of rotation and no translation when engaged.

During complex motions of an FSU, the superior vertebra, in general, requires translation along three independent directions. A sliding ovate structure in an oversized socket cannot perform such general translation motions, either, as it must engage in a trajectory dictated by its socket's geometrical surface and does not change the deleterious effects that may occur on the facet joints of the unit.

Currently known devices appear to have similar motion and instability limitations, such as the rocker arm device disclosed by Cauthen (U.S. Pat. Nos. 6,019,792; 6,179,874; 7,270,681), the freely moving sliding disc cores found in the Bryan et al. patents (U.S. Pat. Nos. 5,674,296; 5,865,846; 6,001,130; and 6,156,067) and the SB Charité™ prosthesis, as described by Búttner-Jantz K., Hochschuler S. H., McAfee P. C. (Eds), *The Artificial Disc*, ISBN 3-540-41779-6 Springer-Verlag, Berlin Heidelberg New York, 2003; and U.S. Pat. No. 5,401,269; and Buettner-Jantz et al. U.S. Pat. No. 4,759,766). In addition, the sliding disc core devices of the Bryan et al. and SB Charité™ devices do not permit natural motion of the joint for any fixed shape of the core.

With the above described prosthetic devices, when the FSU extends, the prosthesis's sliding core, in some cases, generates unnatural constraining forces on the FSU by restricting closure of the posterior intervertebral gap in the FSU. Further, the core does not mechanically link the upper and lower plates of the prosthesis and is unable to accommodate the changing intervertebral gap throughout the range of motion. Such conditions can contribute to prosthetic disc spondylolisthesis and/or transmission of large forces through the prosthesis not normally experienced with nominal loads. In general, unconstrained or over-constrained relative motion between the two vertebral plates in a prosthetic disc can contribute to FSU instability over time.

Various means of incorporating uniform, predictable, but kinematically restricted, relative lateral translation motion between vertebral plates without joint separation has been instructed, for example, by Zeegers in U.S. Pat. No. 7,695, 516. Uniform, predictable two dimensional, but kinematically restricted, relative translational motion along a frontal axis from anterior to posterior and an orthogonal sagittal axis from left lateral to right lateral without joint separation has been instructed by Doty (U.S. Pat. Nos. 7,361,192, 7,799, 080, and 7,927,375, as well as U.S. Patent application no. US2010/0324688A1 and Published PCT Application No, PCT/US2010/37721). Vertical translations relate closely with static and dynamic load handling prostheses and will be discussed next.

Current prosthetic disc technology appears to be limited in static and dynamic load handling capability. For example, load bearing and shock absorption in the SB Charité™ design and others (e.g. Bryan et al., U.S. Pat. No. 5,865,846) rely on the mechanical properties of the resilient, ultra-high-molecular-weight polyethylene core to provide both strength and static and dynamic loading. The rigidity of the sliding core appears to offer little energy absorption and flexibility to meet the changing intervertebral gap requirements during motion, and may likely generate excessive reaction forces on the spine during flexion, forces that can potentially produce extra stress on facet joints and effect mobility.

More recent attempts to provide dynamic and static loading capability is taught in the series of patents by Ralph et al. (U.S. Pat. Nos. 6,645,249, 6,863,688, 6,863,688, 7,014,658, 7,048,763, 7,122,055, 7,208,014, 7,261,739, 7,270,680, 7,314,487, and 7,713,302) wherein the force restoring mechanism begins with a multi-pronged domed spring between two plates followed by a wave-washer then ending with a spiral grooved Belleville spring as the force restoring element. The multi-pronged domed spring employs a ball-and-socket arrangement on the upper plate and allows relative rotations between the spring-lower plate and the upper plate. This arrangement, during nominal FSU operation, places moments of force on the spring that tend to distort the spring and place high stresses on the set screws holding the spring down. The effects of force moments on the prongs and the dome spring is mitigated by later designs where various modifications of the spring element, as for example the spiral Belleville washer in U.S. Pat. No. 7,270,680, provides the spring more resilience to moments of force. As taught in these patents, the motion of the upper plate is limited to compression and rotation. Lateral and sagittal translations are not accommodated and so general motion in the FSU is not enabled by the device.

The work of Errico et al. (U.S. Pat. Nos. 6,989,032, 7,022,139, 7,044,969, 7,163,559, 7,186,268, 7,223,290, and 7,258,699) elaborates on the mechanical design of the patents of Ralph et al. A specially designed Belleville type washer provides a restoring force to compressions. Rotations of the superior plate of the device in a fixed ball-and-socket arrangement transfers moments of force about the washer central axis to a rigid structure. It is notable that the instruction in these designs specifically proscribes lateral motions (sagittal and lateral translation). Errico et al. employ a taper attached to the ball to limit rotation angles. De Villiers (U.S. Pat. No. 7,442,211) also instructs how to control rotation angle limits using joint stops on an ovate core. Both Errico and de Villiers rotational joint stop elements differ from the multi-spherical-surfaced sliding and multi-spherical-surfaced fixed joint stop elements instructed here in several significant respects. First, the rotational joint stops, as described in this invention, couple the rotating joint elements together so that at least one pair of the multiple rotating surfaces of the joint and joint stop elements must fully engage without separation during relative rotation, second they maintain surface contact with the rotating surface at all joint angles, and, thirdly, the sliding spherical joint stop not only supports the first two properties but maximizes the range of motion while reducing the joint stops' cavity sizes, relative to the cavity sizes of fixed joint stops, for a specified range of rotation angles.

Another approach to incorporate dynamic and static force response is taught by Gauchet (U.S. Pat. Nos. 6,395,032, 6,527,804, 6,579,320, 6,582,466, 6,582,468, and 6,733,532) wherein a hydraulic system provides shock absorption by means of a cushion between two plates contained within sealed flexible titanium bellows. Gauchet suggests the bellows can be designed to accommodate lateral forces and axial rotation that is permitted by the cushion, which, to allow sliding motion, is not attached to at least one plate. The titanium bellows can accommodate some axial rotations, but do not seem suitable for other rotations, which can cause excessive stresses on the bellows. A cushion internal to the cylinder, being flexible and not attached to at least one plate, can accommodate any rotation (U.S. Pat. Nos. 6,582,466 and 6,733,532).

Fleishman et al. in U.S. Pat. Nos. 6,375,682 and 6,981,989 utilize hydraulic action coupled with a flexible bellows to mitigate sudden forces. The bellows concept is similar to that of Gauchet.

Eberlein et al. (U.S. Pat. No. 6,626,943) utilizes a fiber ring to enclose a flexible element. The forces and moments of force are absorbed by the ring and the flexible element. The device taught in this invention uses a boot in much the same manner as Eberlein's fiber ring. Other inventions teach this concept as well, namely, Casutt in U.S. Pat. No. 6,645,248. Diaz et al. (U.S. Pat. No. 7,195,644) also uses a membrane and enclosed cushioning material in their ball and dual socket joint design. Diaz also instructs that discontinuous segments of a connecting elastomer membrane around the periphery of a prosthesis can act as a plurality of elastic bands. In this regard, the instruction herein proposes two types of membrane used in conjunction: specifically, a continuous, enveloping, highly elastic, thin inner membrane for fluid/gas separation between the internal structure of the device and elements exterior to the device overlaying tough, thick, separate, ligament-like membranes attached to at least one, and up to four, quadrants of the device. These features can be constructed into a single boot as instructed here.

Middleton suggests a variety of machined springs as the central component of a disc prosthesis in U.S. Pat. Nos. 6,136,031, 6,296,664, 6,315,797, and 6,656,224. The spring is notched to allow static and dynamic response primarily in the axial direction of the spring. But, lateral and sagittal translations and general rotations appear to be problematic in these designs. The ability of such springs to tolerate off-axis compression forces may also be problematic.

Gordon instructs deforming a machined spring as the principle separating and force management component (U.S. Pat. Nos. 6,579,321, 6,964,686, and 7,331,994). In U.S. Pat. No. 7,316,714 the emphasis is on posterior insertion of a disc prosthesis that can provide appropriate motion. However, this latter design does not appear to accommodate for static and dynamic loading and there appears to be no accommodation for lateral and sagittal translations.

Zubok instructs in U.S. Pat. No. 6,972,038 (Column 3; Line 35) that " . . . the present invention contemplates that with regard to the cervical anatomy, a device that maintains a center of rotation, moving or otherwise, within the disc space is inappropriate and fails to properly support healthy motion." This statement may be true as long as translations within the prosthesis mechanism do not adequately compensate for the total motion induced by an IAR outside of the disc space. The invention as instructed herein, however, by sufficient means of three linearly independent translational degrees of freedom and three independent rotational degrees of freedom (for example, roll-pitch-yaw) within the FSU disc space, said invention can generate any equivalent relative motion of the superior vertebra relative to an inferior vertebra within an FSU whose motion is generated by a moving IAR outside or inside the disc space. Further, the mechanisms in the invention that generate the equivalent motion are so coupled that they prevent separation of any moving elements of the prosthesis beyond mechanically programmed joint limits.

Several approaches by Ferree (U.S. Pat. Nos. 6,419,704, 6,706,068, 6,875,235, 7,048,764, 7,060,100, 7,201,774, 7,201,776, 7,235,102, 7,267,688, 7,291,171, and 7,338,525) primarily instruct how to cushion a prosthetic FSU in various ways. An exception is U.S. Pat. No. 6,706,068, which describes a design to perform certain kinematic motion of a disc prosthesis without dynamic or static cushioning support, and U.S. Pat. No. 7,338,525, which instructs on disc prosthesis anchoring.

Aebi incorporates what essentially amounts to a hook joint (orthogonal revolute joints) in EP1572038B1 as the means for realizing motion. While the Aebi arrangement of revolute joints does allow for sagittal and lateral rotations, it does not engage in the remaining four degrees of freedom in three-space, namely, sagittal, lateral, and axial translations along with axial rotations. Mitchell (U.S. Pat. No. 7,273,496B2) uses two revolute joints by means of orthogonal cylinders placed on top of each other and embedded as a crossbar element between vertebral plates with cavities for accepting the crossbar. This device has the limitations of motion similar to the Aebi device and the further limitation of not kinematically chaining the two plates together with the crossbar.

Khandkar (U.S. Pat. No. 6,994,727 B2) provides two orthogonal convex curvate bearing structures, with offset cylindrical radii of curvature, placed between the vertebral plates. An insert, with orthogonal, variable-curvature concave bearing surfaces, is placed between, and generally conforms to, the orthogonal convex bearings on the vertebral plates. This arrangement of bearings allows sagittal, lateral, and axial rotations of various ranges, dictated by the curvate bearing structures and the insert. The variable curvate surfaces allows some lateral and sagittal translations with FSU distractions, utilizing normal spinal forces to resist the distraction and, hence, the motion. There is no control on the forces involved, so this method could lead to possible stress on other spinal joints. The inserted device is not kinematically chained to the rest of the device and can possibly be spit out. Although, as instructed, the device is self-correcting within a limited range, tending towards a stable equilibrium established for the device in normal position. The variable curvatures result, typically, in line- and point-contact bearing manifolds that can wear the surfaces, possibly causing changes in the performance and characteristic motion of the device over time. In general, motion along the various manifold interfaces involved restricts the flexibility and adaptability of the device to accommodate other motions. DiNello (U.S. Published Application No. 2006/0136062A1) instructs on how to adjust height and angulations of a motion disc after implantation.

Weber, in U.S. Pat. No. 7,582,115, introduces a prosthetic core which is a ball at one end and a plane at the other end that fits respectively, into a curved socket superior plate and a plane surface inferior plate, allowing the core element to slide as well as permitting the superior vertebral plate to rotate about the ball end. The five degree of freedom planar-mobile ball-and-socket mechanism instructed here kinematically restricts the FSU to its nominal workspace while realizing the same number of freedoms in a significantly different manner and providing shock absorption and variable load bearing as well.

With respect to the lower vertebra in an FSU, all possible, natural loci of motion of any four non-planar, non-collinear points located in the superior vertebra define the natural workspace of an FSU. This workspace varies from one FSU to another on the spine and from one individual to another, creating considerable spinal disc prosthesis design problems.

The device of the subject invention provides a general motion spatial mechanism. The device solves certain natural motion and shock absorbing characteristics that are problematic for a spinal disc prosthesis and offers a scalable mechanism for disc replacement without loss of general motion capabilities in the FSU.

SUMMARY OF THE INVENTION

Embodiments of the subject invention provide a device capable of providing mechanically-linked, relative spatial movement, with up to six-degrees of freedom. The embodiments of the device described herein can be utilized in a multitude of mechanical applications to provide motion capabilities. Advantageously, embodiments of the subject invention can be installed in a Functional Spinal Unit (FSU) of a patient and can facilitate complex relative motion between the vertebrae of the FSU by allowing independent sagittal, lateral, and axial displacements and up to three independent rotations.

The motion elements of any particular embodiment of the spinal disc prosthesis of the subject invention are typically operated and controlled by the muscles and ligaments of the spine, when the subject invention is installed in an FSU. Spinal muscles and ligaments can drive the spring-damping system and resultant motion of the prosthesis. The kinematic generality of the motion capabilities of the subject invention prosthesis, allows natural movements of any FSU along a spine in which an appropriately dimensioned and parameterized prosthesis is placed. Specifically, with appropriate dimensioning and parameter adjustments, the workspace embodiments of the subject invention can be tailored to meet the natural or clinical motion requirements of any FSU along the spine.

The dimensions of the device embodiments can vary depending upon intended use, minimum and maximum compression and extension rates, and other factors known to those with skill in the art. For example, embodiments utilized with the spine of a patient can require different dimensions depending upon intended location within the spine. Installation towards the more cranial end of the spine can necessitate smaller dimensions than would installation nearer the caudal end. In a specific example, a cervical spine embodiment of the subject invention can be between approximately 6 mm and approximately 8 mm in height when the device is in a fully compressed state FIG. 5 and between approximately 8 mm and approximately 10 mm in a fully extended state FIG. 6. These dimensions can vary according to application and are not meant to restrict the scope of the subject invention.

It should be understood that the embodiments of the invention described herein are not limited to cervical applications. It can be scaled and parameterized for application anywhere on a spine or in other medical or non-medical mechanical applications requiring a general, compact, passive connection between elements that move relative to each other with one, and up to six, independent degrees of freedom. Several significant design features of the invention enable such a compact design and are discussed in the ensuing description.

In one embodiment, a superior vertebral plate of the invention fixes to a superior vertebra and an inferior vertebral plate of the invention fixes to an inferior vertebra of a Functional Spinal Unit (FSU). The superior surface of a superior vertebral plate and the inferior surface of an inferior vertebral plate each can have one or more guide pins and/or one or more fusion spikes. The guide pins and/or fusion spikes can also be configured with cavities, channels, tunnels, holes or other types of openings and/or depressions. The fusion spikes can secure the plates to the vertebrae and enable and encourage vertebral bone growth around, into, and/or through the fusion spikes to secure the aforesaid plate surfaces to the vertebrae of an FSU. In a further embodiment, the guide pins are longer than the fusion spikes, which allow them to engage the FSU vertebrae before the fusion spikes. The guide pins can be used to accurately position the invention within the disc space of an FSU by placement into predrilled pilot holes within the aforesaid vertebral surfaces. The fusion spikes can be pressed into cancellous bone, with or without the assistance of pilot holes within the aforesaid vertebral surfaces, after the guide pins have positioned the device properly. The geometric shape of the fusion spikes can also be such that the deeper the fusion spikes penetrate the cancellous bone, the greater the wall pressure between the fusion spikes and the bone where there is contact. In a further embodiment, the fusion spikes can be barbed. In an alternative embodiment, the fusion spikes do not require pilot holes. The use of pilot holes can be dependent on the geometric shape and mechanical strength of the fusion spikes and whether the cancellous bone might fracture under insertion stress. In a specific, non-limited, example for a cervical disc, fusion spikes can be conical in shape and project between approximately 0.5 mm to approximately 2 mm above the plate surface for cervical applications. In this example, the guide pins can be right circular cylinders topped by a conic frustum, or chamfered to promote easy insertion. In a further, non-limiting example, the total height of a guide pin can be between approximately 0.5 mm to approximately 2 mm taller than the largest spike in cervical applications. In a further embodiment, guide pins can comprise a material that easily slides against, or has minimal friction with, cancellous bone. In a further embodiment, the spike and vertebral plate surfaces can be dimpled with a micro-rough surface. In U.S. Pat. No. 7,060,100, Ferree instructs the use of a four-armed conic shaped spike with holes to help attach vertebral plates to vertebrae. In a much earlier work, disclosed in WO199404100, Mazda instructs the use of conical fusion spikes with side edges that allow a wrench to grip the cones in order to screw them into the vertebral plates. In the current invention, the use of guiding pins and the relationship between the guiding pins and the fusion spikes for secure, accurate placement of the prosthesis appears to be a significant deviation from Mazda and Ferree.

There can be any of a variety of overall outer circumferential shapes to the device of the subject invention, including circular, oval, square, rectangular, triangular, or other polygonal shapes. Two particular, but non-limiting, embodiments, discussed herein, convey the versatility of the device of the subject invention. One embodiment has an overall shape that is a rounded-corners square model (FIG. 3, FIG. 7). Another embodiment has an overall circumferential shape that is a cylindrical model (FIG. 25, FIG. 27) with corresponding elements. As used herein, identical element can be defined as designs with zero variations to make the term "corresponding" reflexive. For example, 9-1 and 9-2 can be corresponding superior vertebral plates, 1-1 and 1-2 can be corresponding inferior vertebral plates, and 6-1 and 6-2 can be corresponding retainers for "ball-cylinders" 5-1 and 5-2. Each pair of elements provide the same functional purpose in both models and can have many common features, for example, 9-1 and 9-2 can be fixedly attached to the superior vertebra of an FSU and provide a cavity space for a socket and socket-retainer bearing to establish a planar pair; 1-1 and 1-2 can be fixedly attach to an inferior vertebra of an FSU and provide cavity space for a ball-cylinder element to establish an axial prismatic pair with that element; 6-1 and 6-2 can retain a ball-cylinder in a cavity of an inferior vertebral plate and can further function as a joint stop for extension displacements of the prismatic pair. For the two models, sockets 8-1 and 8-2 are identical, as are spherical sliders 7-1 and 7-2, superior mandrel 4-1 and 4-2, spring and/or cushion elements 3-1 and 3-2, and inferior mandrels 2-1 and 2-2. While the corresponding ball-cylinders 5-1 and 5-2 are not identical, they can be made so by changing the number, size, and location of tab elements 5-1-1 to be the same as 5-2-1. Such a modification of 5-1 would require modification of the cavities of inferior vertebral plate 1-1 to match those of inferior vertebral plate 1-2, thus, making the interior features of both inferior vertebral plates identical in such a case.

Embodiments of the subject invention can have many corresponding variations in the interior elements, which are those elements between the superior and inferior vertebral plates.

Variations in a socket relate to whether it accommodates a spherical slider, in which case it must have a spherical slider cavity to match the requirements of the chosen slider geometry, such as sockets 8-3 (FIG. 18), 8-4 (FIG. 20) and 8-7 (FIG. 22) whose cavities can be designed to accommodate spherical sliders 7-3 (FIG. 17A and FIG. 17B), 7-4 (FIG. 19A and FIG. 19B) and 7-7 (FIGS. 21A and B), or whether the socket has no cavities and has fixedly attached, or anchored to it, concave spherical sliders 7-6, such as socket 8-6 (FIG. 35). The caudal end of a concave spherical slider 7-6 functions like the caudal end of mobile socket 7-1, except that 7-6, in this embodiment, cannot move relative to the socket.

In one embodiment, a convex spherical slider 7-5 (FIG. 33) fixedly attaches to a ball of a ball-cylinder, resulting in another type of anchored slider. The cranial end of 7-5 can function like the cranial end of mobile socket 7-1, except that, in this embodiment, it does move relative to the ball, and, thus, can use socket 8-5=8-1. Socket and ball-cylinder variations can include designs that accommodate a mix of anchored and mobile spherical sliders. Such variations are considered to be within the scope of this disclosure and the claims herein.

Corresponding ball-cylinders 5-3, 5-4, 5-5, 5-6 and 5-7 can possess different spherical slider cavities to accommodate different fixed or mobile spherical sliders, but, otherwise, in the embodiments disclosed herein, look and function like 5-1. All these variations of the subject invention are illustrated to fit within an inferior vertebral plate 1-1, but an additional variation of each of the aforementioned ball-cylinders can be made to fit into the cylindrical version 1-2 by changing the number, size, and location of tab elements 5-$x$-1, x=3, 4, 5, 6 to those of 5-2-1 on 5-2. Such variations are considered within the scope of claims herein.

The devices of the subject invention can achieve up to six degrees of freedom, including up to three independent rotational degrees of freedom and up to three independent linear degrees of freedom, such that the device of the subject invention facilitates sagittal, lateral, and axial vertebral displacements and general rotations when utilized in the spine of a patient. The interior mechanisms of the invention kinematically and mechanically connect or link the superior and inferior vertebral plates, which are rigidly attached to superior and inferior vertebrae in an FSU, respectively, by means of mechanically interlocked and inseparable joint elements in a kinematic chain within the device. Under nominal FSU workspace motions, all elements of the invention remain mechanically linked together, yet allow completely general FSU workspace motion.

Both the rounded-corners square and cylindrical embodiments, and variations thereof, comprise a six-degrees-of-freedom (6-DOF) modular prosthetic mechanism realized by a set of serially linked joint pairs, such as, for example, a planar pair between a superior vertebral plate and a socket upper surface; a spherical pair between a socket's lower concave, non-hemispheric, spherical surface and a conformable, non-hemispheric spherical-cap or "ball"; a prismatic pair between a "ball-cylinder" and an inferior vertebral plate, where a ball-cylinder comprises the union of a ball (spherical cap) and a cylindrical shell.

One embodiment utilizes a socket-retainer bearing to hold a planar pair together, which can limit its two dimensional range of motion. In a further embodiment, the planar pair links to a "ball-and-socket" spherical pair constrained by one or more spherical sliders. Spherical sliders can restrict the motion of a spherical pair to rotations, that is, the slider forces the curvature centers of the two surfaces to remain coincident, and, simultaneously, can limit the range of the pair's three independent angular rotations. The ball-and-socket links to a prismatic pair, whose axis is never in the plane of the planar pair for all nominal FSU workspace motions and, thus, is linearly independent of the planar motion. The displacement range of the prismatic pair is limited by interference between the inferior vertebral plate and the ball-cylinder at the minimum displacement and between the ball-cylinder retainer and the ball-cylinder tabs at the maximum displacement. In this embodiment, no loss of a degree of freedom of any of the joint pairs can occur during any nominal FSU workspace motion.

The subject invention is capable of working in a negative force field with respect to gravity (e.g., "upside-down") because all joint pairs are connected and constrained to translate or rotate according to their degree(s) of freedom. Linkage between the superior and inferior vertebra of an FSU can be established for the subject invention with the following embodiment. In this embodiment, a planar pair is fused or otherwise fixedly attached to a superior vertebra of an FSU. In a further embodiment, a planar pair, comprising a superior vertebral plate and a socket, is linked to a spherical pair through the body of the socket. A spherical "pair", comprising a socket, a spherical cap and one or more spherical sliders, can be linked to a prismatic pair through the body of the spherical cap, which can be further fixedly attached to a hollow cylinder. In a further embodiment, a prismatic pair, comprising a ball-cylinder and an inferior vertebral plate, is fixedly attached to an inferior vertebra of an FSU.

In the specific embodiment of a cervical implementation, the planar joint can allow the superior vertebral plate to move with respect to the socket a nominal approximately ±1 mm in both the sagittal and lateral direction, independently. In a specific embodiment, for a rounded-corners square vertebral plate geometry (FIG. 1 and FIG. 3), the permissible planar motion, in rectangular coordinates (x,y), defined at the centroid of the planar joint when the invention is in a neutral position, can be (x,y)=(approximately ±1 mm, approximately ±1 mm). For a cylindrical vertebral plate geometry, the motion, in polar coordinates (r,θ), defined at the centroid of the planar joint when the invention is in a neutral position, can be approximately ±1 mm in the radial direction r from the cylinder's center axis at any direction θ from the center with respect an angle reference.

A socket, as featured in an embodiment of the subject invention, can have a top planar surface and a bottom concave spherical surface. The planar surface participates in a planar pair joint and the concave spherical surface participates in a spherical pair joint. A planar surface within a cavity of the superior vertebral plate comprises the second planar surface of the planar pair. A convex spherical surface of a spherical cap is the second spherical surface comprising a spherical pair joint. A spherical cap can be less than a hemisphere. Spherical caps, less than a hemisphere will be referred to as a "ball", although that nomenclature is more conventionally applied to a sphere or at least a spherical cap larger than a hemisphere. A similar convention applies to a socket's spherical surface. A socket can have a convex spherical surface less than a hemisphere with the same center of curvature as the "ball".

A ball-and-socket spherical pair joint can accommodate up to three rotational degrees of freedom of motion, and by mechanical transference through the planar joint, allows a superior vertebral plate up to three independent rotational freedoms with respect to more caudal elements of the device, including the inferior vertebral plate. Superior vertebral plate rotations about the central axis of the socket plane may not be mechanically transmitted through the socket, in some embodiments, and, therefore, can be accommodated there and not require engagement of more caudal motion elements of the device. However, geometric configurations of the socket-retainer bearing within the superior vertebral plate and the geometric contour of socket retained within that plate can be devised to control superior vertebral plate rotation about the central axis of the plane of the socket. For example, an elliptically shaped socket-retainer bearing and an elliptically shaped socket, both with a 2:1 major-to-minor axis ratio, can limit central axis rotations to be less than approximately +45 degrees. An elliptic design establishes, however, a non-uniform range of motion for the planar pair. Maximum sagittal displacements can be greater than maximum lateral displacements given the geometry mentioned. A person with skill in the art would be able to determine alternative curvate designs of socket and socket-retainer bearing elements to establish other, possibly complex, motion constraints on the planar pair. Such variations are contemplated to be within the scope of the subject invention.

A spherical-pair joint can be rotationally interlocked by means of a mobile spherical sliding mechanism or, more simply, a mobile spherical slider. In one embodiment, a mobile spherical slider is not fixedly attached to either element of a spherical pair, but rather, can rotate and slide simultaneously on accommodating spherical surfaces within cavities in both surfaces of the spherical pair. The spherical slider's caudal and cranial end spherical surfaces and corresponding cavity spherical surfaces can also have the same center of rotation as the spherical pair joint.

A spherical slider, fixedly attached to one spherical surface but free to rotate and slide within a cavity of the other spherical surface of a spherical pair, will be referred to herein as a convex spherical slider or a concave spherical slider as the free end surface of the slider is either convex or concave spherical. A convex or concave spherical slider's non-attached end can slideably rotate relative to its cavity spherical surface. A convex or a concave spherical slider will be referred to as an anchored spherical slider in contexts that clearly indicate the statement applies to either type. Also referred to herein, "spherical slider", and sometimes just "slider", may be used without any defining adjective such as "mobile", "anchored", "convex", or "concave" or "spherical", where the meaning is clear from context, or the usage applies to all three types of sliders: mobile, convex, and concave.

As used herein, the term operational integrity when applied to a spherical pair joint means that displacements between the centers of curvature of the involved spherical surfaces can be tightly constrained to be approximately coincident to restrict motion of the joint to rotations about a common center of curvature. The term operational integrity as used herein and applied to a planar or prismatic pair joint means that displacements between the involved surfaces of the joint can be tightly constrained to planar or one dimensional slider motion, respectively.

All three types of spherical sliders can simultaneously provide rotation joint stops for up to three rotational degrees of freedom of a spherical pair and can maintain operational integrity of a spherical pair. When the cavity openings of a spherical pair are too narrow to allow a mobile spherical slider's caudal and cranial end elements to be withdrawn, the spherical pair maintains operational integrity during rotations, even under the influence of forces tending to separate the pair's center of curvature. The same situation can apply to spherical pairs that incorporate anchored spherical sliders, except only one surface of the pair has a cavity and that cavity opening is too narrow to allow the sliding end of the anchored slider to be withdrawn from its cavity.

All three types of spherical sliders can simultaneously establish angular range limits or angle stops for up to three independent rotation angles, regardless of whether spherical pair cavity openings are narrower than the end elements that fit into them or not. Therefore, in those applications where a spherical slider serves as an angular joint stop, but is not required to maintain operational integrity, as might be the case in a ball-and-socket joint where a socket encloses more than a hemisphere of a ball, spherical pair cavity openings can be wide enough to allow the spherical slider ends to be easily inserted or withdrawn without interference with the edges of the cavity openings. In strictly joint angle control applications, a spherical slider can be, but is not limited to be, a cylinder-like element of curvate cross-sectional geometry whose cranial and caudal end surfaces are spherical rather than planar, as they would be for a pure cylinder. Since the cranial, caudal and stem of a spherical slider can have the same circular cross section in such cases, a simple ball-bearing can serve as a spherical slider in such cases, but unless the bearing can oppose separation forces acting on the spherical pair, it cannot contribute to kinematic connectivity.

The interior space of a spherical pair cavity allows a spherical slider end to rotationally slide within the cavity on a bounded spherical surface. A curvate, possibly non-planar, boundary of a slider's spherical surfaces, located at its caudal and cranial ends, and curvate boundaries of the cavity spherical surfaces that those slider surfaces engage, can together determine the angle rotation limits of the spherical pair into which the slider is installed. The shape of the "stems" lateral surface can interact with the edge shapes of the cavity orifices and can also affect/determine the angle rotation limits. One can also use various combinations of caudal end, cranial end, stem, and cavity lateral surface shapes to achieve a plethora of joint angle controls. As an extreme example, a spherical pair and a spherical slider, either mobile or anchored, can be configured to perform as a one-degree-of-freedom revolute pair (FIG. 22). To achieve such a configuration, consider an embodiment having a spherical slider 7-7 (FIG. 21A and FIG. 21B) and spherical pair (5-7-2, 8-7-2). The slider width can equal the width of the cavities in the spherical pair. The left and right lateral boundaries 7-7-6 can be planes that match up with cavity planar surfaces, generally making a closed planar pair between the lateral sides of the slider and the lateral side of its cavities. All these planes can be parallel to the sagittal plane. The planar pair of this example allows translations and rotation in the sagittal plane. During sagittal rotations, such as, for example, rotations that take place during flexion and extension of an FSU, spherical end surfaces of the slider slideably rotate upon larger sized cavity spherical surfaces opposite the cavity openings. The sagittal joint range can be dictated by those spherical surfaces. For example, the sagittal angular dimension of a cavity spherical surface can be approximately ten degrees larger than the sagittal angular dimension of the slider's spherical surface. For a mobile spherical slider, this choice will provide approximately 10 degrees flexion and approximately 10 degrees extension of an FSU. For an anchored spherical slider of comparable dimensions, the flexion and rotation angle limits, in this instance, would be approximately 5 degrees.

In particular embodiments, the caudal element of a spherical pair joint can revolve unconstrained about a spherical slider's caudal spherical surfaces' central axis and the cranial element of a spherical pair joint can revolve unconstrained about a spherical slider's cranial spherical surfaces' central axis. This pertains regardless of the nominal operational position of the sliders caudal and cranial central axis relative to their respective cavity spherical surfaces. Typically, the caudal and cranial central axes are coincident and will be simply referred to as the slider's central axis. This is the case for embodiments considered herein.

A particular, but important, example of unconstrained rotations about a slider's central axis occurs when the cavity and slider spherical surfaces have circular boundaries, such as with the embodiment having a ball-and-socket spherical pair (5-1-2, 8-1-2) and spherical slider 7-1. With this embodiment in the neutral position (FIG. 4), the slider's central axis lines up with the central axis of the ball-cylinder 5-1. Rotations of the socket 8-1 about the central axis can be seen to be unconstrained by the slider. The ball-cylinder is also not constrained by the slider, but, the tabs 5-1-1 prevent such rotations. If the cylinder 5-1-3 were polygonal or elliptical, rotations about the central axis can be prevented even without the tabs. When the boundaries are circular, the slider can produce a uniform angular range from the neutral position about any axis comprised of a linear combination of the sagittal and lateral axes. These observations about unconstrained rotation of the socket or ball about the slider's central axis, such as seen in the embodiment in FIG. 5 and FIG. 6, still apply, but the central axis of the slider has moved and is no longer coincident with the central axis of the ball-cylinder.

An alternative embodiment employs a spherical slider 7-3 that has elliptical boundaries and can constrain rotations about its central axis. In this embodiment, the lateral and sagittal rotations have different angular joint limits with the former twice as large as the latter. Spherical sliders with circularly bounded spherical surfaces, such as shown, for example by 7-1, 7-2, and 7-4, supported by circularly bounded cavity spherical surfaces, can produce uniform joint angle control from the neutral position about any axis comprised of a linear combination of the sagittal and lateral axes. Typically, such sliders and cavities provide no constraint on central axis rotations.

For a given spherical slider's caudal and cranial spherical surface angular dimensions, a rotational angular range for a spherical pair, in a particular plane of rotation, can be increased by increasing the cavity spherical surface angular dimensions within the bodies of the surfaces pair, or decreased by decreasing the cavity spherical surface angular dimensions within the bodies of the surface pair, where the increase or decrease is along the arc of rotation generated by that plane and the cavity spherical surfaces. These increases and decreases can be uniformly applied to all such curves on the cavity spherical surfaces or just specific regions. Changing angular dimensions of the cavity spherical surfaces in just certain regions can generate asymmetric rotation constraints, since now the cavity spherical surfaces will restrict the spherical slider rotations along some directions more or less than others. Appropriate modifications, as would be apparent to a person skilled in the art, of a spherical slider's spherical surface boundaries and fixing the cavity spherical surfaces, or both, can achieve similar affects. Such modification are contemplated to be within the scope of the subject invention.

Multiple spherical surfaces on a spherical slider, in conjunction with multi-spherical surfaces within cavities of a spherical pair into which the slider fits, can create, a multi-spherical-surfaced spherical "pair", when all spherical surfaces have the same center of curvature. All such modifications to spherical pair joints are considered to be encompassed by the subject application and claims.

Two or more spherical sliders of any combination of the three types (mobile, concave, convex) can be used to maintain the operational integrity and angular limits of a spherical pair during nominal FSU workspace motion, even when the spherical surfaces of the pair are both less than a hemisphere. Since the central axes of all spherical surfaces of a spherical slider typically pass through the common center of curvature of a spherical pair at all times during rotation, it is generally true that no two spherical sliders utilized in the same spherical pair can have coincident central axes. Thus, when a turning axis coincides with the central axis of one spherical slider, rotations about it can be controlled by the other spherical sliders. Thus, up to all three independent rotational angular ranges can be constrained using two or more spherical sliders, even if neither one acting alone can do so. If the central axes of the sliders intersect at right angles, rotations about any axis can be controlled uniformly, otherwise not. Embodiments of the invention include the use of multiple spherical sliders in a spherical pair joint where neither surface of the pair is required to be a hemisphere or larger, but pairs larger than a hemisphere are not excluded, either.

Spherical sliders can be employed for any spherical pair used in a mechanical device and applications are not restricted to disc prosthetics. Further, a spherical slider can employ higher order pairs. In one embodiment, ball-bearings can be inset and arranged of various spherical surfaces to facilitate rotation and reduce friction and binding. In one embodiment, three ball-bearings can be inset and arranged on the vertices of a spherical triangle laid out on slider caudal and/or cranial spherical surfaces to facilitate rotation by reducing friction and binding. In another embodiment, ball-bearing rings can be fastened around the caudal and cranial ends, wherein the bearing contact points are so configured that they simultaneously lie on a cavity spherical surface. In a particular embodiment described herein, a spherical slider 7-4 utilizes a hall-bearing ring that can have bearings that alternately conform to upper convex and then lower concave spherical surfaces found within each cavity of the spherical pair.

In one embodiment, concave spherical slider usage is illustrated in FIG. 34 FIG. 35 and FIG. 36. Two concave spherical sliders constrain all three independent rotation angles of a spherical pair joint. In this case, rotation angle limits from the neutral position about any axis comprised of a linear combination of sagittal and lateral axes can be limited to approximately ±10 degrees for a particular embodiment. For rotations about the central axis from the neutral position, the angular rotation of the sliders on a circle of latitude on the cavity spherical surface will eventually cause interference with the cavity walls or edges. The rotation angle limit about the central axis of the ball-cylinder, for the invention in its neutral position, can be approximately ±14 degrees for the same particular embodiment.

A single, especially configured, spherical slider can also control all three independent rotation angle limits. In one embodiment, an elliptic bounded spherical slider 7-3 (FIG. 17A and FIG. 17B) can limit axial rotations in exchange for reduction in joint limits about other axes. The sliding surfaces in this embodiment are still spherical, but the boundaries of the spherical surfaces are elliptical. For example, the elliptic bounded spherical slider described in FIG. 17A and FIG. 17B has a major-to-minor axis length ratio of approximately 2:1. For this elliptic bounded spherical slider surface, lateral angle limits from the neutral position are reduced from approximately ±10 degrees to approximately ±5 degrees and sagittal angle joint limits are kept at approximately ±10 degrees. Axial rotations, however, are now restricted and confined to a range of approximately ±45 degrees when the invention is in its neutral position. This elliptic slider illustrates how varying the geometry of the slider and its cavities can influence the angular joint limits and such variations are considered to be within the scope of the subject invention and claims herein.

Anchored spherical sliders can permit up to three degrees of rotational freedom of a spherical pair joint, maintain the operational integrity of the spherical pair, and can control up to all three angular rotation limits (stops) by appropriate design of the anchored spherical sliders and their receiving cavities, as in the spherical slider case. For equal spherical slider and anchored spherical slider dimensions and equal joint cavity sizes, however, spherical sliders can allow larger angle variations than anchored spherical sliders.

The embodiments of spherical sliders, such as shown in FIG. 33 and FIG. 34, can have an exposed structure with the same dimensions of the corresponding elements of a mobile spherical slider. An anchored spherical slider with the same dimensions as corresponding parts of a spherical slider typically constrain angular displacements to half of that of the spherical version, given the same cavity space for both types. In one embodiment, the anchored spherical slider 7-5 of (FIG. 33) is convex and 7-6 of (FIG. 34) concave. The exposed projection of 7-5 is identical to the upper "half" of 7-1 and the exposed projection of 7-6 is identical to the lower "half" of 7-1.

In general, variations in spherical slider geometry and spherical pair cavity geometry and the locations of the spherical pair cavities on their spherical surfaces, together, can produce sophisticated control of rotational constraints. In particular embodiments, the three types of spherical sliders can be combined together in various counts and combinations. Such as, for example, two spherical sliders, one a convex spherical slider and the other a mobile spherical slider, both sliders and their respective cavities designed to allow the same range of angular motion, can be used conjunctively. Typically, the mobile spherical slider and its two associated cavities will be each half the size of the anchored spherical slider and its single cavity when the two types are used together. A person with skill in the art, having benefit of the subject disclosure, would be able to determine any of a variety of such spherical pair cavities and corresponding surfaces to permit and control rotation and such variations are contemplated to be within the scope of the subject invention.

A superior-vertebral-plate-and-socket planar pair (9-1-1, 8-1-1) or (9-2-2, 8-2-1) in conjunction with a socket and ball spherical pair (8-1-2, 5-1-2) or (8-2-2, 5-2-2) can realize up to five of the maximum six independent degrees of freedom of motion possible between the superior and inferior vertebral plates of the subject invention: two independent linear translations from the planar pair and three independent rotational degrees of freedom from the ball-and-socket spherical pair. In one embodiment, a sixth translational, independent degree of freedom of motion of the subject invention can be realized by an axial prismatic pair. In a particular embodiment, an axial prismatic pair comprises the exterior wall of cylinder 5-1-3 (5-2-3) and lateral surfaces of tabs 5-1-1 (5-2-1) of ball-cylinder 5-1 (5-2) and the lateral surfaces of cavities 1-1-2 (1-2-2) and 1-1-3 (1-2-3) of inferior vertebral plate 1-1 (1-2). In a further embodiment a superior segmented-wall mandrel 4-1 (4-2), which can be fixedly attached to 5-1 (5-2), and the inferior segmented-wall mandrel 2-1 (2-2), which can be fixedly attached to 1-1 (1-2), also participates in the prismatic pair.

Ball-cylinder 5-1 (5-2) can comprise a non-hemispheric spherical cap with curvate boundary fixedly mounted on a hollow, curvate cross-section cylinder 5-1-3 (5-2-3). A further embodiment utilizes joint limit tabs 5-1-1 (5-2-1). The curvate boundaries of the cylinder and the spherical cap can agree in shape and, in a particular embodiment, can be circular as shown in the figures. A superior segmented-wall mandrel 4-1 (4-2) can be fixedly attached at the centroid of the flat, underneath side of the spherical cap, within the hollow cylinder cavity. An inferior segmented-wall mandrel element 2-1 (2-2) can be fixedly attached at the centroid of the floor of a cavity within the inferior vertebral plate 1-1 (1-2). In one embodiment, part of the axial prismatic joint includes the superior and inferior mandrels sliding relative to one another along the axis of the cylinder as it moves up and down along its central axis. In a further embodiment, the segmented walls of the mandrel elements mesh and do not interfere with each other, the cylinder, or the spring or other cushion elements, as they slide past one another during prismatic joint action. With this embodiment, within the prismatic joint range, the segmented-wall mandrel elements provide continuous columnar support for spring and cushion elements on the central axis of the cylinder.

The ball-cylinder can perform as a central, compressible and extendible hydraulic cylinder. In a further embodiment, the ball-cylinder can incorporate appropriate hydraulic portals (FIG. 38 and FIG. 39) to allow fluid or gas flow from the cylinder chamber into, and out of, other cavities and spaces within the device during the pumping action of the axial prismatic joint. In conjunction with one or more springs or other cushioning elements, the ball-cylinder can provide hydraulic damping and shock absorbing capabilities to the subject invention. Refer to U.S. Pat. Nos. 7,361,192, 7,799,080, and 7,927,375, as well as U.S. Patent application no. US2010/0324688A1 and Published PCT Application No, PCT/US2010/37721 for instruction, which are included herein by reference.

As mentioned above, the wall segments of the superior and inferior mandrels can interlace and do not interfere with one another as their lateral wall-edge surfaces slide by each other with the rise and fall of the prismatic pair, which can include the ball-cylinder and inferior vertebral plate. In one embodiment, the wall segments of the superior and inferior mandrel completely mesh into a minimum spatial occupancy at full compression and form a compact interlaced column. In a further embodiment, at maximum allowed extension, the mandrel wall segments still overlap and are never separated. In a still further embodiment, where the segmented-walls of the superior and inferior mandrels overlap, there are no wall gaps (with the exception of bearing clearances) around the circumference of the mandrel column, otherwise, there are alternating wall segments and wall gaps. Thus, no matter the axial motion, the mandrel can provide central mechanical support for spring or other cushioning elements along the entire length of the cylindrical cavity.

In one embodiment, each wall-segment of the superior and inferior mandrel can be an approximately 60 degree section, resulting in three wall-segments apiece. Interlacing these wall-segments allows them to slide past each other around a central axis. In an alternative embodiment, each wall-segment of the superior and inferior mandrel can be an approximately 45 degree section, such that each mandrel has two wall-segments. While the 60 and 45 degree wall segments are described herein, it will be understood by a person skilled in the art that there could be any number of possible ways to divide the mandrel column into interlacing superior and inferior interlacing wall segments using segments of different angular dimension. Such variations are deemed to be within the scope of the subject invention.

As mentioned, in the embodiments disclosed herein, the joint elements remain moveably attached to one another by means of a kinematic chain throughout nominal FSU workspace motion, thus maintaining the structural integrity of the device in all FSU configurations. In addition, the kinematic chain can maintain the structural integrity of, and enables normal operation of the components of the embodiments of the subject invention, even when the body or structure into which the device is installed happens to be upside down or any other orientation with respect to gravity.

In a further embodiment, the vertebral plates can be rigidly fixed to the superior and inferior vertebrae of a Functional Spinal Unit (FSU). In alternative embodiments, the vertebral plates can be, with modification of the device's vertebral plates, modularly fixed to such plates. For example, U.S. Pat. Nos. 7,361,192 and 7,799,080 to Doty, which are hereby incorporated by reference, describe embodiments of a modular disc mechanism that can connect with a superior and an inferior vertebral plate by twisting or screwing into the superior and inferior vertebral plates, which can further be connected to the respective vertebra. Doty further describes a superior and an inferior vertebral plate that possess an opposite screw sense, such that twisting or turning in a single direction connects the modular prosthetic disc mechanism to both vertebral plates simultaneously. This can enable easier installation and replacement of the prosthetic device if necessary.

Conical fusion spikes can also be fixedly attached to the superior and inferior plates as illustrated herein. In one embodiment, the conical fusion spikes can have cutaway surfaces, one or more holes, micro-barbs, and/or indents or other structures to accommodate cancellous bone growth and, thus, rigidly fix the superior and inferior plates to the superior and inferior vertebrae of an FSU, respectively, by bone fusion into and about the device. The bone contact surfaces of the fusion spikes and the superior and inferior vertebral plates can also be treated, micro-porous surfaces to encourage bone growth and the fusing of the vertebral plates to the vertebral bones. The number, size, and geometric placement of the fusion spikes can be determined by various design considerations and stresses permitted by the cancellous bone. In one embodiment, for greater stability, there are at least three fusion spikes. Alternative embodiments utilize four, five, or even six fusion spikes for greater bone fixing. In a further embodiment, undersized pilot holes for the fusion spikes can be drilled to assist in proper placement and reduced stress on cancellous bone.

In one embodiment, central guide pins can also be fixedly attached to the superior and inferior plates, as illustrated herein. Central guide pins can be longer than the fusion spikes and can be partially inserted into pilot holes drilled into the vertebra interface surface before the fusion spikes engage the cancellous bone. In a particular embodiment, at least one guide pin is used on each of the vertebral plates and pilot holes are drilled into the inferior and superior vertebrae interface surfaces before the fusion spikes engage the cancellous bone. In an alternative embodiment, more than one guide pin can be used. In a particular embodiment, at least one guide pin is used and is centered on the inferior and one on the superior vertebral plate of the invention. The guide pins can enable stable insertion and accurate placement of the device into the disc space of an FSU and can make an isotropic device workspace volume available to the FSU. Generation of anisotropic workspace volumes can be achieved by creating different joint stop limits for the various joints in possible conjunction with drilling the pilot holes for guide pins at points other than the vertebrae centroids. Guide pins can also have indents channels and other surface treatment, the same as, or similar to, fusion spikes, to encourage bone fusion to the pin.

In one embodiment, a tough, flexible boot fixedly attached to the superior and inferior vertebral plates can be designed to be under tension in the FSU's neutral position and, thus, oppose increasing separation of the device components. Boot tension also can resist torsion loads on the device, especially by weaving tough diagonal fibers within the boot as instructed in U.S. Pat. Nos. 7,361,192, 7,799,080, and 7,927,375, as well as U.S. Patent application no. US2010/0324688A1 and Published PCT Application No, PCT/US2010/37721 which are all incorporated by reference herein.

In a further embodiment, a spring or other resistance-providing element within the central cylinder opposes compression of the vertebral bodies and can be designed to be under compression in the neutral position of the FSU. The boot and the spring elements, therefore, can act antagonistically and, further, can be in equilibrium with the cranial loading when the FSU is in a neutral position. In the neutral position, therefore, the spring element, boot and cranial load can all balance to produce a nominal, normal, intervertebral separation. In those cases where boot elements are not used, the spring can balance only the load.

In a one embodiment, there can be a compressible or non-compressible bio-compatible fluid, within the central cylinder, in conjunction with a central spring element, which can provide shock absorbing characteristics in addition to the static resistance to compressive loads along the central axis (see U.S. Pat. No. 7,927,375, as well as U.S. Patent application no. US2010/0324688A1 and Published PCT Application No, PCT/US2010/37721. In a further embodiment, the bio-compatible fluid can have a high viscosity. In a further embodiment, the boot can be sealed, such that surrounding bodily fluids cannot contact the functional elements of the prosthetic device. In still a further embodiment, a sealed boot can seal in fluids to lubricate the functional elements of the prosthetic device. The central prismatic joint can further act as a hydraulic pump, to help divert compression shocks to the walls of the boot, causing the boot to bulge or otherwise distort in shape and absorb some of the energy of the shock (see U.S. Pat. Nos. 7,361,192, 7,799,080, and 7,927,375, as well as U.S. Patent application no. US2010/0324688A1 and Published PCT Application No, PCT/US2010/37721, which are all incorporated herein by reference). Fluid reservoirs can exist in the various cavities of the device. In one embodiment, the available space within the ball-cylinder at maximum compression can be used as a fluid reservoir. Various hydraulic circuits can also be devised for the subject invention by one skilled in the art and such variations are considered to be within the scope of this invention.

The complete motion generality of the device of the subject invention makes it applicable to any of a variety of situations. Advantageously, the device can be used to assist in maintaining natural spinal flexibility and motion during simultaneous, dynamically changing, curvilinear axial, lateral and sagittal rotations and translations, regardless of the details and wide variations of FSU workspace motion.

The device can also assist in accommodating variable disc spacing under static and dynamic load during normal FSU operation. For example, the disc spacing under static load in the neutral spinal position can be selected by adjusting certain spring and cushion elements of the device. The invention can absorb compression shocks, sustain static loads, respond to dynamic loads, and assist in alleviating spinal cord and nerve root compression. Embodiments also utilize a tough, flexible boot to resist torsion and extension forces. Other embodiments utilize a second boot covering that can prevent the transfer of fluids and/or gasses. In alternative embodiments, these two functions can be realized by a single boot covering that performs both functions.

The mechanism's components, when coupled together, can form a device that preserves its own mechanical integrity, connectedness (i.e., inseparable kinematic chain), and motion properties throughout the biologically constrained motion space (i.e., the workspace) of an FSU. The complete generality of the device can also allow for modification of the range of motion parameters and workspace, physical size, material composition, and mechanical strength to suit ordinary mechanical applications as well as spinal disc prosthetics.

When utilized as a spinal prosthetic, the complete 6-DOF motion capability of the prosthetic disc linkage mechanism can allow natural motions dictated by the muscles and ligaments of the spine. Throughout nominal motion, the system of the subject invention is capable of stabilizing an FSU because of its ability to maintain continuity of mechanical connection between a superior and inferior vertebrae while at the same time providing load bearing and permitting motion only within the nominal disc operating range or workspace. Mechanical continuity is realized by a kinematic chain of inseparable jointed elements.

An FSU workspace boundary is dictated by the sagittal, lateral and axial angle limits reported in the literature (Mow V. C. and Hayes W. C., *Basic Orthopaedic Biomechanics*, Lippincott-Raven Pub., N.Y., $2^{ndd}$ Addition, 1997). However, these angle limits do not reveal the underlying complexity of motion between two vertebrae in an FSU. The study by Mameren H. van, Sanches H., Beursgens J., Drukker, J., "Cervical Spine Motion in the Sagittal Plane II: Position of Segmental Averaged Instantaneous Centers of Rotation—A Cineradiographic Study", Spine 1992, Vol. 17, No. 5, pp. 467-474, demonstrates this complexity in the cervical spine, even when the motion is restricted to flexion and extension.

In light of the above observations and limitations, the subject invention is able to accommodate a broader range of motions than other designs in a distinguished way, while maintaining disc stability, intervertebral spacing, and integrity under static and dynamic loads.

BRIEF DESCRIPTION OF DRAWINGS

In order that a more precise understanding of the above recited invention can be obtained, a more particular description of the invention briefly described above will be rendered by reference to specific embodiments thereof that are illustrated in the appended drawings. It should also be understood that the drawings presented herein may not be drawn to scale and that any reference to, or implication of, dimensions in the drawings or the following description are specific to the embodiments disclosed. Any variations of these dimensions that will allow the subject invention to function for its intended purpose are considered to be within the scope of the subject invention. Thus, understanding that these drawings depict only typical embodiments of the invention and are not therefore to be considered as limiting in scope, the invention will be described and explained with additional specificity and detail through the use of the accompanying drawings in which.

While the boot can provide various advantages, as will be discussed, it is not required to be installed on the various embodiments of the subject invention in order for the components to function.

Figure 2:
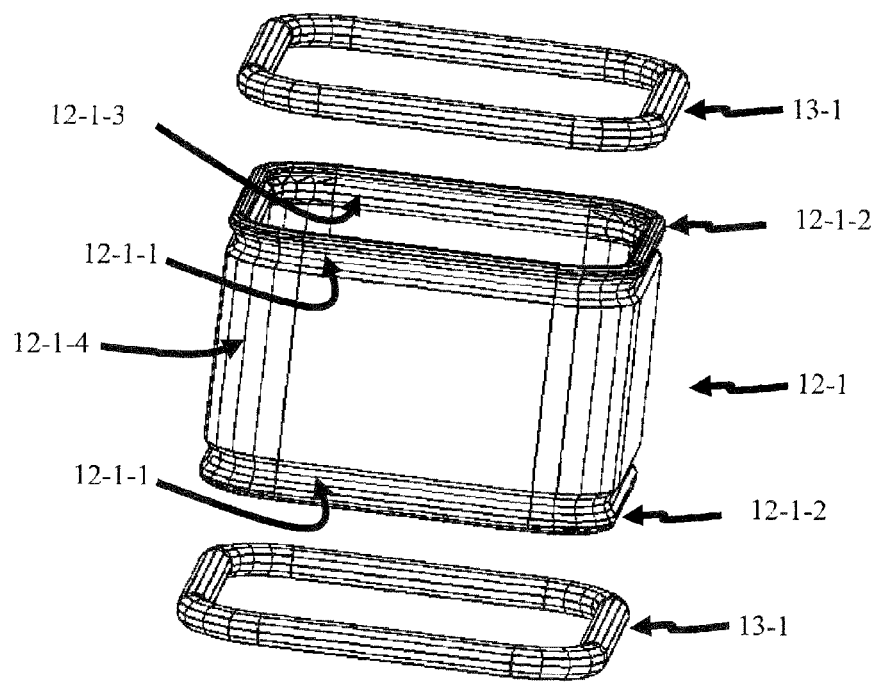

FIG. 2 illustrates an embodiment of a boot of the subject invention utilizing a tough, flexible, multi-layered, resilient, fiber-reinforced elastomer matrix 12-1 that can be firmly attached to the superior and inferior vertebral plates (9-1 and 1-1) with clamping and reinforcing elements 13-1. In this embodiment, the boot can have "beads" 12-1-2 at the top and bottom with indents 12-1-1 below the heads. The rings 13-1 can then fit into the boot indents 12-1-1 and press or hold the boot protrusion 12-1-3 into the indents 1-1-1 and 9-1-2 on the plates 1-1 and 9-1, holding beads in place. This embodiment also creates a fluid seal, sealing fluids within the device interior spaces as well as blocking fluids out of the device interior spaces. The lateral sides of the boot can be reinforced to create artificial ligaments 12-1-5 in FIG. 37. The curvate corners 12-1-4 can be more flexible than, and not necessarily as tough as, the ligament elements. In one embodiment, the anterior wall of the boot must stretch about 7-10% more than the posterior wall of the boot, so the former can be more elastic than the latter. Other methods of attaching the boot to the superior and/or inferior vertebral plates 9-1 and 1-1 can be used, such as grommets and rivets, clamping rings and other methods that fixedly attach the boot to the plates.

Figure 3:
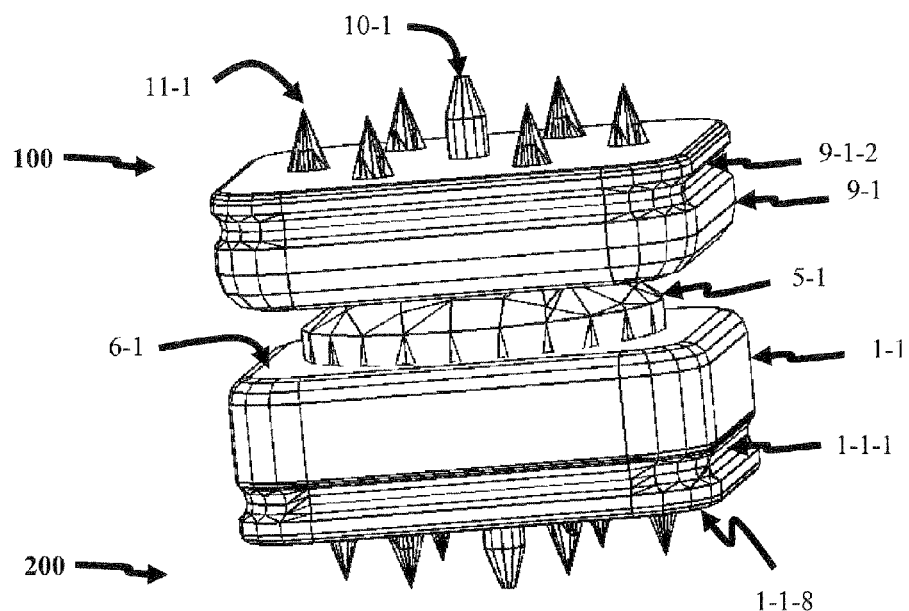

FIG. 3 illustrates an embodiment of the invention with the boot 12-1 and rings 13-1 removed. Removal of the boot reveals superior and inferior vertebral plates 9-1 and 1-1, along with the ball-cylinder 5-1 and ball-cylinder retainer 6-1.

Figure 4:
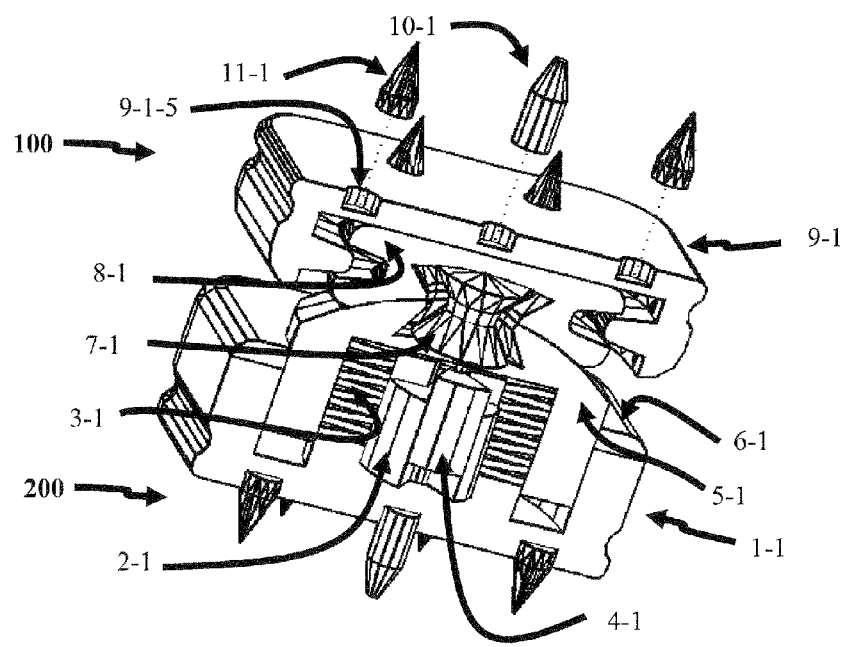
Figure 5:
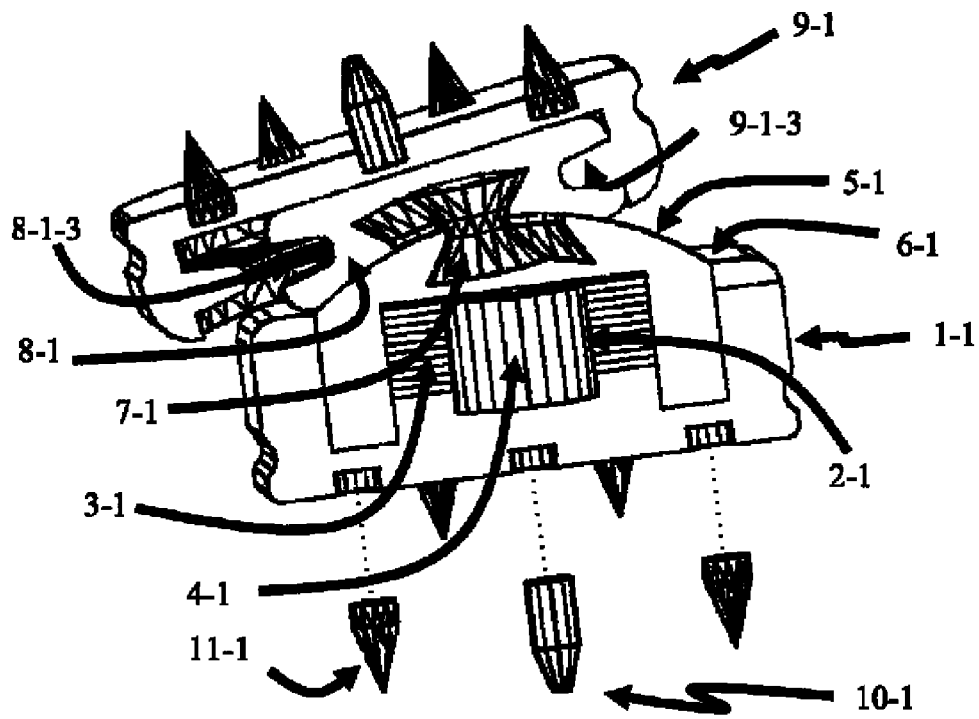
Figure 6:
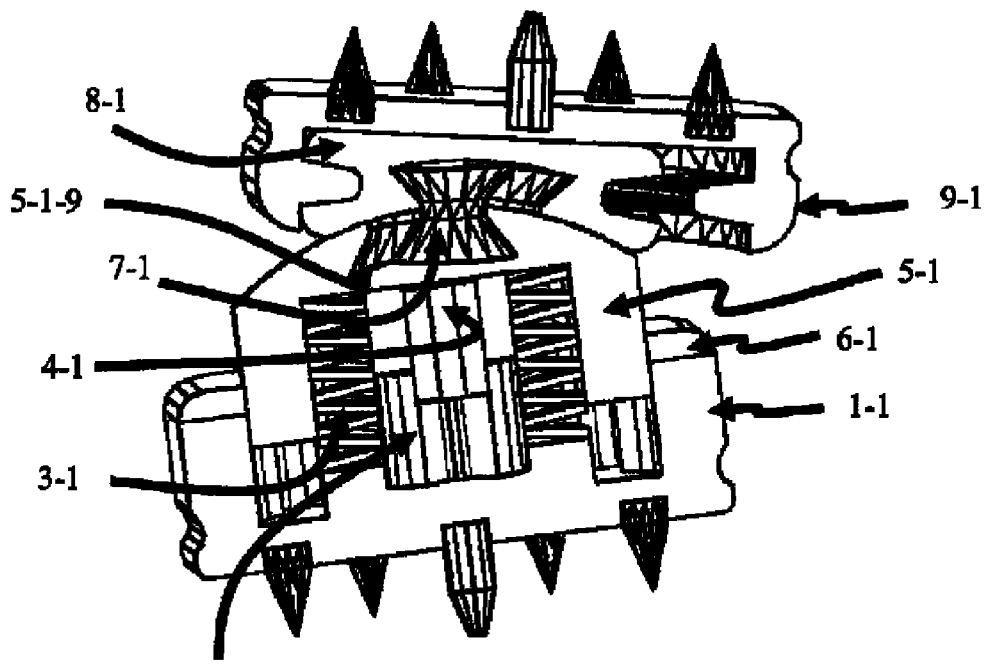

FIG. 4, FIG. 5 and FIG. 6 are tilted, perspective, cutaway views of the device in neutral, flexion, and extension positions, where the anterior part of the invention is to the left of the diagram, the posterior to the right. These figures indicate how the configurations of the various mechanical elements of the device can change as the superior vertebral plate moves with respect to the inferior vertebral plate, the former fixedly attached to a superior vertebra and the latter fixedly attached to an inferior vertebra of an FSU.

A socket 8-1, spherical slider 7-1 (not cutaway), ball-cylinder retainer 6-1, ball-cylinder 5-1, superior segmented-wall mandrel 4-1 (not cutaway), spring and cushion elements 3-1, and inferior segmented-wall mandrel 2-1 (not cutaway) assume various configurations as the FSU moves about its workspace. It should be understood that these three diagrams do not show all the possible configurations of the device, which, in principle, are limitless since the device can assume any position and orientation demanded by the 6-dimensional workspace of the FSU. At neutral and the extreme positions, indicated by these embodiments, and all other configurations within an FSU, the joint surfaces remain in contact and the device components maintain their integrity and designed operational function at all times. Springs and/or other cushioning components can provide forces antagonistic to cranial loads and boot tension during all such motions.

With this embodiment, in the neutral position, FIG. 4, the superior segmented-wall mandrel 4-1 and the inferior segmented-wall mandrel element 2-1 can be seen clearly. The spring and cushion elements 3-1 are partially compressed due to cranial loads. In this configuration of this embodiment the ball-cylinder can allow the spring element to compress even further, as seen in FIG. 5. The spring element 3-1 maintains the intervertebral height of the FSU under nominal loads. The boot 12-1 can be under tension in the neutral configuration (not shown in FIG. 4), acting antagonistically, but balanced with the spring element 3-1 restoring force and the nominal static load on the FSU. Boot tension also can resist torsion loads on the device. With regard to the embodiment shown in FIG. 4 the structure of the ball-and-socket joint, which includes socket 8-1, ball-cylinder 5-1, and the mobile spherical slider 7-1, can be seen clearly. With this embodiment, the socket 8-1 rotates about the ball's spherical surface, constrained to a portion of that spherical surface by the mobile spherical slider 7-1, which can establish joint angle rotation limits about any axis comprised of a linear combination of the sagittal and lateral axes. Rotation of the socket about the central axes of 7-1 is not constrained by the slider in this embodiment.

The multiple lower-order spherical pairs realized by the ball-and-socket joint embodiment can also be realized with higher order pairs employing ball bearings or ring bearings on those same spherical surfaces. In fact, all the lower-order pair joints instructed herein can be implemented with higher-order pairs utilizing one or more of ball-bearings, roller bearings, ring bearings, and linear bearings, as instructed in by Doty in the above-mentioned U.S. patents and published applications.

In FIG. 5, where the embodiment of the device is in full flexion, spring/cushion elements 3-1 is at maximum compression and the central cylinder can descend no further into the cavity of the inferior vertebral plate 1-1. Mobile spherical slider element 7-1, has rotationally slid to its maximum anterior position along conforming multi-spherically-surfaced cavities in the ball, pushed there by socket 8-1, which, in turn, has been pushed anteriorly by the superior vertebral plate 9-1 by means of the posterior coupling between socket-retainer bearing 9-1-3 and socket raceway cavity 8-1-3.

In this embodiment, the mobile spherical slider keeps the ball-and-socket's conforming spherical surfaces from separating for all nominal rotations of the superior vertebral plate with respect to the inferior vertebral plate, and can limit the ball-and-socket rotation angles, i.e. establish rotation angle joint stops. A mobile spherical slider can allow more than just flexion or extension, however. The spherical surfaces of the slider, ball and socket can conjointly allow complete three degrees of rotational freedom.

In a cervical embodiment, FSU flexion can cause the superior vertebral plate 9-1 to slide between approximately 1 mm and approximately 2 mm towards the anterior of the inferior plate engaging raceway cavity 8-1-3 in the socket 8-1 at an extreme penetration. At its extreme range in flexion, further motion of 9-1 is typically opposed by constraints established all along a kinematic chain from 9-1 to the inferior vertebral plate 1-1. In one embodiment, seen for example in FIG. 6, 9-1 engages 8-1, which engages 7-1, which engages 5-1, which engages the cavity walls and floor of 1-1. In this configuration, spring and cushion elements 3-1 are able to oppose compression and will restore the device configuration to the appropriate intervertebral spacing when the cranial load reduces to that associated with the neutral position of the FSU.

FIG. 6 shows a partial cutaway of an embodiment of the invention in a fully extended position. The anterior part of the invention is at the left of the diagram, the posterior on the right. In this view of the embodiment, the spring element 3-1 is at maximum expansion and no longer exerts a cranially directed force. In this configuration, the boot 12-1 will usually be under maximum tension on the anterior side (left side of the diagram) and under nominal tension on the posterior side (right side of the diagram). In a cervical embodiment, FSU extension can cause the superior vertebral plate to move between approximately 1 mm and approximately 2 mm towards the posterior.

During planar movement of superior vertebral plate 9-1 with respect to socket 8-1, a rounded-corners square socket-retainer bearing 9-1-3 (FIG. 13) engages circular raceway cavity 8-1-3 (FIG. 12), and, at extreme displacement of 9-1, the edge of the rounded-corners square socket-retainer bearing 9-1-3 inserts to maximum depth within the circular bearing raceway cavity 8-1-3. During the motion, rounded-corners square socket-retainer bearing 9-1-3 retains the socket 8-1 within the superior vertebral plate cavity 9-1-6. The planar pair joint established by the pair of surfaces (9-1-1, 8-1-1) is the first joint in an unbroken kinematic chain from superior vertebral plate 9-1 to the inferior vertebral plate 1-1.

Figure 7:
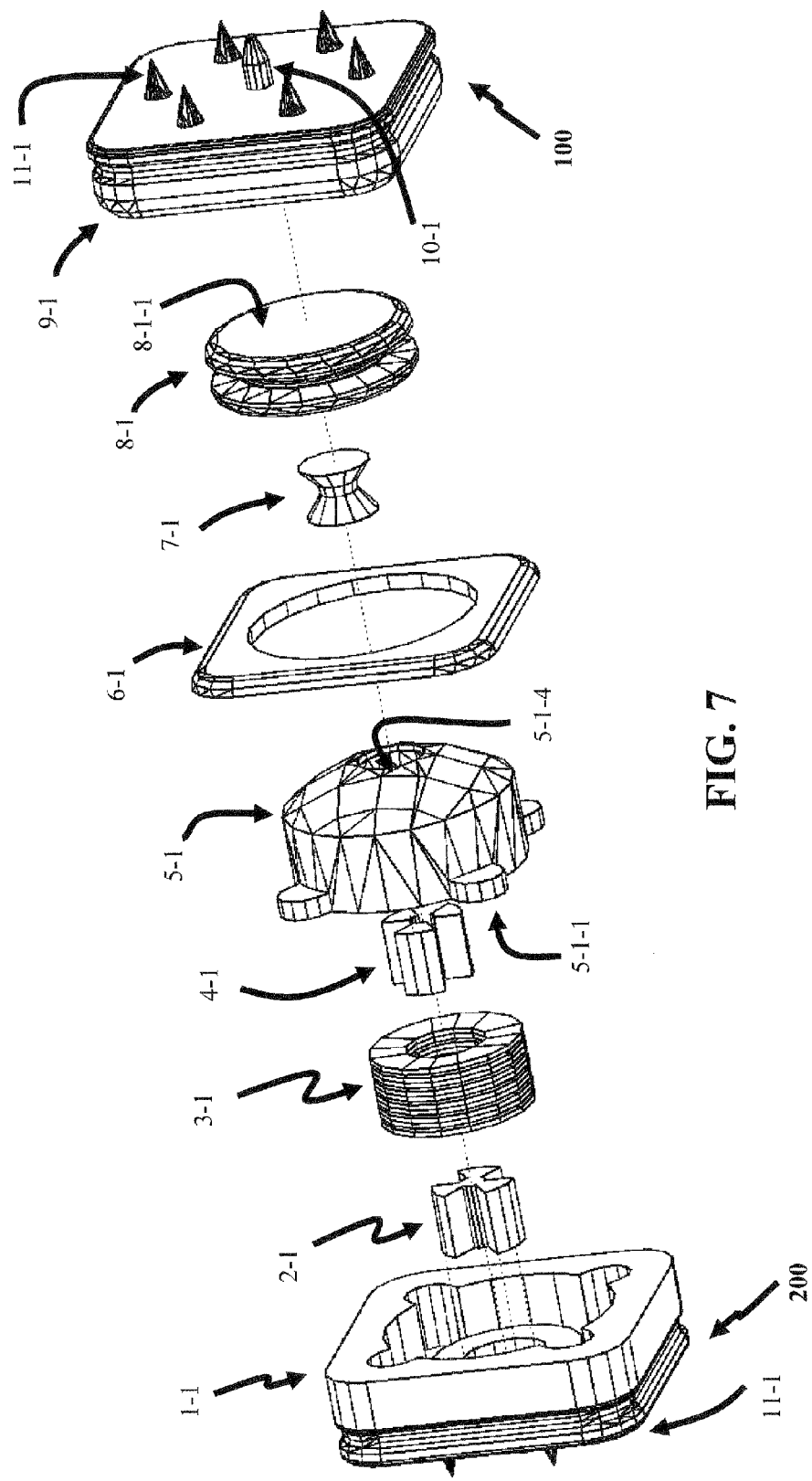
Figure 12:
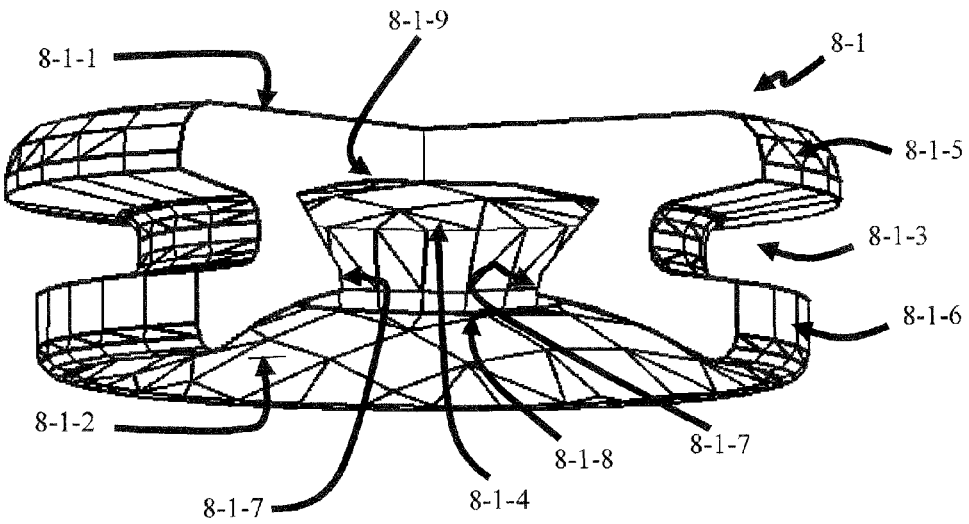
Figure 13:
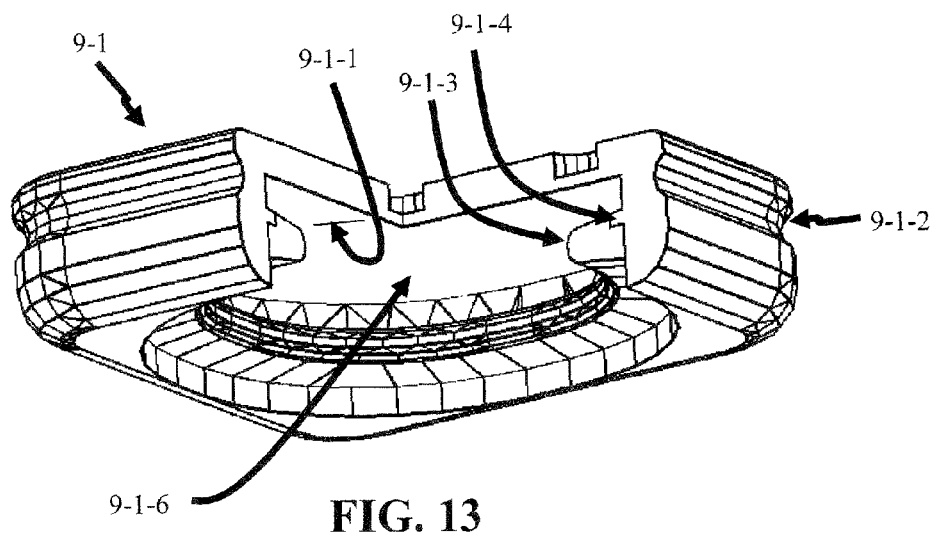

FIG. 7 shows an exploded, three dimensional view of a particular embodiment of the invention without the boot. From left to right there is: an inferior vertebral plate 1-1 with mounting fusion spikes 11-1 (central guide pin 10-1 cannot be seen in this view); an inferior segmented-wall mandrel 2-1, which fixedly attaches to the inferior vertebral plate 1-1 or can be manufactured as part of 1-1; spring and/or cushion elements 3-1, which can be stacked Belleville springs in combinations of series and parallel configurations with or without other cushioning elements, such as, for example, various types of gel, rubber, silicone, polyurethane, or other elastic materials; a superior segmented-wall mandrel 4-1, which fixedly attaches to upper surface 5-1-5 of the ball-cylinder element 5-1 (FIG. 10), or can be manufactured as part of 5-1; a ball-cylinder retainer 6-1 that fixedly attaches to the upper wall surface 1-1-6 of 1-1 (FIG. 8) and stops the withdrawal of the ball-cylinder 5-1 from the inferior vertebral plate 1-1 when projection tabs 5-1-1 at the four corners of 5-1 engage or interfere with 6-1 as they slide up to the top of conforming cavities 1-1-3 in the inferior vertebral plate; a spherical slider element 7-1, whose more caudal end inserts into cavity 5-1-4 and is held within the cavity by the cranial edge surfaces 5-1-7 (as seen, for example, in FIGS. 10 and 18) of the ball-cylinder 5-1 and whose cranial end inserts into socket cavity 8-1-4 (FIG. 12) of socket 8-1 and is held within the cavity by the cuadal edge surfaces 8-1-7, shown, for example, in FIG. 12; and a socket 8-1 which forms a planar joint with superior vertebral plate 9-1 and is retained therein by socket-retainer bearing 9-1-3 (FIG. 13).

Figure 8:
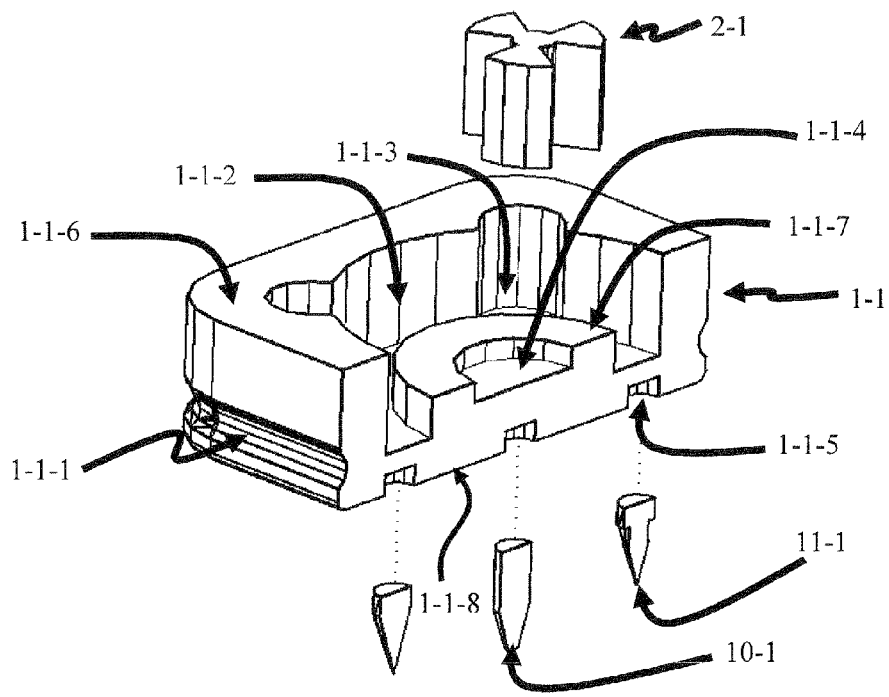

FIG. 8 shows structural elements of one embodiment of an inferior vertebral plate 1-1 in a three-dimensional cutaway view. In this embodiment, the central guide pin 10-1 and fusion spikes 11-1 on the underneath surface are fixedly attached to 1-1 in cavities 1-1-5 or can be manufactured as part of 1-1. The cavity 1-1-2 can allow axial sliding of the ball-cylinder wall 5-1-3 (FIG. 10) into the inferior vertebral plate 1-1, thus establishing a prismatic pair. Tabs 5-1-1 of the ball-cylinder slide vertically within tab cavities 1-1-3 and can also serve as joint stops when engaged with ball-cylinder retainer 6-1, which fixedly attaches to upper wall surface 1-1-6. Tabs 5-1-1 also prevent axial rotation of the ball-cylinder within cavity 1-1-2. The segmented inferior mandrel 2-1 is fixedly inserted into cavity 1-1-4 or can be manufactured as part of the inferior vertebral plate 1-1. At maximum compression, the superior segmented-wall mandrel fits into that portion of cavity 1-1-4 not occupied by the inferior segmented-wall mandrel.

Spring and/or other cushioning elements 3-1 can rest on an elevated surface or platform 1-1-7. Indent 1-1-1 is provided for boot clamping element 13-1 to hold the boot 12-1 securely to 1-1. The boot attachment method herein is only one of many techniques for attaching the boot to the vertebral plates. In an alternative embodiment, the boot edges can be pinned into, or otherwise secured to, the vertebral plates. By way of a non-limiting example, the boot edges can be secured with titanium pins inserted through titanium or flexible polyurethane or other bio-inert elastomer grommets along the periphery of the boot.

Figure 9:
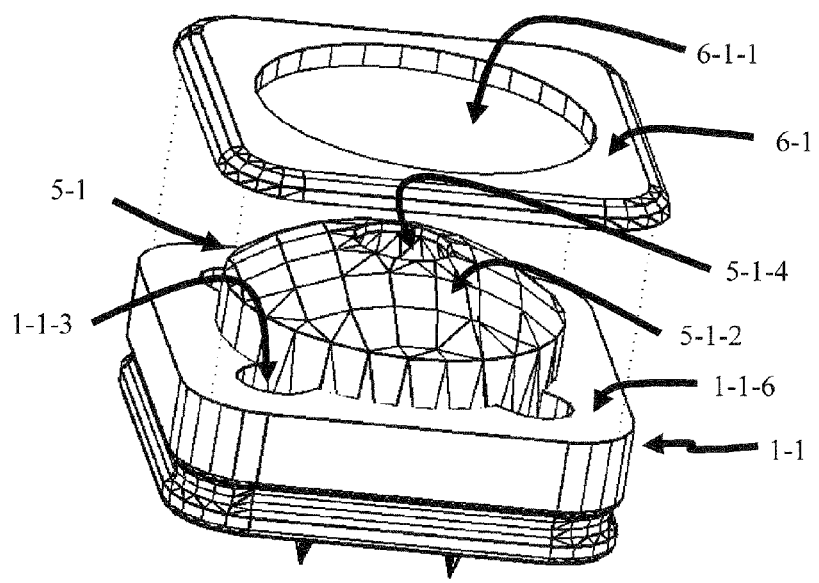

FIG. 9 shows an embodiment wherein the ball-cylinder is inserted into the inferior vertebral plate with the retainer element 6-1 poised to slide over the ball-cylinder 5-1, by means of opening 6-1-1, and fixedly attached to the inferior vertebral plate 1-1 onto inferior plate surface 1-1-6. Since retainer 6-1 blocks the top openings to cavities 1-1-3, the ball-cylinder is prevented from being extracted by interference between retainer 6-1 and tabs 5-1-1. The height of 1-1-3 that exceeds the thickness of 5-1-1 determines the range of travel of the axial prismatic joint formed by the inferior vertebral plate with the ball-cylinder. In a further embodiment, by varying the thickness of tabs 5-1-1, the tabs themselves can be spring/cushion elements. In a still further embodiment, the introduction of spring/cushion elements inserted into column cavities 1-1-3, allow this range to be mechanically programmed.

Figure 10:
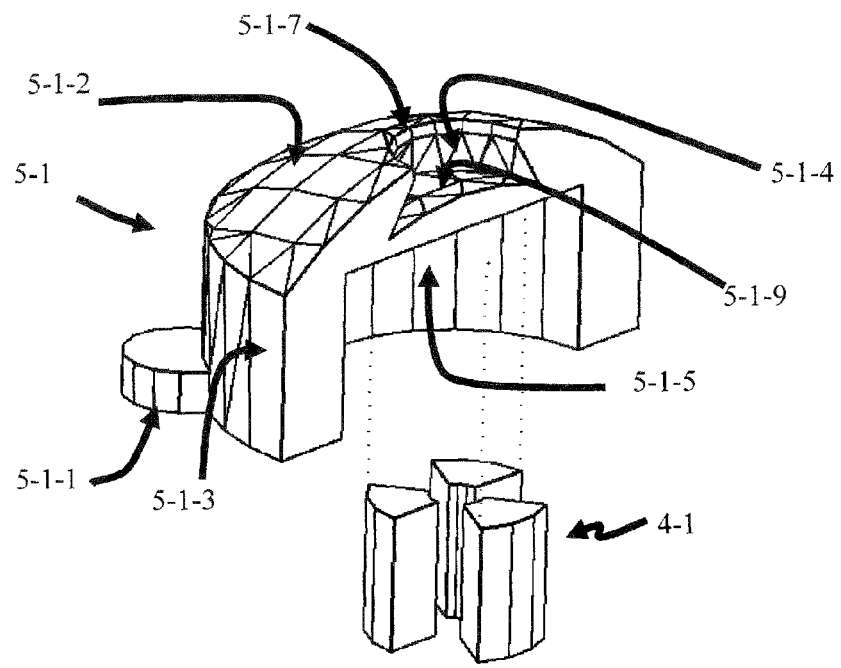

FIG. 10 illustrates a three-dimensional cutaway view of an embodiment of a ball-cylinder 5-1 and an uncut, three-superior segmented-wall mandrel 4-1, which can be fixedly attached to the superior surface of cavity 5-1-5 or can be manufactured as an integral part of 5-1. The ball portion 5-1-2 of the ball-cylinder is, in this embodiment, integrated with the cylinder portion 5-1-3, but, in an alternative embodiment, the two elements can be constructed separately and then fixedly attached to each other to realize the ball-cylinder 5-1. While 5-1-3 is shown as cylindrical, 5-1 can have any of a variety of shapes, including but not limited to, curvate, elliptic, or multi-segmented polygon shaped walls, depending upon the desired geometry of the spring element. In one non-limiting example, a ball-cylinder with an elliptical eccentricity cross section will not rotate about its central axis, even without the use of tabs. In this example, the tabs can still function as prismatic joint stops for this and other geometries. A person with skill in the art would be able to design any of a variety of ball cylinder shape configurations usable with embodiments of the subject invention. Such designs and modifications are considered to be within the scope of this invention.

Tabs 5-1-1, in conjunction with the ball-cylinder retainer 6-1, can function both as an axial prismatic joint stop and a means to interlock the ball-cylinder 5-1 and the inferior vertebral plate 1-1 without affecting the designed range of motion of the axial prismatic joint realized by those elements. Tabs 5-1-1 can also prevent a circular cross section ball-cylinder from rotating about its central axis. Eccentric cross section ball-cylinders usually will not rotate axial in their sockets and so this latter function of tabs may not apply to all situations. In one embodiment, a mobile spherical slider 7-1 fits into the spherical cavity 5-1-4. The perimeter of the base concave spherical surface 7-1-5 (FIG. 16B) of the spherical slider 7-1 is larger than the opening of cavity 5-1-4 (FIG. 9) in the ball-cylinder so that it cannot be withdrawn after assembly. In a further embodiment, the caudal spherical sliding surfaces 7-1-5, 7-3-5, 7-4-5, 7-7-5 can contact, slide against or otherwise move in relation to the cranial sliding surface 5-1-9 in the ball-cylinder spherical cavity 5-1-4.

Several techniques for assembly can be visualized by one skilled in the art. By way of a non-limiting example, the ball-cylinder can be manufactured into halves, the spherical slider placed between the halves, and the two halves fixed together, enveloping the spherical slider within the two halves of cavity 5-1-4. Other techniques can be used such as, for example, creating a geometrically keyed cutaway into the cavity opening to allow passage of concave spherical surface 7-1-5 at a specific angle and orientation not easily produced by the motion of the ball-and-socket joint, thereby effectively chaining the ball and socket together. Similar techniques can be used to insert the cranial convex spherical surface 7-1-1 into cavity 8-14 of the socket 8-1 (FIG. 12). The particular design of 7-1 allows this latter type insertion to be applied first to the socket and then to the ball, completing the assembly.

Figure 11:
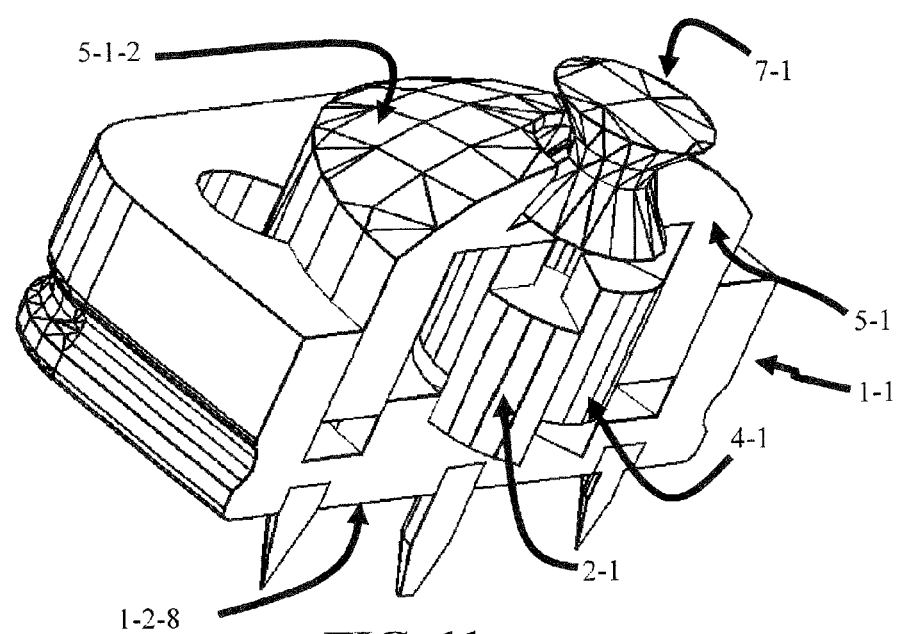

FIG. 11 is a cutaway view of an embodiment of a ball-cylinder 5-1 within an inferior vertebral plate 1-1. In this embodiment, the spherical slider 7-1, which is not cutaway, has been inserted into the spherical cavity 5-1-4 as instructed in the previous examples. A superior three-segmented-wall mandrel 4-1, uncut in the diagram for clarity of exposition, can also be fixedly attached to, or be manufactured as a part of, the ball-cylinder cavity ceiling, or equivalently, be fixed centrally to the "underneath" planar part of the spherical section that comprises the "ball", or spherical portion, of the ball-cylinder assembly.

An inferior three-segmented-wall mandrel 2-1 within cavity 1-1-4, also uncut for clarity, can also be fixedly attached to, or be manufactured as a part of, 1-1. The cylinder is displayed here in the neutral position and has not fully descended into cavities 1-1-2 and 1-1-3 of 1-1. Consequently, the wall segments of the inferior and superior mandrels 2-1 and 4-1 only partially mesh, but they are always free to slide past one another as the cylinder moves "up and down" its central axis.

FIG. 12 illustrates an embodiment of a socket 8-1 with a quadrant cut away. In this embodiment, superior surface 8-1-1 can be planar and the inferior surface 8-1-2 can be concave spherical with the same radius and center of curvature as ball surface 5-1-2 of the ball-cylinder. The caudal sliding surface 8-1-9 can have a radius and center of curvature compatible with the spherical sliding surface of a spherical slider. Curvate raceway cavity 8-1-3, which is circular in a particular embodiment, has an upper and lower lip 8-1-5 and 8-1-6. The maximum width of lower raceway lip 8-1-6 can be less than the minimum width of opening 9-1-3-2 of socket-retainer bearing 9-1-3 (FIG. 14) so that it can easily pass through that opening. The minimum width of upper raceway lip 8-1-5 can be greater than the maximum width of opening 9-1-3-2 of socket-retainer bearing 9-1-3 so that it cannot pass through that opening. Socket cavity 8-1-4 can accommodate a mobile spherical slider 7-1 or convex spherical slider 7-5 (FIG. 33).

FIG. 13 indicates the key structures of one embodiment of a superior vertebral plate 9-1, here shown as a rounded-corners square shape. The planar surfaces 9-1-1 and 8-1-1 can be a planar pair joint which can be held together by socket-retainer bearing element 9-1-3, which press fits or welds into the superior vertebral plate cavity 9-1-6 and seats against retainer stop 9-1-4 after insertion of 8-1. Indent 9-1-2 allows clamping the superior part of the boot to the superior vertebral plate.

Figure 14:
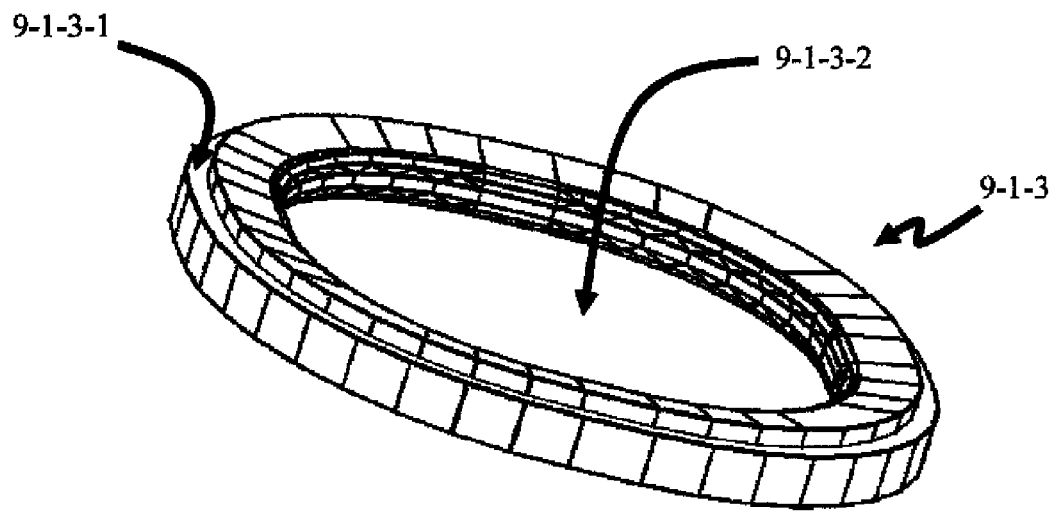

FIG. 14 illustrates an embodiment of a rounded-corners square socket-retainer bearing 9-1-3 that can act both as bearing and a retaining element for establishing and maintaining a kinematic linkage between the superior vertebral plate 9-1 and the socket 8-1 (8-6). As stated above, opening 9-1-3-2 can allow socket lip 8-1-6 to clear the opening, but causes socket lip 8-1-5 to interfere with the socket-retainer bearing element, resulting in the socket being retained within cavity of 9-1 after assembly. Socket-retainer bearing shoulder 9-1-3-1 can also rest against retainer stop 9-1-4 within the cavity of 9-1. In alternative embodiments, the contour of opening 9-1-3-2 can be curvate, elliptical, circular, or polygonal. The contour of socket-retainer bearing opening 9-1-3-2 controls the limits of motion for the socket in the planar pair joint and can be designed to create complex motion constraints.

Figure 15:
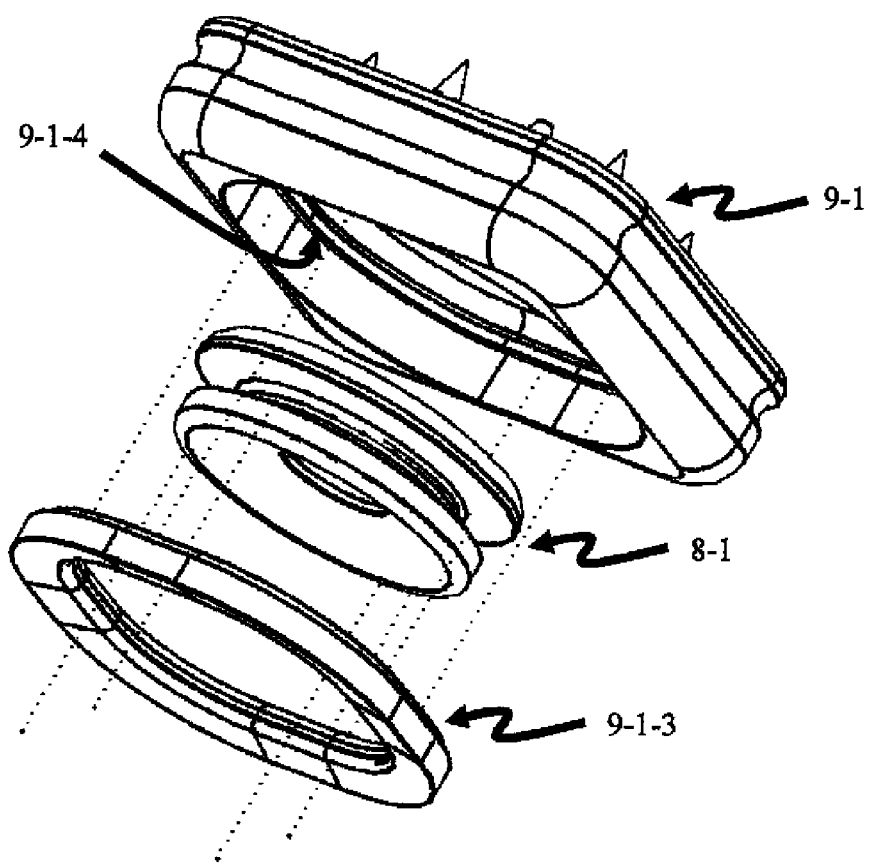

FIG. 15 shows an embodiment of the assembly of a socket into the cavity of an embodiment of the superior vertebral plate 9-1 to form a planar pair joint. Element 9-1-3 can be press fitted, or welded, up against retainer stop 9-1-4 within cavity 9-1 after insertion of the socket 8-1. Socket-retainer bearing 9-1-3 passes by lower lip 8-1-6 during the press fit without interference with 8-1. Socket-retainer bearing 9-1-3 can prevent upper socket lip 8-1-5 from passing through opening 9-1-3-2. Thus, interference forces that can result between the upper lip 8-1-5 and the socket-retainer bearing 9-1-3 hold the planar joint together by restricting axial motion of the socket in the caudal direction. After assembly, socket-retainer bearing 9-1-3 engages socket raceway cavity 8-1-3 and can permit the socket 8-1 to move freely about the planar surface 9-1-1 within the superior vertebral plate 9-1.

In the case of a cervical sized embodiment, the maximum distance the socket can move from its center position in the plane of 9-1-1 can be between approximately v2 mm and approximately 2v2 mm, i.e., between approximately ±1 mm to approximately ±2 mm in the x-direction and between approximately ±1 mm to approximately ±2 mm in the y-direction of a Cartesian coordinate system, centered in the planar surface 9-1-1. In alternative embodiments, the planar pair joint (9-1-1, 8-1-1) can also be realized with higher order pairs using, for example, ball bearings, as instructed by Doty in U.S. Pat. Nos. 7,361,192, 7,799,080, and 7,927,375, as well as U.S. Patent application no. US2010/0324688A1 and Published PCT Application No, PCT/US2010/37721, which are hereby incorporated by reference.

Figure 16A:
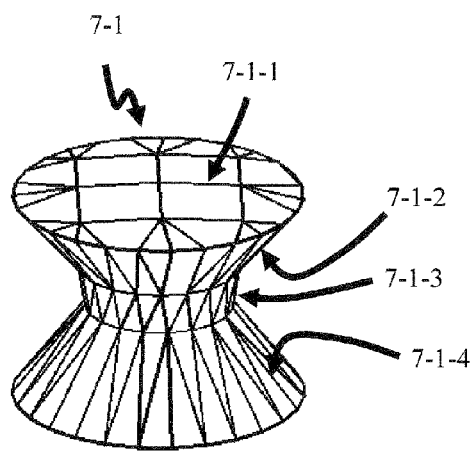
Figure 16B:
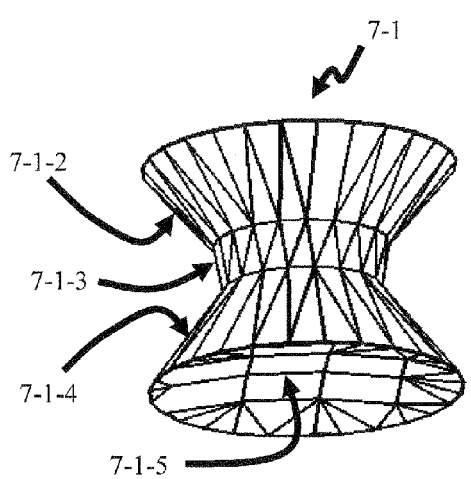

FIGS. 16A and 16B show details of an embodiment of a mobile spherical slider 7-1. In this embodiment, the boundaries of the spherical sliding surfaces 7-1-1 and 7-1-5 are circles. The boundary extents of the end surfaces 7-1-1 and 7-1-5 are such that they cannot pass through a spherical pair's cavity openings without interfering with the edges of those openings. Lateral curvate surfaces 7-1-2, 7-1-3, and 7-1-4 can pass through those same openings without hindrance and can stop the slider from further motion in a particular direction when one of those surfaces contacts an edge opening. The vertical cross section of a spherical slider can have a general curvate shape, as illustrated by the variety of examples in FIG. 16, FIG. 17A and FIG. 17B, FIG. 19A and FIG. 19B, and FIG. 21A and FIG. 21B. The caudal and cranial ends can be larger than their cavity openings and their joining structure ("stem") can be constricted to allow a limited range of movement of the slider within those openings.

FIGS. 17A and 17B detail an alternative embodiment of a mobile spherical slider 7-3. The boundaries of the spherical sliding surfaces 7-3-1 and 7-3-5, in this embodiment, are non-planar, curvate elliptic-like. The boundary extents of the spherical end surfaces 7-3-1 and 7-3-5 are such that they cannot pass through a spherical pair's cavity openings without interfering with the edges of those openings. Lateral curvate surfaces 7-3-2, 7-3-3, and 7-3-4 can pass through those same openings without hindrance and can stop the slider from further motion in a particular direction when one of those surfaces contacts an opening edge. Another example of this embodiment is realized by replacing the caudal and cranial ends 7-4-4 and 7-4-2 of spherical slider 7-4 in FIG. 19A and FIG. 19B with elliptically shaped versions.

FIG. 18 depicts a particular embodiment of a spherical pair, socket 8-3 and ball-cylinder 5-3. Features 8-3-1, 8-3-3, 8-3-5, and 8-3-6 can be identical in geometry and function to 8-1-1, 8-1-3, 8-1-5, and 8-1-6. In the embodiment shown here, concave spherical surface 8-3-2 has an elliptical opening facing an elliptically bounded spherical surface within slider cavity 8-3-4. Ball-cylinder features 5-3-1 and 5-3-3 can be identical in function and geometry to 5-1-1 and 5-1-3. Concave spherical surface 5-3-2 can also have an elliptical opening facing an elliptically bounded spherical surface within slider cavity 5-3-4.

FIG. 19A and FIG. 19B detail an embodiment of mobile spherical slider 7-4. In this embodiment, the boundaries of the spherical sliding surfaces 7-4-1, 7-4-5, 7-4-6 and 7-4-7 are circles and the lateral surfaces of cranial end 7-4-2, caudal end 7-4-4 and stem 7-4-3 can be spherical, conical or a more general curvate surface. This embodiment of a mobile spherical slider has, in contrast to the other spherical sliders discussed heretofore, two additional spherical sliding surfaces 7-4-6 and 7-4-7 and can couple the ball-and-socket spherical pair with tighter tolerance than the other versions. Additional contact surfaces within the cavities, the socket cavity inferior spherical surface 8-4-8 within the socket cavity and the spherical cavity superior spherical surface 8-4-9 within the spherical cavity in the ball-cylinder, can maintain operational integrity of a spherical pair with greater precision than sliders 7-1, 7-2, and 7-3. The same advantages derived from upper and lower contact surfaces at each end of a slider can be applied to spherical sliders derived from 7-4 by means of incorporating curvate boundaries other than circles, such as elliptical, for cranial end 7-4-2 and caudal end 7-4-4. The boundary extents of end spherical surfaces 7-4-1 and 7-4-7 can be such that they cannot pass through a spherical pair's cavity openings without interfering with the edges of those opening. Lateral curvate surfaces 7-4-3 can pass through those same openings without hindrance or interference and can stop the slider from further motion in a particular direction when it contacts an opening edge. Lateral surfaces 7-4-2 and 7-4-4, in this embodiment, cannot pass through cavity openings without hindrance or interference. Concave spherical surface 7-4-6 and convex spherical surface 7-4-7 can permit tighter tolerances between a spherical pair for this particular slider by engaging convex and concave cavity spherical surfaces, respectively, during all possible motions of the slider. In this embodiment, therefore, the caudal and cranial ends with lateral surfaces 7-4-4 and 7-4-2, respectively, are always partially enclosed during sliding by upper and lower spherical cavity surfaces performing as a spherical bearing raceway cavity. The advantage of this configuration is that surfaces 7-4-1 and 7-4-5 can maintain contact with their respective spherical surfaces within the socket 8-4 and ball-cylinder 5-4, as shown, for example, in FIG. 20. A further advantage is that this allows little or no separation between the socket 8-4 and ball-cylinder 5-4 during normal motion, resulting in tighter fitting components.

FIG. 20 presents a quadrant cutaway view of a particular embodiment of a ball-and-socket joint utilizing socket 8-4, mobile spherical slider 7-4 and ball-cylinder 5-4. The elements in this embodiment can be assembled into the rounded-corners square model by substituting them for the equivalent elements 8-1, 7-1, and 5-1. Changing the tabs of 5-4 to be the same as the tabs on 5-2 allows substituting these elements for 8-2, 7-2, and 5-2 of a cylindrical embodiment as well. Socket 8-4 and ball-cylinder 5-4 can accommodate mobile and convex spherical sliders of type 7-4. This particular embodiment gives another indication of the wide variations possible in spherical slider geometry, mobile or anchored, and the modifications that can be required of the socket and ball cavities to accommodate such variations. In certain embodiments, ball-cylinder 5-4, tabs 5-4-1, spherical surface 5-4-2, cylinder walls 5-4-3, ball spherical slider cavity 5-4-4 and central cavity 5-4-5 correspond functionally to 5-1, 5-1-1, 5-1-2, 5-1-3, and 5-1-5, respectively. In one embodiment, the differences between 5-4 and 5-1 are their cavities, which accommodate different mobile or convex spherical slider geometries. In certain embodiments, socket 8-4, planar surface 8-4-1, concave spherical surface 8-4-2, socket-retainer bearing raceway 8-4-3, socket spherical slider cavity 8-4-4, raceway upper lip 8-4-5 and raceway lower lip 8-4-6 correspond functionally with 8-1, 8-1-1, 8-1-2, 8-1-3, 8-1-4, 8-1-5 and 8-1-6. Also in certain embodiment, the difference between 8-4 and 8-1 can be their respective cavities 8-4-2 versus 8-1-4 that handle different shaped sliders.

In general, ball-cylinder embodiments disclosed herein include variations in cylinder contour, spherical slider cavity design, number and location of attached convex spherical sliders, and number, size, and placement of tabs. Similarly, socket embodiments disclosed herein include variations in socket contour, spherical slider cavity design, and number and location of attached concave spherical sliders.

Figures 21A, 21B:
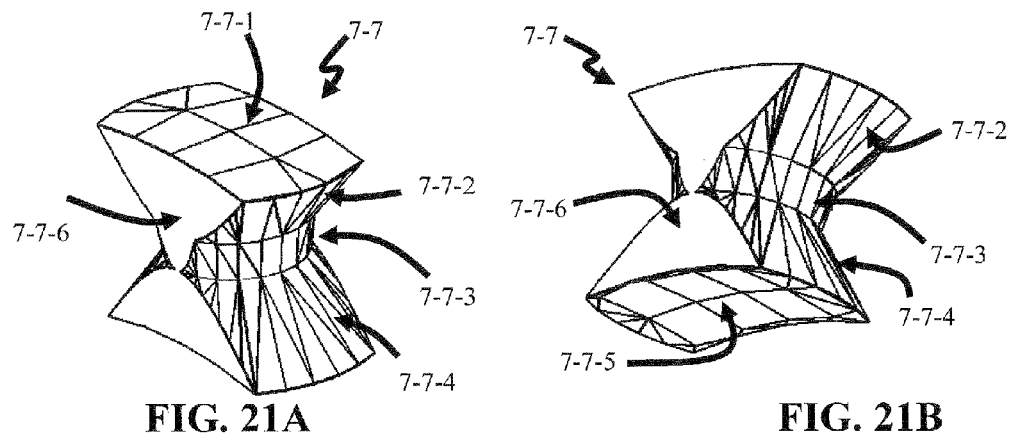

FIGS. 21A and 21B detail an embodiment of a mobile spherical slider 7-7. The boundaries of the spherical sliding surfaces 7-7-1 and 7-7-5 of this embodiment are non-planar, curvate rectangle-like. The boundary extents of the end surfaces 7-7-1 and 7-7-5 can be such that they cannot pass through a spherical pair's cavity openings without interfering with the edges of those openings. Lateral curvate surfaces 7-7-2, 7-7-3, and 7-7-4 can pass through those same openings without hindrance and can stop the slider from further motion in a particular direction when one of those surfaces contacts an edge opening. Surfaces 7-7-6 on the left and right lateral sides of the slider can be planar and realize a closed planar pair with the cavity lateral sides. In a further embodiment, sides 7-7-6 do not interfere with the cavity openings. These planar surfaces can constrain a spherical pair to rotate only about an axis perpendicular to the plane of lateral side 7-7-6, for example, in a particular embodiment the axis can be the sagittal axis (perpendicular to the sagittal plane). The joint limits of the permitted sagittal rotation in this embodiment can be determined from the angular size difference between the slider spherical surfaces and their corresponding cavity spherical surfaces. Central axis (perpendicular to the horizontal plane) and lateral axis (perpendicular to the frontal plane) rotations between the spherical pair are blocked by the planar pair lateral sides of this slider in this embodiment.

Figure 22:
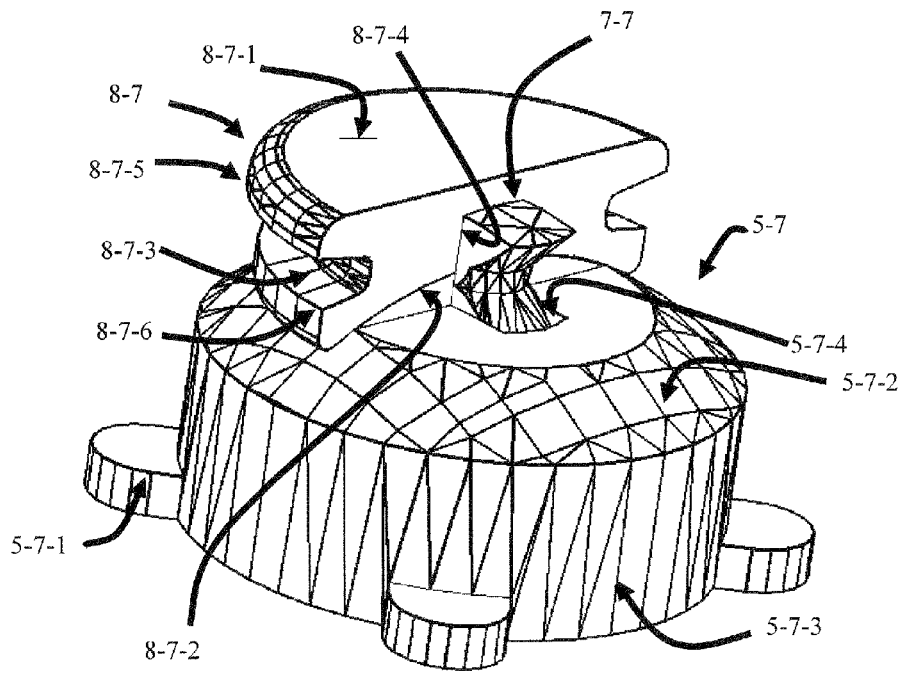

FIG. 22 illustrates the use of slider 7-7 in a ball-and-socket spherical pair (5-7-2, 8-7-2). In this embodiment, ball-cylinder 5-7 differs from 5-1 in the slider cavity, 5-7-4 versus 5-1-4. Elements 5-7-1, 5-7-2, and 5-7-3 can be the same as their 5-1 corresponding elements 5-1-1, 5-1-2, and 5-1-3. Cylinder cavity 5-7-5 is hidden and not shown in the diagram, but can be identical to 5-1-5. Socket 8-7 elements 8-7-1, 8-7-2, 8-7-3, 8-7-5 and 8-7-6 can be the same as socket 8-1 elements 8-1-1, 8-1-2, 8-1-3, 8-1-5 and 8-1-6. In this embodiment, only cavities 8-7-4 and 8-1-4 need be different to accommodate different slider geometries.

Figure 23:
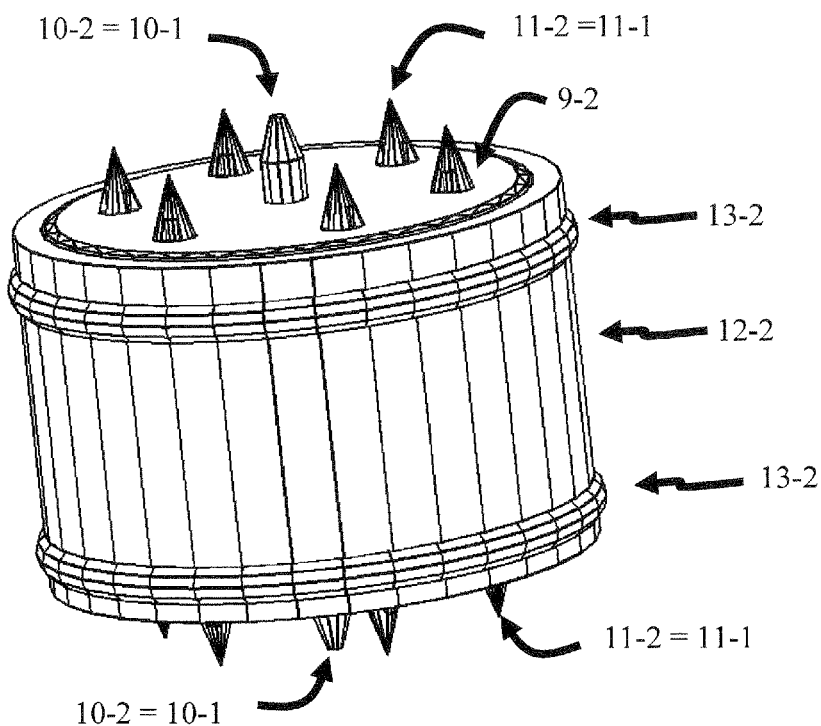
Figure 24:
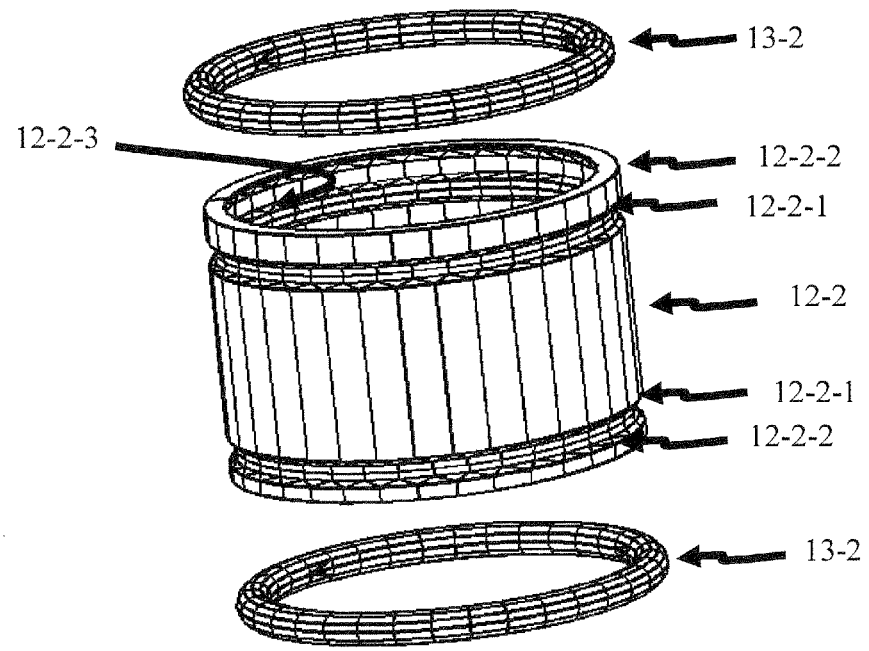

FIG. 22 through FIG. 28 illustrate a cylindrical embodiment employing the same features as the square embodiment with a few changes to accommodate the cylindrical geometry. Refer to FIG. 23 and FIG. 24. In this embodiment, circular clamping rings 13-2 replace the rounded-corners square elements 13-1; a cylindrical boot 12-2 can replace the curved rectangular boot 12-1; guide pins 10-1 and 11-1 on the inferior plate surface 1-2-8 of 1-2 and the cranial surface of superior plate 9-2 can be the same as in the rounded-corners square version, but, for systematic designation can also be 10-2 and 11-2, and, for convenience only, are indicated equivalent in these figures; circular ball-cylinder retainer 6-2 can replace the rounded-corners square retainer 6-1; and rounded-corners square superior and inferior vertebral plates 9-1 and 1-1 can be replaced by cylindrically shaped plates 9-2 and 1-2, respectively. The cylindrical embodiment can have many identical elements in common with the rounded-corners square embodiment. These identical elements are indicated by equivalencies in the designators, namely, socket 8-2, spherical slider 7-2, segmented-wall superior and inferior mandrels 4-2 and 2-2, and spring and/or cushion elements 3-2 can be equivalent to 8-1, 7-1, 4-1, 2-1, and 3-1, respectively.

Ball-cylinder 5-2 can also have more and smaller tabs than ball-cylinder 5-1, however, 5-1 can be manufactured with the same size and number of tabs as 5-2, essentially justifying the view that 5-2 is a variation of 5-1 easily determined by one skilled in the art given the instruction here.

FIG. 23 is a three dimensional view of an embodiment of the device using cylindrical geometry.

FIG. 24 shows a cylindrical boot 12-2 embodiment with indents 12-2-1, reverse bulge 12-2-3, and hard elastomer beads 12-2-2. In this embodiment, the boot clamping rings 13-2 are now circular in contrast to the rounded corner square shape of clamping rings 13-1. The corresponding functional elements in the square geometry can be, in the order mentioned, 12-1, 12-1-1, 12-1-3, 12-1-2, and 13-1.

Figure 25:
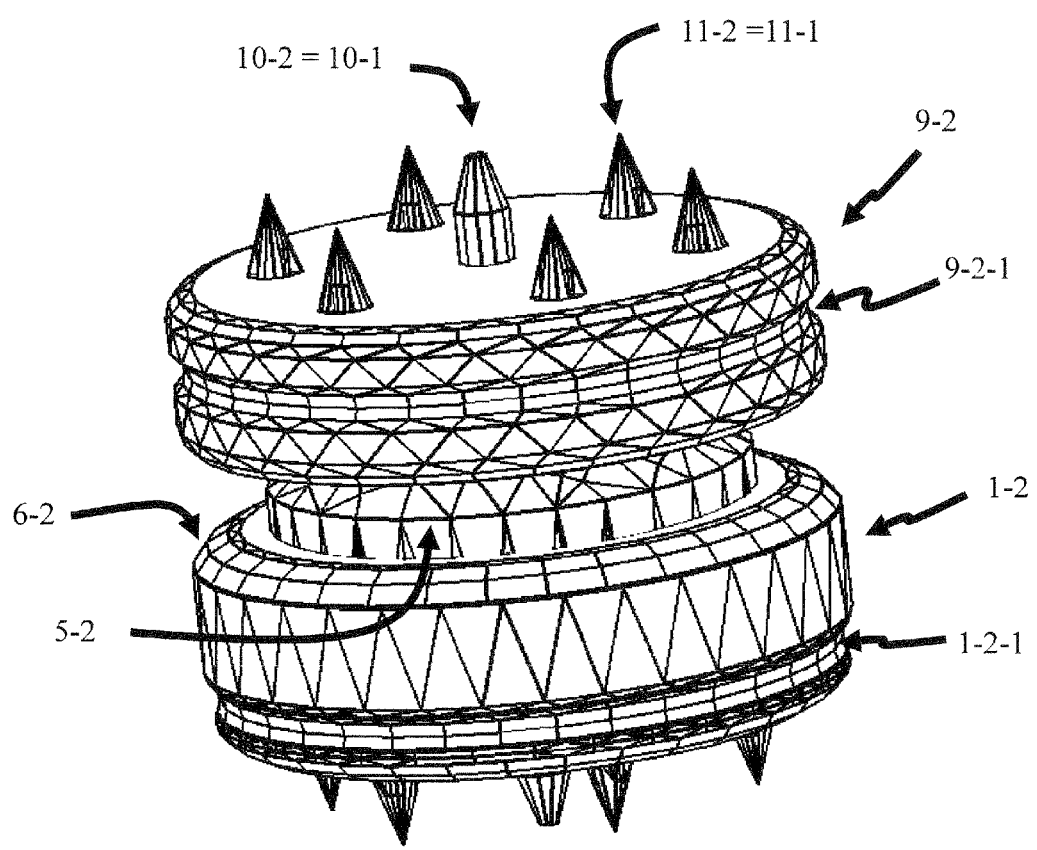

FIG. 25 illustrates an embodiment of the device without the boot. The inferior vertebral plate 1-2 can be seen as well as the superior vertebral plate 9-2 and portions of the ball-cylinder 5-2. The ring clamping indents 1-2-1 and 9-2-1 on the vertebral plates can also be noted. Element 6-2 is a circular ball-cylinder retainer.

Figure 26:
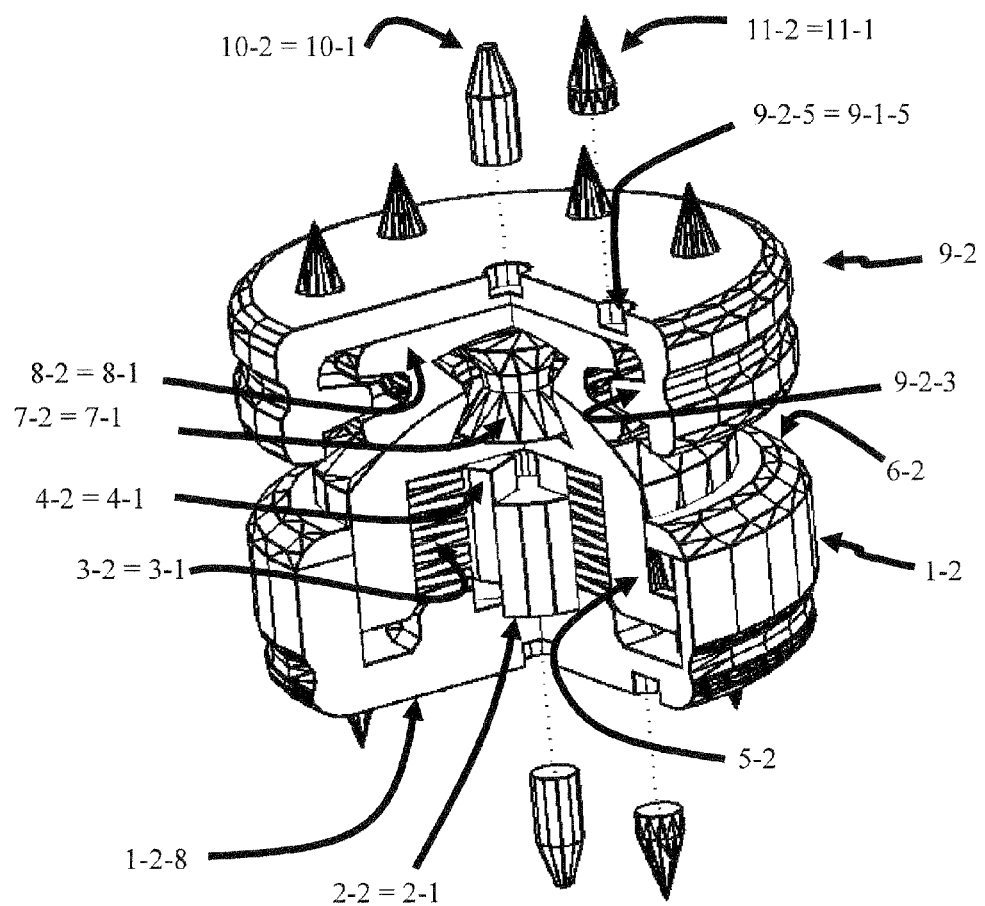

FIG. 26 is a three dimensional, quadrant-cutaway view of the cylindrical embodiment of the subject invention. The structure of this embodiment is similar to the rounded-corners square geometric device and can include the use of common parts, for example, 2-2=2-1, 3-2=3-1, 4-2=4-1, 7-2=7-1, and 8-2=8-1. In this embodiment, elements 1-2, 6-2, and 9-2 are cylindrical in shape, in contrast to the rounded-corners square elements 1-1, 6-1, and 9-1. In an alternative embodiment, the difference between 5-2 and 5-5 can be nil by use of certain design choices, so those two elements may not deviate much from one another. Fusion spikes can be screwed, welded or press fit into inferior and superior vertebral plates 1-2 and 9-2. Holes 9-2-5 can be the same as holes 9-1-5 in the rounded-corners square geometry. In other embodiments, the fusion spike and guide pin holes, however, do not have to all be the same size in either case, since the various fusion spikes and/or guide pin(s) themselves do not have to be identical in height or diameter.

Figure 27:
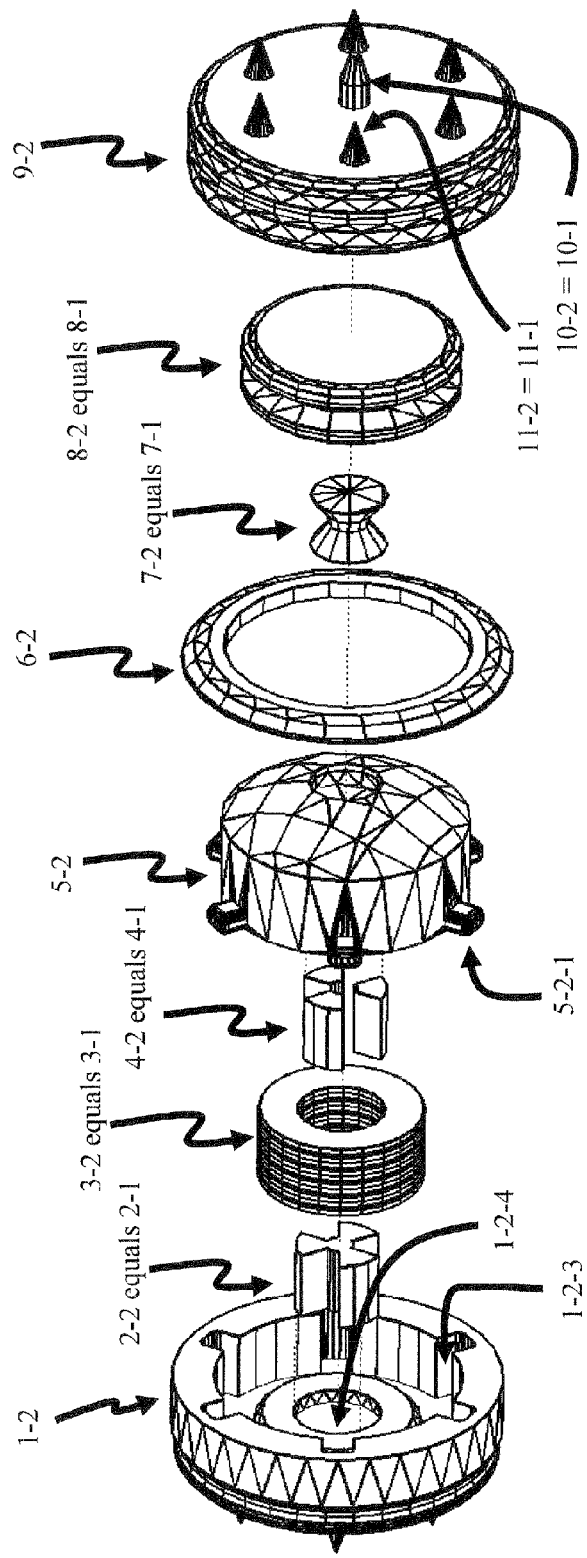

FIG. 27 is a three-dimensional exploded view of one embodiment of the device.

Elements 2-2, 3-2, 4-2, 7-2, 8-2 in the cylindrical geometry can be similar to elements 2-1, 3-1, 4-1, 7-1, 8-1, respectively, in the rounded-corners square geometry. Elements 1-2, 5-2, 6-2, and 9-2 can also differ from 1-1, 5-1, 6-1, and 9-1 primarily due to differences between rectangular to cylindrical geometry.

Figure 28:
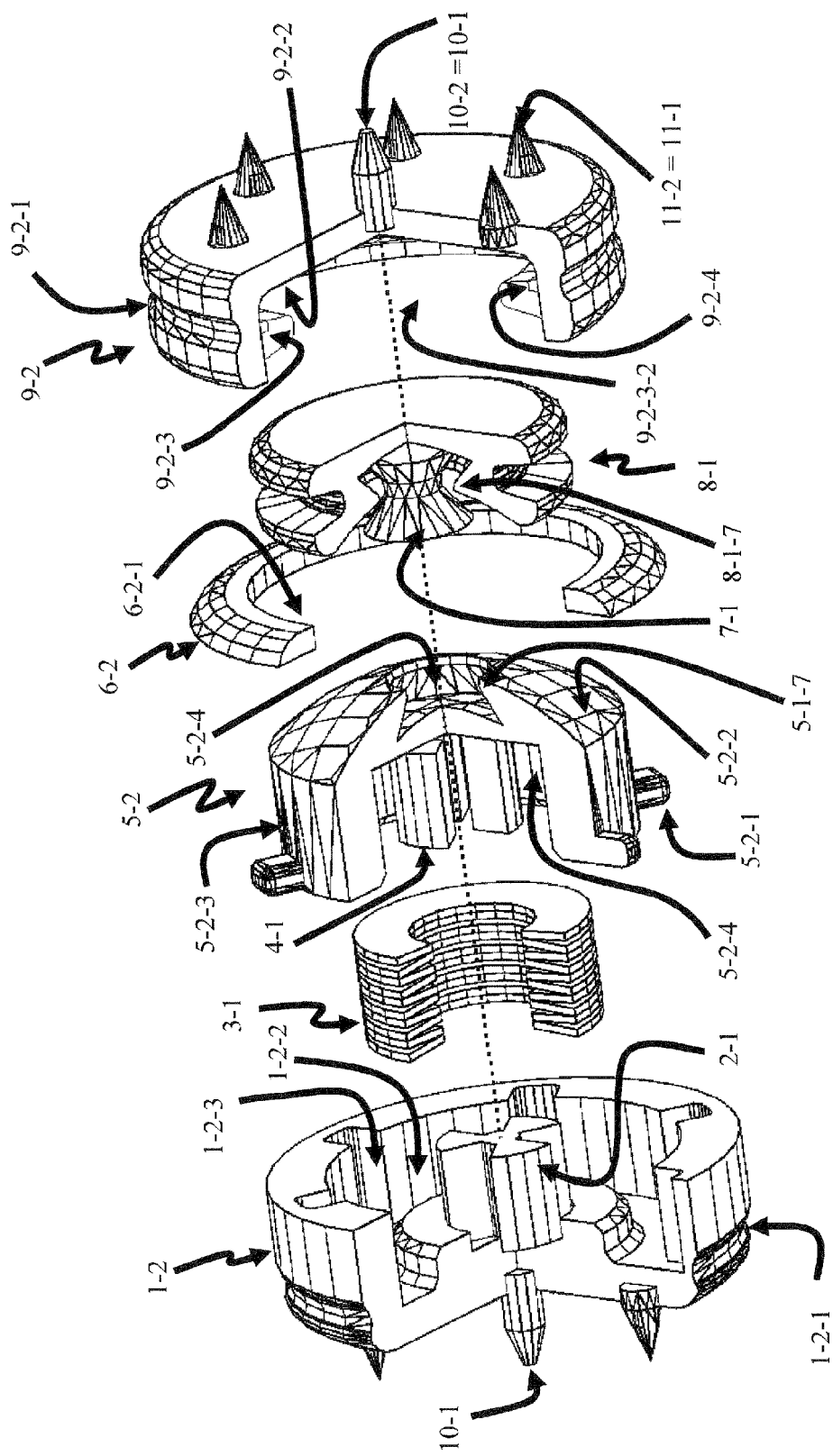

FIG. 28 provides an exploded, three-dimensional, quadrant cutaway view of a cylindrical embodiment. The inferior vertebral plate cavities 1-2-2, 1-2-3 of this cylindrical geometry embodiment correspond to 1-1-2 and 1-1-3 in the rounded-corners square geometry. The embodiment shown in this figure indicates six cavities for the six tabs 5-2-1 on ball-cylinder 5-2. The tabs 5-2-1 can be smaller. In one embodiment, the tabs 5-1-1 on the square model 5-1 can be larger and fewer in number because of the available volume in the corners, a volume typically not available in the cylindrical model. Other features on ball-cylinder 5-2, namely, 5-2-2, 5-2-3, and 5-2-4 correspond to those in the square model ball-cylinder, namely, 5-1-2, 5-1-3, and 5-1-4. The ball-cylinder 5-2 retainer ring 6-2 is circular as is the opening 6-2-1, in this embodiment. On the superior vertebral plate 9-2, the boundary of the planar joint surface 9-2-2 is circular as opposed to a rounded-corners square 9-1-1, the latter able to provide more motion capability because the corners allow equal translations in the x and y directions of the plane and the circularly bounded one generally do not. The socket-retainer bearing 9-2-3 with opening 9-2-3-2 and socket-retainer bearing stop 9-2-4 serve the same function as the corresponding rounded-corners square socket-retainer bearing 9-1-3 and stop 9-1-4. The contour of socket-retainer bearing opening 9-2-3-2 can control the limits of motion for the socket in the planar pair joint and can be designed to create complex motion constraints. The socket 8-1 (8-6) can be assembled into superior vertebral plate 9-2 in the same manner as illustrated in FIG. 15 for the rounded-corners square version.

Figure 29:
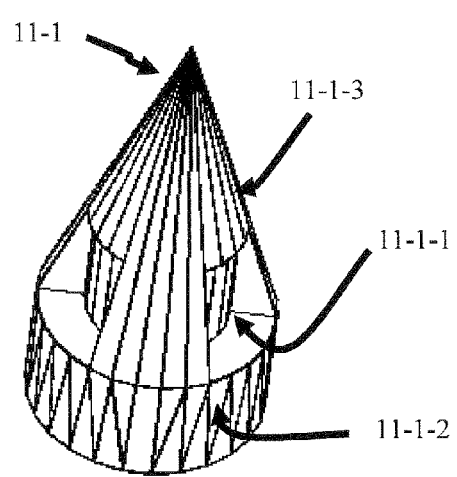
Figure 30:
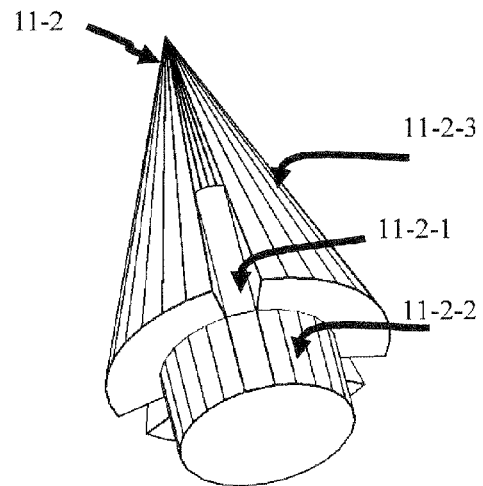

FIG. 29 and FIG. 30 illustrate two embodiments of the many geometrical shape embodiments that can be utilized for a spike. Indents 11-1-1 and 11-2-1 can promote cancellous bone growth and/or provide a means of screwing the fusion spikes into a vertebral plate, if that is the selected method of assembly. The base of the spike can be cylindrical and fully extended to support the cone as in 11-1-2 or extend under the cone as in 11-2-2. Extending the height of 11-2-2, so that the lower edge of surface 11-2-3 is above the superior (inferior) surface of the superior (inferior) vertebral plate, can create a barbed spike that can increase the binding of the superior (inferior) vertebral plate to the superior (inferior) vertebra of the FSU as the cancellous bone fills in the gap. Given the instruction here, one skilled in the art would be able to devise other geometries, indents, channels, cavities and holes in the fusion spikes that help bone fusion and such variations or equivalencies thereof are consider to be within the scope of the subject invention.

Figure 31:
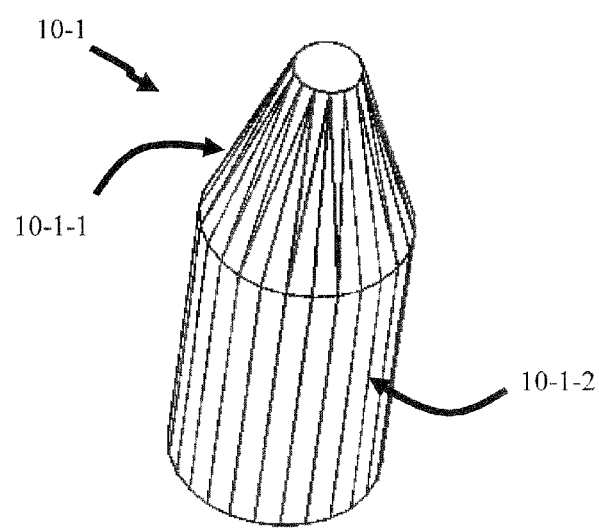

FIG. 31 portrays an example guide pin 10-1 with a frustum top 10-1 and cylindrical base 10-1-2. Given the instruction here, one skilled in the art would be able to devise other geometries and chamfers and include indents, channels, cavities and holes in the guide pin to encourage easy insertion and later bone fusion and such variations or equivalencies thereof are considered to be within the scope of the subject invention. Specialization of joint range limits and boots with non-uniform, non-symmetric performance characteristics can require special device orientation for insertion. In such cases, the center guide pin can position the invention for insertion and the fusion spikes can align the invention into an orientation required by the prescribed workspace by appropriate pilot hole drilling into the cancellous bone. More than one guide pin on each vertebral plate can also be used for the same purpose.

FIGS. 32A and 32B illustrate one embodiment of spring element 3-1 realized by a series stack of Belleville springs 3-1-1. A quadrant cutout (FIG. 32B) of 3-1-1 illustrates its nominal structure without guard lips or rings. The spring element can be stacked into a combination of series/parallel arrangements. Other spring and/or cushioning elements such as machined helical springs, wire springs, elastomers, gels, hydrophilic materials, pneumatic cushions, polyurethane, polyetheretherketone, or combinations of one or more of these elements can be used to perform a cushioning effect and oppose loads on the FSU. In a further embodiment, the Belleville springs can also employ the use of ring guards and/or guard lips to prevent inversions. Full details on spring configurations and embodiments are also disclosed in U.S. Pat. Nos. 7,361,192, 7,799,080, and 7,927,375, as well as U.S. Patent application no. US2010/0324688A1 and Published PCT Application No, PCT/US2010/37721, which are hereby incorporated by reference.

FIG. 33 depicts an example of a convex spherical slider 7-5, with slider surface 7-5-1, fixed to a convex spherical surface 5-1-4. A convex, or anchored, spherical slider, such as 7-5, like other spherical sliders disclose herein, functions both as a rotation joint stop and a spherical pair retention element. In this embodiment, the anchored spherical slider 7-5 insures that the spherical pair 5-5-2 and 8-1-2 is restricted to rotations about their common center of curvature. Limited, non-rotational displacements from the center of curvature can take place for some spherical slider geometries, but these displacements can be kept small by other geometries, such as found in 7-4 (FIG. 19A and FIG. 19B).

A convex spherical slider can be manufactured separately, or as part of the convex spherical surface to which it is affixed. The cranial end plus a portion of the midsection of each mobile spherical slider, and suggested variations, discussed here can be used as convex spherical sliders. For example, convex spherical slider 7-5, a particular embodiment with lateral surfaces 7-5-2 and 7-5-3 can be the same as 7-1-2 and 7-1-3 on mobile spherical slider 7-1. Convex spherical surface 7-5-1, which can be the same as 7-1-1, can conform to the cavity ceiling concave spherical surface in 8-1-4, which it contacts. Both of these spherical surfaces can have the same center of curvature as the ball and socket spherical surfaces.

A convex spherical slider 7-5 can also limit rotation angles of the concave spherical element about any axis, comprised of a linear combination of the sagittal and lateral axes, that passes through the ball's center by an amount dictated by the geometry of the cavity and the stop. In this embodiment, convex spherical slider 7-5 with sliding surface 7-5-1 has a circular boundary, as does the embodiment shown of roof surface of cavity 8-5-4. Such a configuration cannot limit rotation angles about the convex slider's central axis for any position of that axis on the socket's sliding spherical surface.

A convex spherical slider embodiment based on the geometry of the "elliptic" spherical slider 7-3 (FIG. 17A and FIG. 17B), along with supporting "elliptic" cavities 5-3-4 and 8-3-4 (FIG. 18) that posses a spherical sliding surface, can constrain axial rotations.

In summary, a convex spherical slider can be derived from a midsection and second, or cranial, end of any particular mobile spherical slider, where the midsection is fixed onto a convex spherical surface and the first, or caudal, end of a mobile spherical slider is not included as part of a convex spherical slider.

A convex spherical joint stop 7-5 fixed on the ball typically allows only half the rotational range of a mobile spherical slider rotational joint stop 7-1 for the same size socket cavity 8-1-4 and physical measurements on the corresponding features of the two stops.

Figure 34:
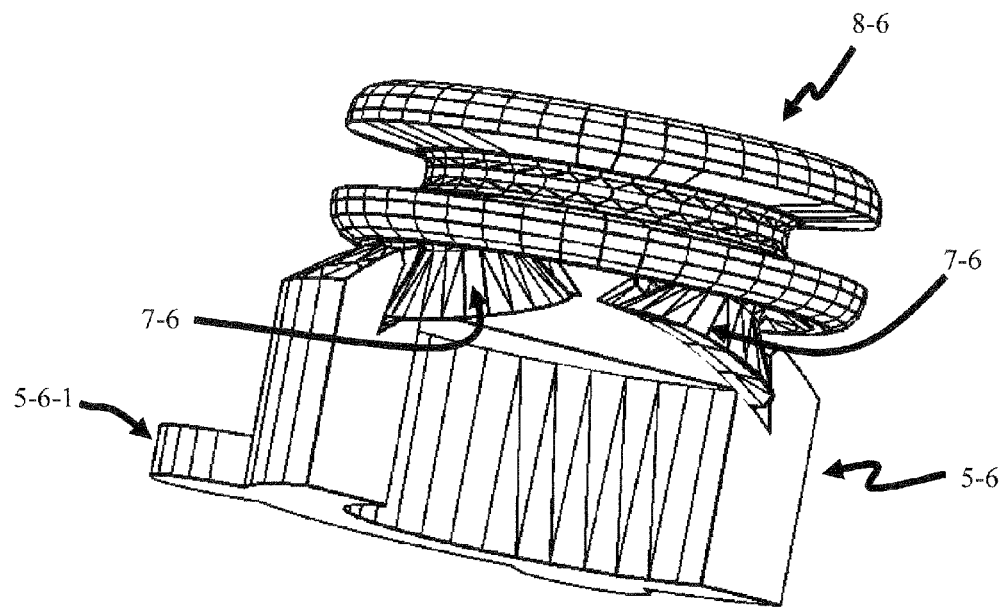

FIG. 34 shows a cutaway view of an embodiment of a ball-cylinder 5-6 with two spherical cavities suitable for the insertion of two concave spherical sliders 7-6 fixed at one end to a socket 8-6. These concave spherical sliders can be mounted on, or manufactured as part of a concave spherical surface, in this case, surface 8-6-2 of socket 8-6.

Figure 35:
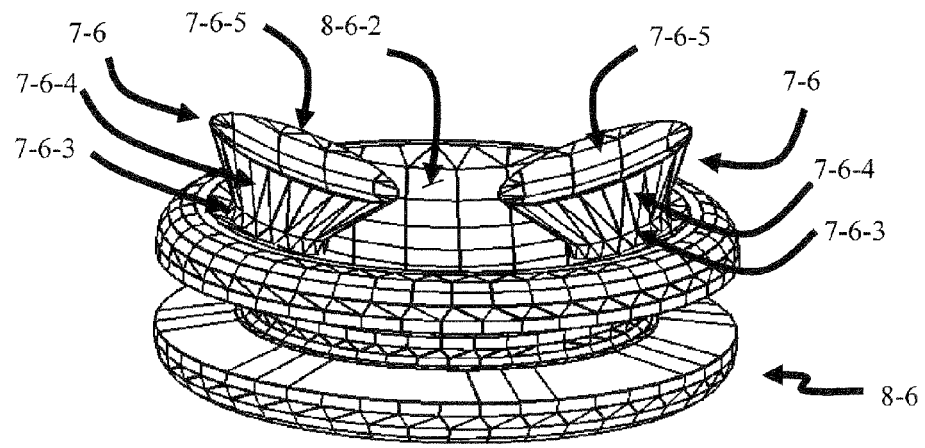

FIG. 35 illustrates an embodiment of two concave spherical sliders 7-6 that fix to a concave spherical surface such as 8-6-2 of socket 8-6, shown "upside down". Concave spherical slider 7-6, with concave slider spherical surface 7-6-5, can be manufactured as part of a concave spherical surface of a spherical pair, or fixedly attached as a separate element to such surfaces. Lateral surfaces 7-6-3 and 7-6-4 can be identical to 7-1-3 and 7-1-4 of mobile spherical slider 7-1, although the equivalent of half of the extent of 7-6-3 can be fixedly embedded into the socket surface 8-6-2. Concave spherical surface 7-6-5 can be identical to 7-1-5. Concave spherical surfaces 7-6-5, 8-6-2, and 5-6-2 can have the same center of curvature. In summary, a concave spherical slider can comprise a caudal end and midsection portion of any particular mobile spherical slider with the midsection end fixed onto a concave spherical surface.

Sagittal and lateral rotation stop limits of a socket with two anchored spherical sliders can range, for a particular embodiment, approximately ±5 degrees about neutral, or, for another embodiment with ball cavities twice as large or stops half as large or a mix of the two geometric changes, approximately ±10 degrees about neutral. Axial rotations stop limits of the socket are now constrained and can range, approximately ±14 degrees about neutral, or approximately ±28 degrees about neutral, respectively.

Figure 36:
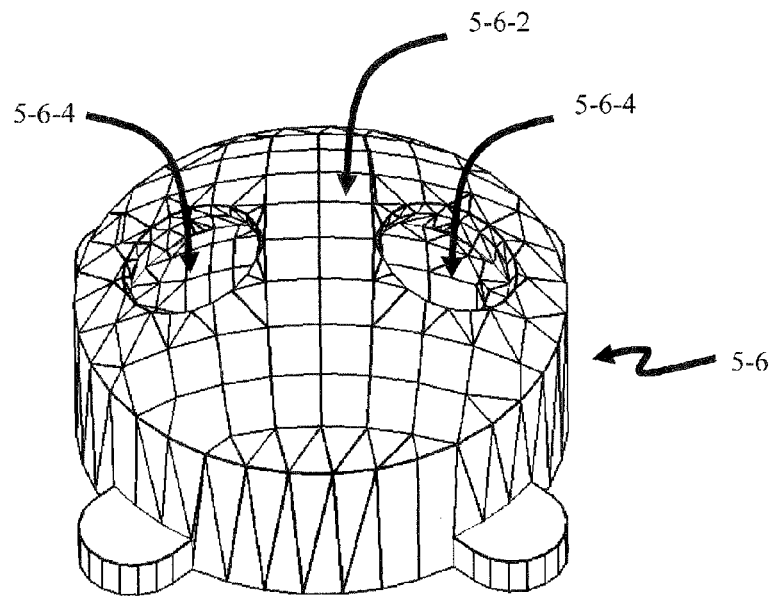

FIG. 36 depicts an embodiment of a ball-cylinder 5-6 with two cavities 5-6-4 opening out onto spherical surface 5-6-2 to accommodate two concave spherical sliders 7-6 found on socket 8-6.

Figure 37:
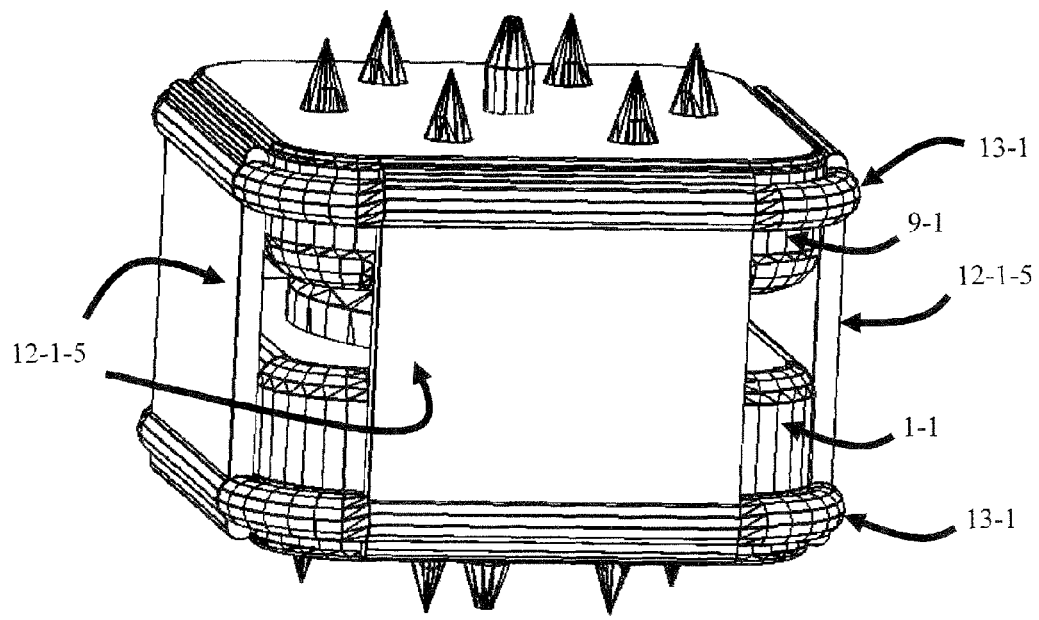

FIG. 37 discloses an embodiment of the subject invention wherein tough, flexible, ribbon-like ligament boot elements 12-1-5 can be attached separately to the superior and inferior vertebral plates 9-1 and 1-1 on four sides; the anterior, posterior, left, and right lateral surfaces. The boot ligaments can be attached with additional titanium grommets, or with flexible polyurethane or other types of elastomer grommets, and rivets along the lateral surface of the vertebral plates or with a bio-compatible, flexible adhesive for added stability and strength.

This figure can represent a separate embodiment with artificial ligaments and no enclosing boot (hence, no confinement of fluids within the invention), or as an embodiment with an enclosing boot that is not shown in order to reveal the deeper structure of the artificial ligaments, which can be covered by the boot or which can be manufactured as part of, and integrated into, the overall boot structure.

Figure 38:
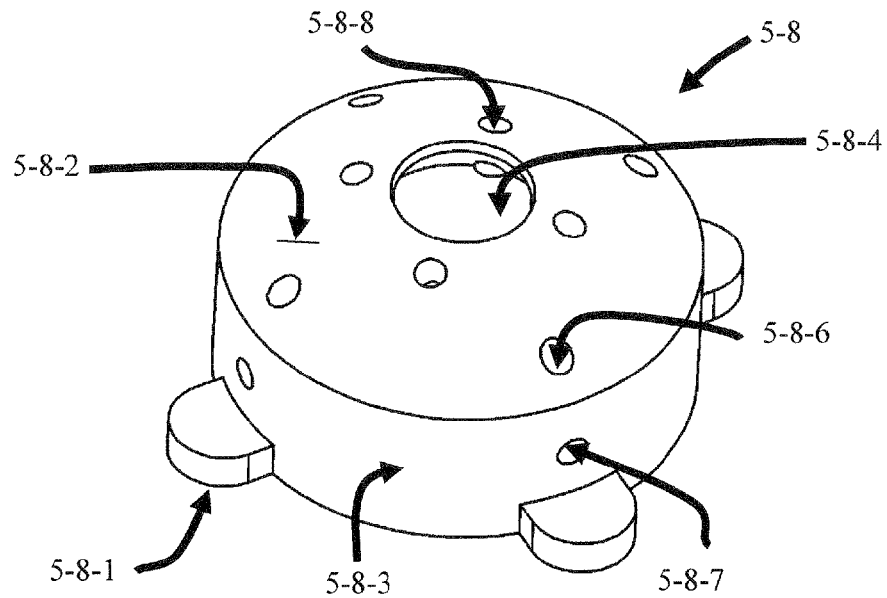

FIG. 38 illustrates a ball-cylinder 5-8 with a particular embodiment of hydraulic portals 5-8-6, 5-8-7, and 5-8-8 that allow fluids and gases to flow into and out of the inner chamber of the cylinder.

Figure 39:
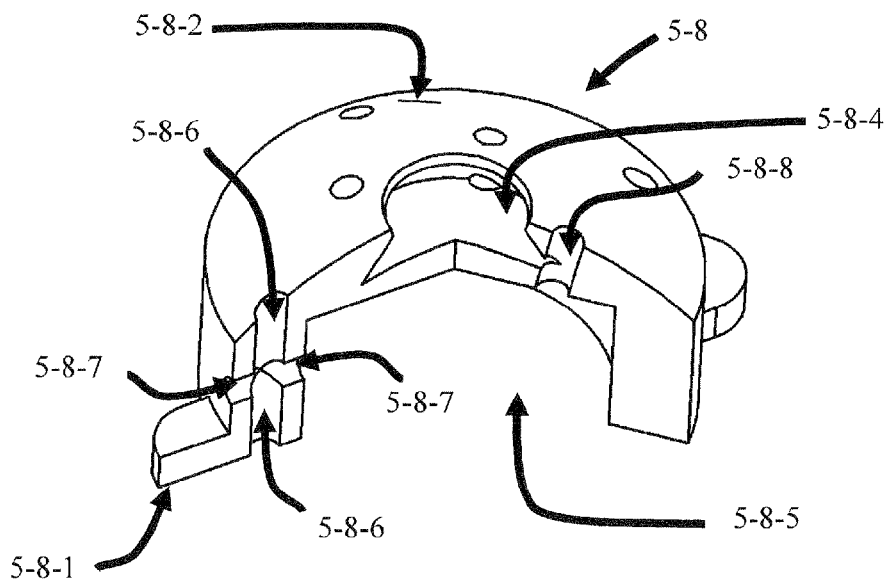

FIG. 39 depicts a cutaway view illustrating an example embodiment of fluid/gas portal conduits. The arrangement of portals and hydraulic conduit paths shown here indicate only a particular embodiment and can be applied to all the ball-cylinders covered by the claims. One skilled in the art, based on the instruction here, should be able to devise any number of schemes and variations of portals and conduit paths and is considered within the scope of the claims.

DETAILED DISCLOSURE

The subject invention in general describes embodiments of a device capable of providing motion with up to six independent degrees-of-freedom. Embodiments of the device can further simultaneously provide reaction to compressive, tension and torsion loads. More specifically, the subject invention pertains to embodiments of a device capable of approximating the potential motion between two vertebrae in a patient's spine.

The following description will disclose embodiments of the subject invention that can be useful in the medical fields encompassing spinal surgery and, in particular, to devices and methods for correcting, replacing, or approximating movement between two vertebrae within a spine, i.e., a Functional Spinal Unit (FSU). More specifically, the embodiments disclosed herein can be useful for the treatment and/or removal of spinal disk herniation. However, a person with skill in the art will be able to recognize numerous other uses that would be applicable to the devices and methods of the subject invention. While the subject application describes, and many of the terms herein relate to, a use for installation within a spine, particularly for the treatment of spinal disc herniation, other uses and modifications therefor that will be apparent to a person with skill in the art and having benefit of the subject disclosure are contemplated to be within the scope of the present invention.

In the description that follows, a number of terms are used in relation to the spine, spinal surgery, and medical devices related thereto. In order to provide a clear and consistent understanding of the specification and claims, including the scope to be given such terms, the following definitions are provided:

The term "Functional Spinal Unit" or "FSU", as used herein, refers to a physiological unit of a spine that includes two adjacent vertebrae, an intervertebral disc and all naturally occurring adjoining ligaments between the vertebrae. An FSU typically does not include connecting tissues, such as muscles, vascular tissue, such as veins or arteries, or nerve tissue.

The term "corresponding elements" of the subject invention will refer to variations in the design of an element wherein the variations have the same or similar function and possess many of same features.

The term "patient" as used herein, describes an animal, including mammals, to which the systems and methods of the present invention are applied. Mammalian species that can benefit from the disclosed systems and methods include, but are not limited to, apes, chimpanzees, orangutans, humans, monkeys; domesticated animals (e.g., pets) such as dogs, cats, guinea pigs, hamsters; veterinary uses for large animals such as cattle, horses, goats, sheep; and any wild animal for veterinary or tracking purposes.

Also, as used herein, and unless otherwise specifically stated, the terms "operable communication" and "operably connected" mean that the particular elements are connected in such a way that they cooperate to achieve their intended function or functions.

As used in the subject application, "kinematic chain", "kinematic linkage", and "kinematic connection" refer to mechanical linkages which inseparably, operably, and serially connect component elements of the subject invention to achieve the motion requirements described herein. It is known to those with skill in the art that a serial 'mechanical linkage' is a series of joints connected with physical links to form a closed and/or open chain. Thus, as will be described herein, the components of the device of the subject invention are inseparably linked, such that the components can move relative to each other, but no joint in the sequence can become separated during the motion. That is, when assembled and installed in an FSU, the surface pair joints formed by the components of the device of the subject invention remain interconnected or physically, but operably, connected at all times to each other during the relative motion of the vertebrae. The resultant kinematic chain links the superior plate to the inferior plate through a series of joints. From superior to inferior plates for a particular embodiment, these are: a planar pair joint, a ball-and-socket spherical pair joint, and a prismatic pair joint. These joint surface pairs can be lower order, that is surfaces, or higher order with ball bearings, roller bearings, sliding bearings and so forth. When the superior and inferior vertebral plates of the invention are fixedly attached to superior and inferior vertebra of an FSU, respectively, the kinematic chain is unbroken from the superior to inferior vertebra for all nominal workspace motions naturally permitted by the disc the subject invention replaces.

The present invention is more particularly described in the following embodiments and examples that are intended to be illustrative only since numerous modifications and variations therein will be apparent to those skilled in the art. As used in the specification and in the claims, the singular for "a," "an" and "the" include plural referents unless the context clearly dictates otherwise.

Finally, reference is made throughout the application to the "cranial end" and "caudal end." As used herein, the cranial end 100 is that end that would typically be nearest to the head of a patient. Conversely, the caudal end 200 of the device is that end that would typically be nearest the tail end of a patient (nearest the foot end in a human patient).

The various embodiments disclosed herein can allow up to six independent degrees-of-freedom throughout the Functional Spinal Unit (FSU) workspace and simultaneously can allow reaction to compressive, tension and torsion loads. The embodiments of the invention pertaining to approximating the potential motion between two vertebrae in an animal spine can maintain the integrity of the variable intervertebral spacing required during motion. For example, under compression, the intervertebral gap can narrow some and under tension it can widen some. During normal motion of the affected FSU, the invention retains an unbroken, fully connected at all times, mechanical linkage between the superior and inferior vertebra. Specifically, each surface in a kinematic pair is chained or linked to the other without interfering with nominal joint motion of that pair. This feature can promote joint stability and assist in preventing the common problem of spondylolisthesis of the FSU during workspace motion. When appropriately scaled, the invention is capable of tracking FSU workspace movements, within prescribed joint limits, for up to three independent translational and three independent rotational motions of the superior vertebra with respect to the inferior vertebra of the FSU. In a patient, the invention can serve, through appropriate mechanical programming of joint stops and scaling, as a disc prosthesis for an FSU at any point along the spine. For example, in a human patient, the embodiments of the device, with appropriate joint stops and scaling can be utilized as a disc prosthesis from the cervical to the lumbar regions.

Particular embodiments of the invention have a general curvate, rectangular, square, cylindrical, or ovoid shape of appropriate height and circumference for the functional spinal unit (FSU) into which the invention is placed after removal of all or part of the natural disc. While these various geometries affect the shape of the superior and inferior plates, the internal joint mechanism can remain essentially the same, as the two examples of external geometries instructed here so illustrate. The FSU angular and translational displacement along the various degrees of freedom, as instructed in the following description and examples, typically relate to cervical spine applications of the invention in a human patient. However, it should be understood that the invention is not restricted to the cervical spine and can be scaled for larger FSUs, for example, L4-L5 in the lumbar region.

The superior and inferior plates (also referred to hereinafter as the superior and inferior vertebral plates) (refer to FIG. 3 and FIG. 25) of the embodiments of the subject invention, illustrated in FIG. 1 and FIG. 23, possess a rounded-corners square and a cylindrical, geometry, respectively. The interior mechanisms of the invention can be, but are not required to be, protected by a tough, multi-layered, fiber reinforced flexible boot 12-1 in FIG. 2 (12-2 in FIG. 24), which can be tightly clamped to the superior vertebral plate 9-1 (9-2) and inferior vertebral plate 1-1 (1-2) by clamping elements 13-1 (13-2). The boot can have multiple functions: provide restoring torques and tension forces to oppose those generated by the muscles and internal spring elements of the device; seal out fluids; seal in fluids; protect the mechanism from bio-fouling; and shock absorption. Other methods and devices can also be used for attaching the boot to the vertebral plates, such as, by way of non-limiting example, grommets and rivets, multiple screw on boot edge clamps, or combinations thereof in possible conjunction with the previously described clamping elements.

FIG. 23 (and FIG. 25) illustrates an embodiment of the invention wherein the boot is not required and has been removed. However, if desired, the boot can be utilized with these embodiments. The operation of certain embodiments of the invention can be visualized with the aid of FIG. 4, FIG. 5 and FIG. 6. These figures present a cutaway view of some of the invention elements in neutral, full flexion, and full extension, respectively. The elements shown in cutaway, in these figures, are the superior and inferior vertebral plates 9-1 and 1-1, the socket 8-1, the ball-cylinder 5-1, the ball-cylinder retainer 6-1 and the spring element 3-1. The uncut elements shown are the segmented-wall inferior and superior mandrels 2-1 and 4-1 and the spherical slider element 7-1.

In FIG. 26 a partial quadrant cutaway of a cylindrical embodiment of the invention illustrates specific characteristics of the internal mechanism of the invention realized in a cylindrical embodiment. In this embodiment, the mobile spherical slider 7-2 is identical to 7-1, a segmented-wall, superior mandrel 4-2 is also identical to 4-1, and an inferior segmented-wall mandrel 2-2 is identical to 2-1. These are shown uncut for clarity. The socket 8-2 is also identical to 8-1, in this embodiment. The elements 8-2, 7-2, 4-2, 3-2, and 2-2 of the cylindrical model, therefore, can also be identical to the corresponding elements in the rounded-corners square model of FIG. 4. The variation, beyond the external shape, between corresponding elements (9-1, 9-2), (6-1, 6-2), (5-1, 5-2), and (1-1, 1-2) usually reflects the choice of external geometry. However, ball-cylinders 5-1 and 5-2 only differ in the size and number of the tabs 5-1-1 and 5-2-1, and were chosen differently for illustrative purposes herein. By using the same tab structure ball-cylinder 5-1 can be made identical to 5-2 without changing the function of the rounded-corners square embodiment. The two ball-cylinders can be made identical, for example, by replacing all their existing tabs with four small tabs 5-2-1. With this change in tabs, the internal cavities 1-1-2 and 1-1-3 of 1-1 and cavities 1-2-2 and 1-2-3 of 1-2 can be made identical, too. These changes make the internal cavities of the inferior vertebral plates 1-1 and 1-2 identical. In such cases, only their external geometry of their respective inferior vertebral plates differs.

The planar joint motion capabilities of the two embodiments differ slightly. Planar surface 9-1-1 can have a rounded-corners square boundary and planar surface 9-2-2, a circular boundary. The boundaries of openings 9-1-3-2 and 9-2-3-2 of socket-retainer bearings 9-1-3 and 9-2-3, of a specific embodiment, can have the same contours as the corresponding boundaries of the planar surfaces to maximize socket mobility, but they can also be curvate, elliptic, polygonal, or, in general, any planar curve shape. The contours of openings 9-1-3-2 and 9-2-3-2 have a significant effect on the possible motions of the socket within the planes of 9-1-1 or 9-2-2 and, thus, can operate as a sophisticated planar joint stop when interacting with the curvate bearing raceway cavity 8-1-3. By way of example, a socket bearing raceway cavity and socket-retainer bearing opening, both with elliptic contours possessing a major-axis-distance to minor-axis-distance ratio equal 2:1, will restrict maximum axial rotations of the superior vertebral plate 9-1 with respect to the socket 8-1 to be less than ±45 degrees, when the socket is dead center of the superior vertebral plate. The permissible axial rotation angle decreases significantly as the socket moves off dead center.

If the boundary of opening 9-1-3-2, when projected onto the plane 9-1-1, is simply an offset of the boundary of the planar surface 9-1-1, then the socket can move between approximately ±1 mm to approximately ±2 mm simultaneously in x and y directions from an origin of a Cartesian coordinate frame located at the centroid of the rounded-corners square.

If the boundary of opening 9-2-3-2, when projected onto the plane 9-2-2, is simply an offset of the boundary of the planar surface 9-2-2, that is a circle, then the socket can move between approximately ±1 mm to approximately ±2 mm radially in any direction as defined by a polar coordinate frame located at the center of the circle. Thus, a cervical embodiment that is a 12 mm×12 mm×8.5 mm rounded-corners square design can allow greater displacement for its planar pair than a cervical embodiment that is 12 mm diameter by 8.5 mm high right-circular cylindrical design can allow for its planar pair, all other dimensions, such as wall thicknesses, cavity sizes, etc., being held equal.

Variations in the curvate perimeter contours of the socket-retainer bearing to accommodate different planar motions and joint stops in the planar kinematic pair joint formed between 9-1 (9-2) and 8-1 (8-2) are considered to be within the scope of this invention. Two non-limiting examples have been instructed herein, socket-retainer bearing 9-1-3 with rounded-corners square contour and socket-retainer bearing 9-2-3 with a circular boundary. All such socket-retainer bearing outer contours will conform to interface with the superior vertebral plate along its cavity wall contours and is fixedly attached, say, press fit or welded into place.

The boundary contours of the plane of the superior vertebral plate, of a socket-retainer bearing opening fixed into that plate, and a concave raceway cavity of the socket dictate the permissible motion capabilities of the planar joint. Choices of contours provide a way of changing the range of motion of the planar joint between the superior vertebral plate and the socket in an infinite variety of ways.

As another example, one can make the lateral width of a socket-retainer bearing opening 9-1-3-2 equal to the inner diameter of the circular bearing raceway cavity 8-1-3 of the socket. This choice of width can engage the lateral sides of the socket-retainer bearing into constant sliding contact with the socket bearing raceway end cavity along a curve, permitting only anterior-posterior linear displacements of the socket. For this configuration, the socket can still spin about its central axis with respect to the superior-vertebral plate. If desired, this particular rotation freedom can be eliminated entirely by making the socket rectangular and its raceway cavity linear and not circular or curvate one. Thus, one can easily convert a planar joint into a one-dimensional prismatic joint that only allows the socket to slide between the anterior and posterior elements of the superior vertebral plate without spinning. The resulting five degrees of freedom embodiment reduces lateral motion. The need for such an embodiment might arise for clinical reasons. Such variations are contemplated to be within the scope of this invention.

The ensuing discussion will focus on the rounded-corners square model with occasional mention of the cylindrical model. It should be understood that the instruction herein can apply to other embodiments, such as, for example, the cylindrical embodiment mentioned herein, with obvious variations in joint range parameters and external geometric shapes being the principal differences, which would be apparent to a person skilled in the art. For any embodiment of the subject invention, the net motion from any initial pose to any terminus pose generated by spinal musculature acting upon the involved FSU can be described by a single rotation about an axis passing through the ball center of curvature and a prescribed translation of the superior vertebral plate with respect to the inferior vertebral plate realized by the planar pair and the ball-cylinder prismatic pair action. To insure that any possible terminus pose generated by an FSU can also be generated by the subject invention, three independent rotational and three independent translational degrees of freedom are sufficient, and that is what the subject invention provides.

In the embodiments described herein, elements that rotate with respect to the inferior vertebral plate are spherical sliders, the socket and the superior vertebral plate. The ball-cylinder, the superior and inferior mandrels, and the ball-cylinder retainer do not rotate with respect to the inferior vertebral plate. The spring and/or cushion elements within the ball-cylinder cavity can possibly rotate internally about the mandrels, but this motion, in general, has no effect on the relative motion between the superior and inferior vertebral plate and can usually be ignored with regard to such motion.

FIG. 4, FIG. 5 and FIG. 6 represent a plane cut of the subject invention in three poses, namely, "neutral", "flexion", and "extension". Nominally, an FSU will move from neutral to poses somewhere between flexion and extension in the sagittal plane, which is the plane of the page in the diagram. Nominal translations and rotations of a cervical FSU in other planes that include the central axis can be less "extreme" than those motions in a sagittal plane that includes the central axis. Central axis symmetry of a cylindrical embodiment permits the same motion capabilities for any plane passing though the central axis, and, in that sense, can passively exceed some motion flexibility requirements in most of those planes, particularly the frontal plane in which lateral rotations take place. By including appropriately designed rotational and translational joint stops, some of these motions can be reduced, if there is a need to do so.

While the rounded-corners square model does not have complete axial symmetry, as in the cylindrical case, its motion capability can be made identical to the cylindrical case by installing a socket-retainer bearing with a circular boundary for its opening.

The previous observations can help to visualize the complete motion generality of the subject invention for either of the two principle embodiments instructed here in detail. Since a natural FSU cannot normally flex as much in the lateral plane as in the sagittal plane, appropriate modifications to spherical slider and planar pair joint control can realize a workspace more closely tuned to that of an actual FSU, if required. In other words, the subject invention can be mechanically programmed to realize workspaces dictated by natural or clinical requirements, or not, as the situation dictates.

In one embodiment, a mobile spherical slider consists of a caudal 200 and cranial 100 end with a connecting stem. The caudal and cranial ends can be wider in extent than the stem and the lateral surface contours of each of the three regions can be curvate. In one embodiment, the inferior surface of the caudal end is concave spherical and the superior surface of the cranial end, convex spherical. The stem can be a graded curvate connection between the two ends, connecting at the edges of the caudal and cranial lateral surfaces, as in FIG. 16A and FIG. 16B and FIG. 17A and FIG. 17B, or, a graded curvate connection between the two ends, but indented from the edges of the lateral surfaces at both ends, as shown, for example, in FIG. 19A and FIG. 19B. In the latter case, an undersurface (refer to 7-4-6) can be created on the cranial end. In a further embodiment, a portion of the undersurface can be concave spherical and rotateably slides against a convex spherical surface in a socket cavity. In a still further embodiment, such a stem construction produces an oversurface (refer to 7-4-7) on the caudal end. With this embodiment, a portion of the oversurface can be convex spherical and rotateably slides against a concave spherical surface in a ball cavity.

In one embodiment, the caudal 200 and cranial 100 ends of a mobile spherical slider fit into accommodating, oversized cavities within each surface of a spherical pair. In a further embodiment, the cavity openings are smaller than the cavity chambers and can be too small to allow withdrawal of the spherical slider from either cavity. All horizontally oriented spherical surfaces of a mobile spherical slider can have the same center of curvature as the spherical pair in order to facilitate sliding and rotating on those surfaces about that center of curvature. With these embodiments, a convex spherical slider is essentially the upper half of a mobile spherical slider and a concave spherical slider is essentially the lower half of a mobile spherical slider.

In a further embodiment, the socket cavity and the ball-cylinder cavity openings are formed with edge surfaces, i.e., the cranial edge surface 8-1-7 and the caudal edge surface 5-1-7, respectively, against which a lateral curvate surface of the spherical slider can operably interact. In one embodiment, the edge surface interacts with a stem lateral surface of the spherical slider. In a further embodiment, the edges surfaces of the cavities can be formed into a variety of shapes or configurations that are compatible with the shape of a stem lateral surface, such as, for example 7-1-3, 7-3-3, or 7-4-3. With this embodiment, as the cranial and caudal ends of the spherical slider move within the respective cavities, the stem lateral surface can slide against or otherwise contact these compatible edge surfaces.

FIGS. 19A and 19B illustrate an alternative embodiment of a spherical slider. In this embodiment, the cranial edge surface 8-1-7 (FIGS. 12, 20, and 28) and the caudal edge surface 5-1-7 (FIGS. 10, 20 and 18) form concave surfaces that are compatible with a stem lateral surface that is convex or partially hemispherical. As discussed above, the increased contact between the stem lateral surface and the edge surfaces reduces prismatic motion of the spherical slider between the two cavities. Further, the socket and the ball-cylinder are kept in operable contact.

A spherical slider, mobile or anchored, can 1) keep the centers of curvature of a concave and a convex spherical surfaces of a spherical pair in proximity, even under the presence of outward radial forces, and even when the spherical surfaces of the joint are less than a hemisphere, 2) limit the rotation angles of the joint about one, two, or three independent axes, depending upon the detailed geometry of, and number of, spherical sliders and cavities in a spherical pair, and 3) rotate with the concave and convex surfaces as part of a multi-spherical joint, where all spherical surfaces participating in the joint motion possess the same center of curvature, but can have different radii of curvature. A mobile spherical slider 7-1 (7-2, 7-3, 7-4, 7-7) can be manufactured as a single entity in a particular embodiment and comprises a caudal end lateral surface 7-1-4 (7-2-4, 7-3-4, 7-4-4, 7-7-4), a stem lateral surface 7-1-3 (7-2-3, 7-3-3, 7-4-3, 7-7-3), and a cranial end 100 lateral surface 7-1-2 (7-2-2, 7-3-2, 7-4-2, 7-7-2). The caudal end 200 can have a concave spherical sliding surface 7-1-5 (7-2-5, 7-3-5, 7-4-5, 7-7-5) and the cranial end can have a convex spherical sliding surface 7-1-1 (7-2-1, 7-3-1, 7-4-1, 7-7-1). These spherical surfaces can further slide and/or rotate on spherical sliding surfaces of the same curvature in the socket and ball cavities. For example, the caudal sliding surface 8-1-9 in the socket 8-1 can have a radius and center of curvature compatible with the spherical sliding surface of a spherical slider. In a further embodiment, mobile spherical slider 7-4 has two additional spherical surfaces upon which to slide and rotate: concave 7-4-6 and convex 7-4-7. Spherical surfaces of cavities 5-4-4 and 8-4-4 that pair with spherical slider spherical surfaces, can be large enough to allow the spherical slider to rotationally slide about in the cavity without interference. All the spherical surfaces of a mobile spherical slider can have the same center of curvature as the socket and the ball spherical pair. Where there is no confusion, the cranial, caudal and stem of slider will also be referenced by their lateral surface numbers.

The boundaries for the spherical surfaces in example embodiments 7-1, 7-2 and 7-4 are circles, in embodiment 7-3, curvate elliptic-like, in 7-7, curvate rectangular-like. Cranial and caudal end boundary shapes and their respective cavity shapes can have substantial affect on how spherical sliders set angular limits and control rotational motion of a spherical pair. In joint rotation control, even stem lateral surface curvature can be used to establish joint angle limits, independently of the other methods. In general, caudal and cranial spherical surfaces of the spherical slider can posses any plane curved shape including, but not limited to elliptical, circular, squared, rectangular, triangular, or any other polygonal shape. It should be clear to one skilled in the art, based on the extensive instruction herein, how to change these boundaries to generate desired rotational control of a spherical pair and/or maintain operational integrity of such pairs.

A mobile spherical slider cranial and caudal ends can be wider than the widest openings 8-1-8 of socket cavity 8-1-4 (8-2-4, 8-3-4, 8-4-4, 8-7-4) and 5-1-4 (5-2-4, 5-3-4, 5-4-4, 5-7-4), respectively. Therefore, under nominal operation, this embodiment of a mobile spherical slider allows rotations of a spherical pair about the pair's putative center of curvature and severely restricts, and, in some cases, effectively prevents any other type of motion for the spherical pair. Some spherical sliders can allow small displacements between the centers of curvature of the two surfaces in a spherical pair, but the primary motion is rotational. The allowed radial separation between the centers of curvature of a ball-and-socket spherical pair afforded by a spherical slider depends upon the detailed geometry of the spherical slider and can be, in a particular cervical embodiment, approximately 1 millimeter or less for 7-1, 7-2, 7-3, 7-5, 7-6 and 7-7 and approximately zero for 7-4.

In general, a spherical slider, mobile or anchored as the case may be, prevents, for x=1, 2, 3, 4, 5, 6, separation of the centers of curvature of spherical pair (8-x-2, 5-x-2) by any significant distance during ball-and-socket rotations.

Spherical sliders 7-1, 7-2, 7-4, 7-5, and 7-6 with circular boundaries typically do not constrain rotations of a socket about the sliders' central axes when the socket cavity spherical surface boundary is also circular. However, they can constrain rotations about any axis comprising a linear combination of the sagittal and lateral axes Spherical slider 7-3, with non-planar, elliptic-like, curvate, spherical surface boundaries, can serve as a rotational joint stop for any axis of rotation through the common center of curvature, including the central axis of the slider. In a particular embodiment, spherical slider cranial and caudal elements of 7-4 could be modified to be elliptic in nature and achieve the same rotational control, but with much tighter radial constraint of the common center of curvature.

The complete six-degree-of-freedom flexibility of motion which can be realizable by the embodiments of the subject invention, namely, three independent rotation motions and three orthogonal translation motions, can be restricted, independently, by appropriate sizing of the socket-retainer bearing 9-1-3 (9-2-3) to limit planar joint motion; by insertion of appropriately dimensioned cushion and prismatic joint stop elements within cavities of 1-1 (1-2) to limit axial prismatic motion; and by insertion of appropriate spherical sliders within a conforming ball-and-socket spherical pair. By way of a non-limiting example, configuration 5-3, 7-3, and 8-3 (FIG. 18) allows rotations about three independent axes, but limits the range of those rotations. Alternatively, configuration 5-7, 7-7, and 8-7 (FIG. 22) only permits sagittal axis rotations, constraining all others to zero.

In one embodiment, convex spherical slider and ball-and-socket joint connector 7-5 (FIG. 33) does not rotate with the socket, but rather is fixedly attached, manufactured as part of, or is otherwise contiguous with the ball. In a further embodiment, concave spherical sliders and ball-and-socket joint connector 7-6 (FIG. 34) are fixedly attached to, manufactured as part of, or are otherwise contiguous with a socket and rotates with it. An embodiment having two concave spherical sliders 7-6 is shown in FIG. 34 and FIG. 35. An embodiment of a ball-cylinder 5-6 that can accommodate two such rotational joint stop is shown in FIG. 36.

When an embodiment of the subject invention is installed in an FSU, FIG. 4, FIG. 5 and FIG. 6, indicate the configuration of the device as it would appear at neutral, extreme flexion, and extreme extension, respectively. During flexion, with the embodiment shown in FIGS. 4, 5, and 6, the superior vertebral plate 9-1 translates anteriorly across the two-degree-of-freedom plane-bearing surfaces 8-1-1 (FIG. 12) and 9-1-1 (FIG. 13), rotates anteriorly about a sagittal axis (perpendicular to the plane of the cut in the figures) passing through the center of curvature of the ball-and-socket spherical pair (8-1-2, 5-1-2) and compresses caudally the prismatic pair established by ball-cylinder 5-1 and inferior vertebral plate 1-1. During extension, with this embodiment, the superior vertebral plate 9-1 translates posteriorly across the two-degree-of-freedom plane-bearing surfaces 8-1-1 (FIG. 12) and 9-1-1 (FIG. 13), rotates posteriorly about a sagittal axis passing through the center of curvature of the ball-and-socket spherical pair (8-1-2, 5-1-2) and extends cranially the prismatic pair established by ball-cylinder 5-1 and inferior vertebral plate 1-1. For more complex motions that involve lateral translations and rotations, the full capabilities of the planar, spherical and prismatic pairs can be engaged.

In a preferred embodiment, for all FSU workspace motions, however, the elements of the subject invention remain connected from the superior vertebral plate 9-1 (9-2) to the inferior vertebral plate 1-1 (1-2) through a kinematic chain, as described in the following embodiments. During planar motion of the superior vertebral plate 9-1 (9-2) with respect to socket 8-1 (8-2), rounded-corners square socket-retainer bearing 9-1-3 (9-2-3) can engage circular bearing raceway cavity 8-1-3 (8-2-3) and keeps 9-1 (9-2) from mechanically separating from 8-1 (8-2), as the opening created by the curvate perimeter of 9-1-3-2 (9-2-3-2) is too small at all points on the perimeter for the upper raceway lip 8-1-5 (8-2-5) of socket 8-1 (8-2) to be withdrawn from the superior vertebral plate 9-1 (9-2) with any clearance, establishing kinematic connection during motion of the superior vertebral plate and the socket.

Axial rotation of 9-1 (9-2) can be constrained by the boot, but not by the kinematic chain of this particular embodiment of the subject invention. Lateral and sagittal rotations of 9-1 (9-2), however, can mechanically couple with socket 8-1 (8-2) forcing the socket to rotate about those axes by means of a ball-and-socket joint realized by spherical pair 8-1-2 (8-2-2), a concave spherical surface, and ball convex surface 5-1-2 (5-2-2).

Spherical slider 7-1 (7-2) can also keep the socket and ball-cylinder spherical surfaces 8-1-2 (8-2-2) and 5-1-2 (5-2-2) from separating radially outward to any significant distance, typically less than approximately one millimeter, and simultaneously can limit the angular motion of the spherical pair. In a particular embodiment, while the two spherical surfaces under certain conditions might separate a small amount, they cannot totally separate from one another under nominal force conditions, since the openings of cavities 8-1-4 (8-2-4) and 5-1-4 (5-2-4) are too small, by design, for the ends of 7-1 (7-2) to clear and pass through. This establishes the linkage between 5-1 (5-2) and 8-1 (8-2), and the latter has been shown to remain connected to 9-1 (9-2) during motion.

During flexion, compression forces and the spherical slider help keep the spherical surfaces 5-1-2 (5-2-2) and 8-1-2 (8-2-2) of the spherical pair in contact while those same forces and the socket-retainer bearing keep the planar surfaces 8-1-1 (8-2-1) and 9-1-1 (9-2-1) in contact. During extension, boot tension can help keep those same surfaces in contact as well as the socket-retainer bearing and spherical slider.

In a further embodiment, ball-cylinder 5-1 (5-2) can slide up and down its central axis, but is constrained at one end by the inferior vertebral plate 1-1 (1-2) and, at the other, by the ball-cylinder retainer 6-1 (6-2). Nominally, with this embodiment, the ball-cylinder compresses spring and/or cushion elements 3-1 during flexion and permits the spring and/or cushion elements to expand during extension. Retainer 6-1 (6-2) can also block further extension of 5-1 (5-2) when tab elements 5-1-1 (5-2-1), fixedly attached to the cylinder walls of 5-1 (5-2), engage the undersurface of 6-1 (6-2). In a still further embodiment, element 1-1 (1-2) blocks the tabs and cylinder wall from further motion during a compression stroke. The range of the ball-cylinder stroke, therefore, can be dictated by the height above the upper surface of tab elements 5-1-1 (5-2-1) to ball-cylinder retainer 6-1 (6-2) undersurface, when the hall-cylinder 5-1 (5-2) rests on the bottom of the cavities 1-1-2 (1-2-2) and 1-1-3 (1-2-3). Varying the tab height can modify the stroke length. In one embodiment, spring and/or cushion elements are inserted into cavities 1-1-2 (1-2-2) and 1-1-3 (1-2-3) on the top surfaces of tabs 5-1-1 (5-2-1), which therefore, will shorten the ball-cylinder stroke and provide more resistance to extension and compression. In an alternative embodiment, cushion elements can also be placed under the tabs 5-1-1 (5-2-1) and the cylinder wall 5-1-3 (5-2-3) to reduce the stroke length and add further shock absorbing characteristics. In further alternative embodiments, both could be utilized, or the tabs 5-1-1 (5-2-1) can be cushion elements themselves to simultaneously accommodate both compression and extension shocks to the FSU. During nominal FSU six-degree-of-freedom motion, therefore, a kinematic chain of joint linkages extends from the superior vertebral plate 9-1 (9-2) to the inferior vertebral plate 1-1 (1-2), and, hence, between the vertebra of an FSU to which these plates are fixedly attached.

The previous discussion on kinematic connectivity during nominal motion of the device revolved around the embodiments depicted in FIG. 7 and FIG. 27, but applies equally as well to those embodiments wherein the socket, spherical sliders, and ball-cylinders depicted in FIG. 18, FIG. 20, FIG. 22, FIG. 33, and FIG. 34 are substituted for the corresponding elements 8-1, 7-1 and 5-1. Modifications to the ball-cylinder tabs in these figures, to accommodate the cylindrical model inferior vertebral plate configuration, makes this assertion valid for cylindrical embodiments, as well as when such modifications are substituted therein.

When spinal tendons and muscles act on installed embodiments of the subject invention to generate extension motion of an FSU, then, a rounded-corners square embodiment, as shown, for example, in FIG. 6 undergoes the maximum extension configuration. A figure for embodiments of the cylindrical version has a similar appearance, so both can be discussed together. In extension, the superior vertebral plate 9-1 (9-2) can rotate about the ball center and can translate posteriorly in the plane 9-1-1 (9-2-2). The socket can also rotate on the spherical slider 7-1 (7-2) the maximum extent allowed by the socket cavity 8-1-4 (8-2-4) and then forces 7-1 (7-2) to slide on the spherical surface on the floor of cavity 5-1-4 (5-2-4) for the remaining angular rotation. This is typically approximately twice the amount possible with an equally dimensioned anchored spherical slider occupying the same cavity. Thus, for this embodiment, the maximum angular rotation possible for extension equals the maximum angular rotation for flexion and both compute as the difference in angular dimension of the cavity spherical surface and its conforming mobile spherical slider's spherical surface.

Thus, generalizing from sagittal plane motion to all planes passing through the central axis of the FSU as defining "neutral", "flexion", "extension" configurations in those planes, we can establish, in all cases, a kinematic connectedness regardless of the nominal relative motion between the vertebrae of an FSU for which the invention workspace matches that of the FSU. In some clinical cases, full symmetric motion capabilities of the invention may not be desired. In such situations, one can change geometric parameters and joint stop scaling for the various joint elements employed by the various embodiments of the invention, in particular, for the planar, spherical, and axial slider joints, to achieve those ends. With appropriate changes, therefore, the invention can be mechanically programmed to meet specific FSU workspace motion and workspace requirements.

An exploded, three-dimensional view of a rounded-corners square embodiment of the invention, as shown, for example, in FIG. 7, illustrates all the elements uncut. The inferior segmented-wall mandrel 2-1 can be fixedly attached by, for example, being welded or press fit, into cavity 1-4 of the inferior vertebral plate 1-1 or, at manufacture, integrated as part of 1-1, or is otherwise contiguous with the inferior vertebral plate. Similarly, the superior segmented-wall mandrel 4-1 can be fixedly attached to the ceiling of cavity 5-1-5 in the ball-cylinder 5-1, integrated as part of 5-1 in manufacture, or otherwise be made contiguous with 5-1, within cavity 5-1-5. In a further embodiment, the wall-segments of the inferior and superior mandrels 2-1 and 4-1 interlace or interact so that as the ball-cylinder 5-1 translates up and down in cavities 1-1-2, 1-1-3 of the inferior vertebral plate, the two mandrel elements always mesh to some extent and the wall-segments slide or move past one another. This can be seen in FIG. 4, FIG. 5 and FIG. 6. For any ball-cylinder stroke position, there can exist a central mandrel mechanical support and centering of spring and/or cushion elements for the entire length of the cavity 5-1-5. At full closure (FIG. 5), the superior mandrel is able to fully mesh (maximum overlap) with the inferior mandrel 2-1 and seats into cavity space within 1-1-4 not occupied by the wall segments 2-1. At full extension, the inferior and superior mandrels wall segments can minimally overlap (FIG. 6). In the neutral and other cylinder heights between the extreme positions, the superior and inferior mandrel side-wall surfaces can partially overlap, as can be seen in FIG. 4 and more clearly in FIG. 11.

In a further embodiment, the spring/cushion element(s) 3-1 slide over the mandrels 2-1 and 4-1 for centering and support. In alternative embodiments of the invention, the mandrel elements can be eliminated altogether, such as, for example, when a cushion element or a spring element may not require mandrel support or when the outer walls of the ball cylinder provide sufficient support. By way of a non-limiting example, the entire cylinder component of the ball-cylinder can be, in a particular embodiment, a machined helical spring manufactured with a ball at one end and tabs at the other. Such a machined helical spring can be fixedly attached to the floor of the inferior vertebral plate and fit into the cavities 1-1-2 and 1-1-3. As the helical spring compresses or extends, it accomplishes both load bearing capacity and prismatic motion along its central axis. Cavity 1-1-4, platform 1-1-7, the inferior mandrel 2-1, and the superior mandrel 4-1 can be eliminated in such a design.

In any embodiment of this invention, the external central cylinder walls and the segmented-wall mandrel cores can, together, firmly hold one or more spring and/or cushion elements in place. A spring element, for example, can consist of a stack of one or more Belleville springs 3-1 in a variety of series/parallel spring configurations that fit within the available cavity space of the central cylinder. The number, arrangement and spring rates of the Belleville springs in the stack can determine the intervertebral spacing when the invention is under load in the spine. The invention can then accommodate a wide variety of patient situations by changing the composition of the spring stack. In this way, the invention can compensate for patient requirements without changing the design and/or structure of the invention elements. In effect, the spring stack composition can realize a wide range of models to accommodate a wide range of applications at minimum cost.

In a particular spring element embodiment, to realize a cervical sized prosthetic device, up to 10 Belleville springs, can fit within the central cylinder. The Belleville springs can consist of stainless steal, titanium, titanium coated stainless steal or other elastic bio-inert materials such as polyeheretherketone, polyurethane or other high molecular density thermoplastics. One can configure combinations of series and parallel stacks with varying spring constants to provide non-linear spring performance. A piecewise linear spring to approximate a non-linear spring can be constructed from a series stack of Belleville springs with increasing spring constants, arranged, for example, in increasing order from top to bottom. As the Belleville springs with smaller spring constants reach maximum deflection they no longer contribute to the spring constant of the stack. The overall spring constant in the stack increases with each additional spring reaching maximum deflection, i.e., the spring stack stiffens more each time an additional individual spring reaches maximum allowed compression. This non-linear compression behavior of the spring element can be embodied in a large variety of ways, depending upon the selection of spring constants for the individual springs.

A person with skill in the art will recognize that an inversion of any Belleville spring, which can occur at the singularity produced when the spring is at 100% compression, can damage the spring and can change, at least minimally, the spring constant of the stack by converting a series configuration, in which the inverted spring is a part, into a parallel configuration. Unless the spring re-inverts, this can have a deleterious effect on the intended operation of the device and should be avoided. Similarly, a parallel configuration of two Belleville springs would convert to a series configuration if one spring inverted. Embodiments of the invention can utilize guard slip rings or lip guards, as instructed by Doty in U.S. Pat. No. 7,927,375, which is included herein by reference, and can, thus, restrict the amount of linear displacement along the axial axis since the springs are prevented from closing down completely. For such Belleville springs, compression saturation occurs before 100% flattening of the spring and the non-linear compression behavior can be realized without threat of flipping the springs.

In a particular embodiment, the total displacement for ten springs in series equals $10 \cdot h_e$ millimeters, where $h_e$, in millimeters, is the effective height of the Belleville spring, i.e., the actual amount the guards will allow each spring to compress. In a specific embodiment, if $h_e$ equals 0.224 mm, the spring stack of 10 springs in series will compress a maximum of 2.24 mm. Therefore, in a further specific embodiment, a Belleville spring of 6 min outside diameter, 3.2 mm inside diameter and height 0.32 mm and guard lips of 0.08 mm will constrain a spring in a serial matched pair to compress no more than 70% of its height. The ring-guarded maximum compression per spring, in this embodiment then, is 0.7 times 0.32 mm or 0.224 mm. At maximum compression the spring height can be approximately 2 mm to approximately 2.25 mm and at maximum extension approximately 3.68 mm to approximately 4 mm. Under normal cranial load, the invention can be made to compress approximately 1 mm, leaving approximately 1 mm travel for absorbing overloads. The central hydraulic cylinder, mandrel, and spring stack can also offer a relatively rigid column between the FSU vertebrae to oppose shear forces on the device and, hence, the FSU.

In another embodiment, cavities 1-1-2, 1-1-3, and 1-1-4 in the inferior vertebral plate 1-1 (FIG. 8) accommodates the wall 5-1-3 of the ball-cylinder 5-1 (FIG. 10), its tabs 5-1-1, here, four in number, and the seating of the superior segmented-wall mandrel 4-1 at the maximum allowed compression of the spring element. In assembly, the insertion of the ball-cylinder 5-1 into the inferior vertebral plate cavity (FIG. 11) can be followed by fixedly attaching the ball-cylinder retainer 6-1 to the top surface of 1-1 (FIG. 9). The tabs 5-1-1 can vary in number, size, shape, and location around the periphery of 5-1-3. The embodiments 5-1 and 5-2 illustrate examples choices in number and size and location. Tab geometry can be spherical or curvate as well as chamfered cylindrical shapes. From these examples, other choices, and their requirements on cavities 1-1-2 and 1-1-3, should be obvious to one skilled in the art. Such variations are contemplated to be within the scope of the subject invention.

In one embodiment, the spherical slider 7-1 (FIGS. 16A and 16B) is not attached to either 8-1 or 5-1 and can independently rotate by sliding on spherical surfaces within cavities 8-1-4 and 5-1-4. Cavity interior surfaces curvatures can match the contact curvature of the cranial 100 and caudal 200 end elements of a spherical slider and the curvature of their openings can match the contact curvature of the stem's lateral surface as the slider encounters the edges of the cavity openings. For example embodiment 7-1 and cavities 5-1-4 and 8-1-4 can have conical lateral surfaces that contact in a line, including the edges of the openings. On the other hand, spherical slider 7-4 and its cavities 8-4-4 and 5-4-4 (FIG. 19A and FIG. 19B and FIG. 20) can have spherical lateral surfaces that contact in circular arcs. Note the stem lateral surface 7-4-3 also contacts the edge openings in circular arcs These and other curvate and/or rectilinear embodiment geometries can be used as illustrated in FIG. 4, FIG. 5, FIG. 6, FIG. 17A and FIG. 17B, FIG. 18, FIG. 19A and FIG. 19B, FIG. 20, FIG. 21A and FIG. 21B, and FIG. 22.

Spherical slider 7-4 in FIG. 19A and FIG. 19B differs from the other slider examples in that there is a surface discontinuity between the caudal and cranial ends and the slider's stem. This structure generates an upper and lower spherical contact surface on the cranial end and the same for the caudal end so that all four surfaces can remain in operational contact with their respective cavity spherical surfaces at all times during slider or spherical pair motion.

Socket 8-1 can rotate on the spherical surface 5-1-2 of ball-cylinder 5-1, about some axis of rotation passing through the center of curvature of the ball's spherical surface, said axis not being aligned with the central axis of the spherical slider 7-1. Said motion can cause cavity wall 8-1-4 to eventually contact the spherical slider on its lateral surfaces 7-1-2 and 7-1-3, which can be conic sections. At that point the spherical slider 7-1 can begin to slideably rotate together with 8-1 as the angle of rotation increases. To smoothly enable this rotational sliding action, convex spherical surface 7-1-1 and concave spherical surface 7-1-5 can be supported by spherical surfaces of opposite curvature in the socket cavity 8-1-4 and the ball cavity 5-1-4, respectively. All the spherical surfaces mentioned in the previous sentence can possess the same center of curvature as the ball-and-socket surfaces 8-1-2 and 5-1-2 and can have circular boundaries. Concomitant joint rotation of the spherical slider and the ball-cylinder continues until edges 7-1-3 and 7-1-4 engages the wall of cavity 5-1-4. At that point, angular rotation of the ball about the given axis stops since 7-1 is at extreme positions in both cavities 8-1-4 and 5-1-4 and cannot rotate further, effectively acting as a spherical joint stop.

For an axis comprised of a linear combination of the sagittal and lateral axes, the number of degrees the ball-and-socket can rotate from the neutral position before being stopped by the spherical slider 7-1 usually equals the sum of the permitted rotation angles of 7-1 within the two cavities 8-1-4 and 5-1-4. For example, cavity openings of a spherical pair whose angular dimension is 10 degrees larger than the angular dimension of its spherical slider midsection can permit a net rotation angle of approximately ±10 degrees about any axis comprised of a linear combination of the sagittal and lateral axes, when the spherical slider 7-1 is centered within both cavities. This constitutes a range of approximately 20 degrees for such axes of rotation.

A spherical slider 7-1 cannot constrain rotations about central axes of surfaces 7-1-1 and 7-1-5 in certain cases. The central axis of surface 7-1-1 and 7-1-5 can be coincident, as shown in FIGS. 16A and 16B, and can pass through the center of curvature. In this embodiment, the socket (ball) can spin about the central axis of spherical surface 7-1-1 (7-1-5) without moving the spherical slider, as long as there is no interference between the cavity lateral surfaces and the slider lateral surface 7-1-2 (7-1-4). As just discussed, unconstrained central axis rotation of the ball is possible, but tab elements 5-1-1 of the ball-cylinder 5-1 prevent the ball from actually rotating about the central axis of spherical surface 7-1-5, independent of the action of the slider. Under this and similar circumstances discussed in the previous paragraph, the spherical slider itself can spin in the cavities 8-1-4 and 5-1-4 and, thus, provides no joint stop function for this specific embodiment. A spinning 7-1 about its central axis can, in this embodiment, have no net affect on the motion between the superior and inferior vertebral plates. As the spherical slider rotates and slides about the conforming spherical surface in cavities 8-1-4 and 5-1-4, the unconstrained axis of rotation can change orientation as it always aligns with the central axis of spherical surface 7-1-1.

In one embodiment, the boundaries of spherical surfaces 7-1-1, 7-1-5, ceiling of 8-1-4, and floor of 5-1-4 can be non-uniform., i.e., other than circular, and produce non-uniform rotation joint-stop limits. This has already been demonstrated above with the non-planar, elliptic-like curvate boundary spherical sliders 7-3 (FIG. 17A and FIG. 17B) and the non-planar, rectangular-like curvate spherical slider 7-7 (FIG. 21A and FIG. 21B).

The previous operational discussion for slider 7-1, socket 8-1, and ball-cylinder 5-1 also applies to slider 7-4 configured with socket 8-4 and ball-cylinder 5-4. The latter configuration can have the additional feature of more effectively keeping coincident the centers of curvature of the socket and the ball.

Under non-uniform boundaries, such as the elliptic-like one, the rotation limits can vary significantly from rotation axis to rotation axis. For elliptic-like boundaries, with major axes in the sagittal plane and minor axes in the lateral plane, angular gaps can be designed to provide approximately ±10 degrees about the sagittal and lateral axes and approximately ±21 degrees about the central axis of the spherical slider. Rotation angles about other axes will vary depending on the equivalent sagittal, lateral, and central axis angles compounded together to produce the net rotation.

Two or more spherical sliders, even of different sizes and shapes, can be implemented on the same ball-and-socket joint. Two sliders can provide joint stops for all three rotation degrees of freedom, even when circular bounded spherical surfaces for the sliders and cavities are used. The socket and the ball element can have two supporting cavities in each of their spherical surfaces to support installation of the two spherical sliders. The center axes of both sliders can intersect at the common center of curvature of all the spherical surfaces involved in the ball-and-socket-spherical-slider joint. In such an embodiment, spin about the axis of one spherical slider can be controlled by the other and vice-versa. Hence, no rotation axis is unconstrained, no matter the configuration of the ball-and-socket and spherical sliders.

Spherical sliders, in general, cannot influence the rotation of the superior vertebral plate 9-1 about the central axis of socket 8-1 in the plane of the planar pair (8-1-1, 9-1-1). As indicated previously, however, special contours for the socket-retainer bearing and the socket hearing raceway cavity can be devised to limit the range of such rotations. For example, if both contours are elliptical with a 2:1 major-axis/minor-axis ratio, the superior vertebral plate can be limited to approximately ±45 degrees rotation about the socket's central axis. The boot, as well as natural spinal column constraints, however, can also help prevent excessive, unconstrained rotations of the superior vertebral plate about the central axis of the planar joint (8-1-1, 9-1-1) and, under certain circumstances, may not even permit the ±45 degrees.

Assembly of the ball-and-socket in the first embodiment can be achieved by any number of devices and methods known to those with skill in the art. One method is to halve the socket 8-1 and ball-cylinder 5-1, insert the spherical slider 7-1 into the one of both the socket and ball-cylinder, and then fixedly attach, such as, for example, by peg and weld techniques. This will place the spherical slider into the cavities 8-1-1 and 5-1-1 and chain the socket and ball-cylinder together without restricting rotations, up to the maximum allowed by the design of the cavities and spherical slider.

Another method of assembly is to make a cut in the ball-and-socket cavity openings the maximum width of the respective spherical surfaces (7-1-1 or 7-1-5) such that the cut descends into their respective cavities (8-1-4, 5-1-4) at an angle that allows sufficient passage of the spherical slider surfaces into the cavities, but not at an angle that can be realized under nominal operation. Cranial loads, a central spring element, and a boot can keep the spherical surfaces of the slider, ball, and the socket in contact throughout FSU workspace motions.

A convex spherical slider 7-5 can fixedly attach, be manufactured as a unit, or be otherwise contiguous with a ball-cylinder 5-5 (FIG. 33); can be configured to kinematically chain the socket to the ball while maintaining up to three degrees of rotational freedom; and can be used as an alternative to the mobile spherical slider technique. With this embodiment, element 7-5, within the socket cavity 8-1-4, fully participates as an integral part of the lower-pair ball-and-socket joint comprised of 8-5=8-1 and 5-5 while maintaining joint connectivity. A combination of convex spherical sliders 7-5 and/or mobile spherical sliders 7-1 can be configured on the ball surface to constrain all three independent angles of rotation of a ball-and-socket joint. Since the narrowest width of the engaging surface 7-5-1 is larger than the greatest width of the orifice of 8-1-4, the two interfere with each other if attempt is made to separate the socket and ball centers of curvature. In a further embodiment, multiple anchored spherical sliders can be utilized. This will be shown specifically in the next paragraph for two concave spherical sliders.

A concave spherical slider is one fixed to a concave spherical surface of a spherical pair joint and, in this embodiment, can be fixedly attached to the socket's concave spherical surface. Multiple concave spherical sliders can be fixed to a socket and can work together to systematically control rotation angles. The two concave spherical sliders 7-6 in FIG. 34 and FIG. 35 fixedly attach to the socket's concave spherical surface 8-6-2 and can engage dual cavities 5-6-4 within the ball-cylinder 5-6 with spherical surface 5-6-2. Since, in this embodiment, the narrowest width of the engaging surfaces 7-6-5 are larger than the greatest width of the orifices of 5-6-4, concave fixed rotational joint stops interfere with the ball orifice edges if attempt is made to separate the socket and ball centers of curvature.

Various alternative embodiments of a spherical slider and spherical slider cavity geometries, and various fixed rotational joint stop geometries, fixed on a socket and/or a ball, as well as other combinations in number and position of sliders and fixed stops, can be determined by one skilled in the art. It is contemplated that such variations are within the scope of the subject invention.

For example, Errico et al. instruct in U.S. Pat. No. 6,989,032 B2 the use of a curvate protrusion on the ball into a socket cavity or a curvate protrusion on the socket into a ball cavity in order to realize a rotational joint stop. In U.S. Pat. No. 7,163,559, he instructs the use of a ball bearing with point contact within a ball cavity to create a rotational joint stop.

Conversely, the fixed-rotational-joint stops and spherical sliders instructed herein do not just limit rotation angles, but can also maintain joint connectedness (a kinematic chain) for a large radius of curvature spherical pair within a small volume, a spherical pair wherein the ball consists of a convex spherical cap that can be less than a hemisphere and the concave spherical surface of the socket, too, can be less than a hemisphere. Connectedness of a ball-and-socket wherein the ball and socket spherical surfaces exceed a hemisphere, or the ball is encapsulated, as in the Errico case, is not an issue. The elements instructed herein can also provide greater surface area between the engaging parts, and engages them smoothly as additional ball-and-socket surface features, thus reducing wear introduced by point contact rotational joint control.

In a further embodiment, a protective boot with clamping elements, for example, 12-1 (12-2) and 13-1 (13-2), can assist in hydraulic and shock absorption properties by offering resistance to fluid expansion within the device as forces telescope the hall-cylinder down into the inferior vertebral plate. Additional cushioning elements within the central hydraulic cylinder can also be used to enhance shock absorption. Hydraulic portals can be embodied as in FIG. 38 and FIG. 39. Hydraulic portals, known in the art and instructed, for example, in Doty (U.S. Pat. Nos. 7,361,192, 7,799,080, and 7,927,375, as well as U.S. Patent application no. US2010/0324688A1 and Published PCT Application No, PCT/US2010/37721), can also be utilized with the embodiments of the invention described herein. FIG. 38 and FIG. 39 illustrate various embodiments of hydraulic portals that can be utilized with a ball cylinder 5-1. For example, one type of hydraulic portal 5-8-8 can extend from surface 5-8-2, partially through cavity 5-1-4, and into ball cylinder cavity 5-8-5. Another type of hydraulic portal 5-8-6 can extend from surface 5-8-2 through the ball cylinder wall 5-1-3. Hydraulic cylinder 5-8-7 can extend perpendicularly through the ball cylinder wall 5-1-3 into the ball cylinder cavity 5-8-5. A ball cylinder can have any one or all of these different types of hydraulic portals. Further, one or more these, or other types of, hydraulic portals can be utilized with any or all of the components of the embodiments of the subject invention.

The inclination of the invention with respect to the body coordinates will usually depend upon the natural inclination of the FSU to the body planes. Specifically, the invention can be inserted into an FSU, with the disc partially or fully removed, such that the superior outside surface of a superior vertebral plate 9-1 (9-2) can be approximately centered on the disc footprint, and flush with, the inferior surface of the superior vertebra of the FSU, and the inferior outside surface of an inferior vertebral plate 1-1 (1-2), can be approximately centered on the disc footprint, and flush with the superior surface of the inferior vertebra of the FSU, such that both outside surfaces are parallel when the FSU is in the neutral position. In the neutral position, a line joining the tip centers of the central guide pins on the superior and inferior vertebral plates, i.e., the invention central axis, should typically parallel a central axis vector of the FSU for maximum workspace utility. The two axes can be coincident or the device axis slightly anterior to the FSU central axis, but on the same sagittal center line, i.e., a line that splits the FSU into two equal lateral halves. Surgically, one drills pilot holes, centered on the disc footprint of the superior and inferior vertebrae inferior and superior surfaces, respectively, in a patient's FSU in line with the central axis of the FSU, for the guide pins 10-1 and fusion spikes 11-1. The guide pins can be longer than the cancellous bone fusion spikes 11-1 and can be inserted into the pilot holes a millimeter or more before the penetrating fusion spikes engage the cancellous bone. This method can stabilize the invention in the proper position and orientation within the patient's FSU as the vertebra press onto the fusion spikes. Proper placement of the invention between the vertebrae of an FSU can maximize the effective work space of the installed prosthesis. With the superior and vertebral plates mounted as instructed, the invention will accommodate to the FSU workspace motion requirements and settle into a nominal working configuration compatible with the FSU workspace.

While only one guide pin is shown in the figures, there can be more than one on each of the inferior and superior vertebral plates 1-1 and 9-1. For example, there can be a center guide pin and a second guide pin elsewhere on the surface of each of the plates. Pilot holes can be drilled for each guide pin. Two or more guide pins can provide greater stabilization of the insertion process while pressing the vertebral plate fusion spikes into cancellous bone. Multiple guide pins per surface can also be used to orient the device axially, should a particular embodiment restrict some motions more than others, i.e., change from isotropic to anisotropic degrees of freedom of motion, for clinical or other reasons. A person with skill in the art would be able to determine the appropriate number and placement of guide pins and/or similar structures with the same intended purpose. It is contemplated that such variations fall within the scope of the subject invention.

Advantageously, the embodiments of the subject application or variations thereof can provide 1) effective static load bearing through one or more spring elements, 2) hydraulic damping and shock absorption by means of hydraulic pumping action, 3) cushioning in the various joint axes conjoined with a general-purpose cushion element, constrained within the device by a central cylindrical core, 4) automatic hydraulic lubrication of all joints, 5) intervertebral stability and inseparability through mechanical linkage between a superior and an inferior vertebral plate that prevents motion outside the nominal, natural range, 6) mechanically programmable vertebral spacing under nominal compression load-bearing by appropriate selection of spring constants, height and number in the central spring element or stack, 7) 6-DOF motion tracking with variable disc height throughout the prosthesis workspace, as dictated by nominal disc operation, and 8) a mechanically programmable prosthesis workspace through judicious sizing of linear, planar, and rotational joint stops. The axial translation allowed by the hydraulic cylinder can be independently specified, while rotation maximums about the sagittal, lateral and axial axes can be mechanically programmed for the multi-curvate ball-and-socket joint with the use of spherical sliders, enabling the invention to match its workspace to that of the client's FSU workspace.

A tough, but compressible, hydrophilic, elastomer cushioning device, or devices that function similar thereto, can replace significant portions or all of the spring elements in a particular embodiment. The cushioning element can have a central hole for the superior and inferior mandrel to center and hold it in place within the ball-cylinder cavity. The ball-cylinder cavity can protect and confine such cushioning material, making migration and wear on the cushioning element less problematic. Hydraulic portals in the walls of the ball-cylinder (FIG. 38 and FIG. 39) can allow the flow of fluids into and out of the cushioning material as it expands and compresses, respectively.

The motion elements of the prosthetic device of the subject invention can be fabricated of, for example, but not limited to, titanium steel, titanium-carbide-coated stainless steel, bio-inert hardened stainless steel, polyurethane, polyetheretherketone, cobalt-chromium-molybdenum alloy, high molecular density thermoplastics, ceramics, glass, or other materials or combinations thereof. In a further embodiment, the motion elements of the prosthetic device of the subject invention can be fabricated with hardened stainless steel ball-bearings or ball-bearings of high density molecular polymers such as polyurethane and polyetheretherketone that fit into raceway cavities of the various titanium, stainless steel, polyurethane thermoplastic, polyetheretherketone, or other high molecular density thermoplastic elements. In an alternative embodiment, various combinations of polyurethane, polyetheretherketone, high molecular density thermoplastic, titanium, ceramics, cobalt-chromium-molybdenum alloy and titanium-carbide-coated hardened stainless steel bearings and components can be utilized. A person with skill in the art having benefit of the subject disclosure would be able to determine any of a variety of materials that could be utilized for the manufacture of one or more elements of the device of the subject invention. It is contemplated that such variations are within the scope of the subject invention. In this context, refer, for further instruction on the use of rod and ball bearings in lieu of lower kinematic pairs, taught by Doty in U.S. Pat. Nos. 7,361,192, 7,799,080, and 7,927,375, as well as U.S. Patent application no. US2010/0324688A1 and Published PCT Application No, PCT/US2010/37721, which are incorporated herein by reference.

The device of the subject invention can also allow for joint limits and stops on all degrees of freedom, which permits mechanical programming of its workspace to match the FSU workspace. The invention can, thus, accommodate the wide variability of FSU workspace motion at different locations within a spine and between the spines of different patients.

In a further embodiment, the spinal disc prosthesis of the subject invention comprises a flexible, multi-layered-boot-protected, modular and replaceable 6-DOF prosthetic disc mechanism (mechanical kinematic linkage). In one embodiment, the vertebral plates can be formed from a biocompatible material such as, for example, titanium, cobalt-chromium-molybdenum alloy, or titanium-carbide-coated stainless steel with a bone fusion matrix on a curvate surface to enhance surface area contact between vertebra and the vertebral plates. This configuration can help the fusion spikes to further anchor the invention into the vertebrae of an FSU.

Any number of techniques, as well as the ones specified herein, known to those with skill in the art may be used to embed the superior vertebral plate of the subject invention into the bone of the superior vertebra and the inferior vertebral plate into the bone of the inferior vertebra of an FSU. It is contemplated that such techniques are within the scope of the subject invention.

In a further embodiment, a flexible, multi-layered boot 12-1 (12-2) as shown, for example, in FIG. 2 (FIG. 24), surrounds the prosthetic device of the subject invention. The boot can provide a biocompatible impermeable barrier between fluids that may be sealed within the prosthetic device, for example, a biocompatible silicone fluid or saline solution, or other suitable fluid, and fluids within surrounding tissues. In one embodiment, the boot is a sturdy, flexible and elastic material, such as, for example, corrugated materials, woven fiber materials, and elastic materials, or other non-homogeneous materials or combinations thereof. In a preferred embodiment, the boot comprises woven, flexible fibers embedded in a strong, flexible silicon elastomer matrix that can block fluid transfer. The embedded fiber weave, in the embodiment mentioned above, can assist in torsion loading on the prosthesis, as well as loading during flexion and extension. In a further embodiment, the weave direction of the embedded fibers is diagonal relative to the central axis of a spherical or right-circular cylinder embodiment of the boot structure. In an alternative embodiment, the boot can be quilted, with quilt pads filled with cushioning materials or different types of fluids. In a particular embodiment, a corrugated boot, manufactured from a rugged fiber elastomer designed for flexibility and toughness, assists in torsion loading on all axes and opposes extension under nominal conditions, thus, reducing nominal spinal muscle stress in the neutral position. In a further embodiment, a variety of joint limit stops can be utilized on the multi-curvate ball-and-socket rotational joint of the invention, which can act to limit the amount of torsion the boot experiences, reducing the possibility of tears from overstress.

All displacements and rotations of the joints of the subject invention can be mechanically programmed to specific joint limits by appropriately installed joint stops. The joint stops can be rigid, or, to reduce wear, cushioned with materials falling within a wide range of durometer choices from between approximately 50 to approximately 100.

In one embodiment, the boot has asymmetric thickness, using more reinforcing fiber in the posteriorly-installed portion and less in the anteriorly-installed portion, making the anterior portion more flexible and the posterior portion less flexible, but stronger and more durable. The non-uniformity of the boot thickness allows for non-linear compression and extension. This configuration can reduce interaction with the spinal column vertebrae or surrounding nerves or ganglia when the boot is expanding and/or contracting. For example, as the FSU flexes, the boot can contract, primarily the highly flexible thinner sections. In a neutral position of the FSU, the boot can be under slight tension. At maximum compression of the FSU, the boot can bulge from hydraulic pressure and expanding cushioning material inside the device; however, without those pressures the boot would be slack. At maximum extension, the boot stretches, from its neutral position. In one embodiment, at maximum extension, the boot stretches an additional approximately 20% in its anterior portion and approximately 10% or less in the posterior portion.

In a further embodiment, a lubricating fluid is contained within the prosthetic device of the subject invention by the impermeable boot seal. In a still further embodiment, the lubricating fluid can be pumped through fluid hydraulic portals (mentioned above), or otherwise moved around and/or through the elements of the device, by the piston action of the superior and inferior hydraulic cylinders during spinal motion. These cylinders can further contain spring element 3-1 and cushioning elements (not shown) to provide a spring-dashpot action during FSU workspace motion.

Figure 1:
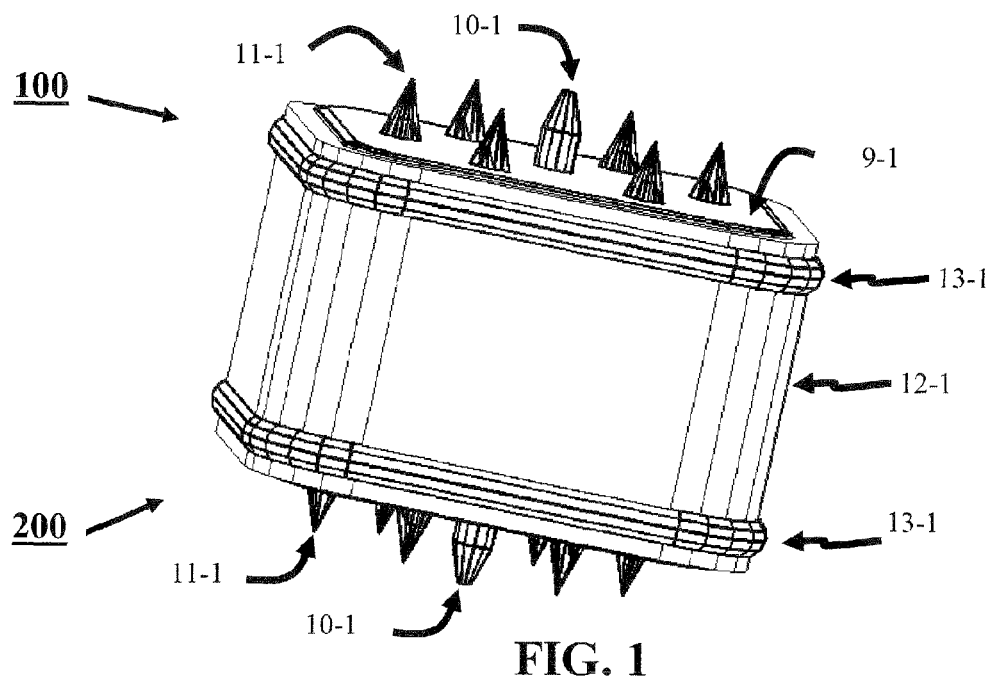
FIG. 1 depicts a rounded-corners square embodiment of an assembled disc prosthesis of the subject invention from a slightly tilted, perspective view. Visible elements of this embodiment include: the superior vertebral plate 9-1; the fiber-reinforced, flexible, multi-layered resilient boot 12-1; clamping rings 13-1; and cancellous bone fusion spikes 11-1. In this view, the boot hides the inferior vertebral plate 1-1.

Rectangular cross-section boot 12-1 (cylindrical boot 12-2), held by retaining elements 13-1 (13-2), as shown, for example, in FIG. 1, or retained by other techniques known to those skilled in the art, such as, but not limited to, compression fittings, screws, rivets, and/or pins through reinforced grommets in the boot, etc., can accommodate the shape of plate 9-1 (9-2) and 1-1 (1-2).

In an alternative embodiment, flat, ribbon-like, artificial ligaments 12-1-5 can be integrated into the boot 12-1 or attached externally to the four side surfaces of the subject invention, as shown, for example in FIG. 37; or to bilateral sides, left and right lateral or anterior and posterior; or to just a single lateral surface, for example the posterior one. In particular embodiments, opposing-pair artificial ligaments 12-1-5 can be preferred for mechanical reasons. The artificial ligaments can realize different torsion, tension, and flexibility parameters, not only in an anisotropic manner within a ligament segment, but also between segments. For example, the anterior ligament can be more flexible than the posterior ligament and the lateral ligaments can be stiffer than either.

A variation, considered to be within the scope of this invention, is to mount artificial ligaments 12-1-5 and then enclose the device within a flexible boot version of 12-1, or, alternatively, installs the flexible boot and mounts the ligament strips outside of the boot.

The same construction, i.e. one using a combination of multiple ligament strips between the superior and inferior vertebral plates covered by, or overlapping, or integrated into, a fluid/gas sealing, external boot, can be applied to cylindrical and other curvate structures of the vertebral plates (FIG. 23 and FIG. 24) and are not limited to the particular embodiments disclosed or shown here. The ligaments can be in slight tension equilibrium with the spring and cranial load when the FSU is in the neutral position. Such embodiments can permit separation of the functions of fluid containment by the boot and from the ligament function of binding with strength and flexibility, a binding that can resist torsion and extension of the invention to loads and generate restoring forces to drive the FSU towards its neutral position, in conjunction with the spring and cushion elements, when spinal muscles relax. For example, a left lateral tilt of the FSU will cause a left lateral ligament to relax and a right lateral ligament to extend and oppose the motion, an action that tends to restore the device to its original state once the spinal muscles relax. Such an embodiment offers the advantages of both techniques (boot and ligament), namely, a boot that seals the mechanism from bio-fouling and retains lubricating or dashpot fluids while the ligament structures provide strength to the joint and restoring forces to torsion and extension.

The comments of the previous paragraph can also apply to other cross sectional geometries of the vertebral plates, boot and ligaments, with little change and is considered within the scope of this invention. For example, a boot for fluid containment and exclusion can be attached to a cylindrically shaped unit (FIG. 23) over two or more strip ligaments, possibly with various widths, placed around the periphery of the circular vertebral plates and attached by the various means mentioned.

The low level pair joints of the subject invention can also be replaced by a variety of higher kinematic pairs by utilizing ball, rod, cylindrical and other types of bearings, known to those with skill in the art. For example, one can incorporate multiple ball-bearings partially embedded into the superior planar surface 8-1-1 of the socket or, alternatively, 9-1-1 of the superior vertebral plate, to reduce friction forces on the planar joint motion. Wall ball bearings judiciously placed, for example, in a segmented-ring raceway near the top and ball-bearings in a segmented-ring raceway near the center of the segmented-cylindrical cavity walls 1-1-2 can reduce friction in the prismatic joint between the ball-cylinder and the inferior vertebral plate. In one embodiment, such bearings can be such that tabs 5-1-1 do not touch the sides of cavities 1-1-3 and, hence, can offer no resistance to the action of the ball-cylinder-inferior-vertebral-plate prismatic joint, except to act as joint stops when they interfere with ball-cylinder retainer 6-1 (6-2).

The spherical surface 8-1-2 (8-6-2) of the socket 8-1 (8-6) and/or the spherical surfaces 5-1-2, 5-2-2, 5-5-2 (5-6-2) can also support ball-bearings arranged about the spherical surfaces to facilitate smoother operation of the ball-and-socket joint. A person with skill in the art, having benefit of the subject disclosure, would be able to determine any of a variety of alternative bearing structures and/or placements useful for the embodiments disclosed herein. In addition, Doty teaches in U.S. Pat. Nos. 7,361,192, 7,799,080, and 7,927,375, as well as U.S. Patent application no. US2010/0324688A1 and Published PCT Application No, PCT/US2010/37721, the use of bearings to reduce friction between surfaces in similar devices. It is contemplated that one skilled in the art can effect these different modifications without too much difficulty and such modifications are considered to be within the scope of this invention.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

It should also be understood that any reference in this specification to "one embodiment," "an embodiment," "example embodiment," "further embodiment," "alternative embodiment," etc., is for literary convenience. The implication is that any particular feature, structure, or characteristic described in connection with such an embodiment is included in at least one embodiment of the invention. The appearance of such phrases in various places in the specification does not necessarily refer to the same embodiment. Further, when a particular feature, structure, or characteristic is described in connection with any embodiment, it is submitted that it is within the purview of one skilled in the art to affect such feature, structure, or characteristic in connection with other ones of the embodiments.

I claim:

1. A device for providing at least one and up to three rotational degrees of freedom and at east one and up to three linear degrees of freedom comprising:
   a prismatic pair, with a cranial end and a caudal end, having,
      an inferior plate wherein the cranial end forms an upper wall surface and wherein a cavity is fainted within the inferior plate with one or more tab cavities peripheral to and contiguous with the cavity, such that the cavity and the one or more tab cavities are open at the cranial end;
      a ball-cylinder having a ball-cylinder wall, wherein one or more tabs are fixedly attached at or about the periphery of the caudal end of the ball-cylinder wall and the cranial end comprises a ball portion with a spherical cavity formed therein, which opens to the cranial end, such that the caudal end of the ball-cylinder wall and the one or more tabs can be inserted into and slide within the cavity and the one or more tab cavities, respectively, within the inferior plate;
      a ball-cylinder retainer with an opening there through that can be placed over the cranial end of the ball-cylinder, such that the ball portion extends through the opening, and the ball-cylinder retainer can be fixedly attached to the upper wall surface and cover the tab cavities, so that the tabs are retained within the tab cavities and the ball-cylinder is prevented from disconnecting from the inferior plate;
   a spherical slider having a cranial end and a caudal end and at least one lateral curvate surface, wherein the caudal end is moveably retained within the spherical cavity such that the cranial end of the spherical slider extends through the spherical cavity opening;
   a socket having a cranial end and a caudal end with a curvate raceway cavity there between, wherein the cranial end has a superior planar surface and the caudal end has a concave inferior surface having a curvature that is compatible with and movable on the ball portion of the ball-cylinder; and
   a socket cavity formed within the socket with an opening onto the concave inferior surface at the caudal end, such that the cranial end of the spherical slider can be moveably retained within the socket cavity,
   so that the device when assembled forms a kinematic chain characterized by inseparably connected, articulating components.
2. The device, according to claim 1, further comprising a superior plate having a cranial end and a caudal end, wherein the caudal end comprises
   a superior plate cavity with a planar surface, and
   a socket-retainer bearing;
   such that the cranial end of the socket can be positioned within the superior plate cavity, and moveably retained therein by the socket retainer bearing, which interacts with the curvate raceway of the socket, so that the planar surface can interact with the superior planar surface of the socket, and the superior plate forms part of the kinematic chain.
3. The device, according to claim 2, further comprising one or more cushioning elements between the ball cylinder and the inferior plate.
4. The device, according to claim 3, further comprising one or more artificial ligaments fixedly engaged with the superior plate and the inferior plate.
5. The device, according to claim 4, wherein the one or more artificial ligaments are in tension equilibrium with the cushioning elements.
6. The device, according to claim 3, further comprising a boot fixedly engaged with the superior plate and the inferior plate.
7. The device, according to claim 6, wherein the articulating components are sealed within the boot thereby preventing fluids external to the device from contacting the articulating components.
8. The device, according to claim 7, wherein the boot is capable of providing torsional load bearing.
9. The device, according to claim 8, wherein the boot is capable of providing non-linear compression and extension.
10. The device, according to claim 9, wherein the boot comprises a strong, flexible, non-homogeneous, fiber-reinforced elastomer matrix.
11. The device, according to claim 2, further comprising at least one guide pin extending from the cranial end of the superior plate.
12. The device, according to claim 2, further comprising at least one mounting fusion spike extending from the cranial end of the superior plate.
13. The device, according to claim 12, further comprising at least one guide pin extending from the cranial end of the superior plate.
14. The device, according to claim 2, further comprising one or more bearings positioned between one or more of the articulating components.
15. The device, according to claim 1, wherein the ball-cylinder further comprises a ball cylinder cavity that opens onto the caudal end of the ball-cylinder.
16. The device, according to claim 15, further comprising at least one superior mandrel mounted within the ball-cylinder cavity.
17. The device, according to claim 16, further comprising an inferior mandrel mounted within the cavity of the vertebral plate that can be operably connected to the superior mandrel within the hall-cylinder cavity.
18. The device, according to claim 17, further comprising one or more cushioning elements between the ball cylinder and the inferior plate.
19. The device, according to claim 18, wherein the one or more cushioning elements comprise two or more Belleville springs positioned within the ball cylinder cavity.
20. The device, according to claim 19, further comprising a platform affixed to the caudal end of the inferior plate cavity.
21. The device, according to claim 20, wherein the one or more cushioning elements rest on the platform.
22. The device, according to claim 1, further comprising at least one guide pin extending from the caudal surface of the inferior plate.

23. The device, according to claim 22, further comprising at least one mounting fusion spike extending from the caudal surface of the inferior plate.

24. The device, according to claim 1, further comprising at least one mounting fusion spike extending from the caudal surface of the inferior plate.

25. The device, according to claim 1, further comprising a spherical sliding surface on the cranial end of the spherical slider and a caudal sliding surface within the socket cavity which is compatible with the spherical sliding surface, such that the two surfaces can slide against each other.

26. The device, according to claim 25, wherein the spherical sliding surface on the cranial end of the spherical slider is curved and wherein the socket cavity further comprises a caudal sliding surface that is also curved, such that the two curvatures are compatible and the two surfaces can slide against each other.

27. The device, according to claim 25, further comprising a spherical sliding surface on the caudal end of the spherical slider, which is compatible with a cranial sliding surface within the ball-cylinder cavity, such that the two surfaces can slide against each other.

28. The device, according to claim 27, wherein the spherical sliding surface on the caudal end of the spherical slider is curved and wherein the cranial sliding surface within the ball-cylinder cavity is also curved, such that the two curvatures are compatible and the two surfaces can slide against each other.

29. The device, according to claim 28, wherein one or both of the spherical sliding surfaces comprise boundaries that are circular.

30. The device, according to claim 28, wherein one or both of the spherical sliding surfaces comprises boundaries that are a planar closed curve shape, which includes elliptical, circular, squared, rectangular, triangular, or other polygonal shape.

31. The device, according to claim 27, wherein one of the at least one lateral curvate surface on the spherical slider is a stem lateral curvate surface.

32. The device, according to claim 31, further comprising a cranial edge surface around the opening of the ball-cylinder spherical cavity and a caudal edge surface around the opening of the socket cavity.

33. The device, according to claim 32, wherein the stem lateral curvate surface comprises a shape that is operably compatible with the cranial edge surface and the caudal edge surface, such that the position of the spherical slider is maintained with minimal tolerance providing minimal or no separation between the socket and the ball cylinder.

34. The device, according to claim 33, wherein the stem lateral curvate surface is spherical and the edge surfaces have a concave curvature compatible with the spherical stem lateral surface.

35. The device, according to claim 34, wherein the cranial end of the spherical slider further comprises at least one additional spherical sliding surface and the socket cavity further comprises a socket cavity inferior spherical surface, wherein the at least one additional spherical sliding surface can operably contact and slide against the socket cavity inferior spherical surface.

36. The device, according to claim 35, wherein the caudal end of the spherical slider further comprises at least one additional spherical sliding surface and the spherical cavity further comprises a spherical cavity superior spherical surface, wherein the at least one additional spherical sliding surface can operably contact and slide against the spherical cavity superior spherical surface.

37. The device, according to claim 1, further comprising one or more hydraulic portals.

38. The device, according to claim 1, wherein the circumferential shape of the device is a rounded-corners square.

39. The device, according to claim 1, wherein the circumferential shape of the device is circular.

40. A device for providing at least one and up to three rotational degrees of freedom and at least one and up to three linear degrees of freedom comprising:
a prismatic pair, with a cranial end and a caudal end, having,
an inferior plate wherein the cranial end forms an upper wall surface and wherein a cavity is formed within the inferior plate with one or more tab cavities peripheral to and contiguous with the cavity, such that the cavity and the one or more tab cavities are open at the cranial end;
a ball-cylinder having a ball-cylinder wall, wherein one or more tabs are fixedly attached at or about the periphery of the caudal end of the ball-cylinder wall and the cranial end comprises a ball portion, such that the caudal end of the ball-cylinder wall and the one or more tabs can be inserted into and slide within the cavity and the one or more tab cavities, respectively, within the inferior plate;
a ball-cylinder retainer with an opening there through that can be placed over the cranial end of the ball-cylinder, such that the ball portion extends through the opening, and the ball-cylinder retainer can be fixedly attached to the upper wall surface and cover the tab cavities, so that the tabs are retained within the tab cavities and the ball-cylinder is prevented from disconnecting from the inferior plate;
a spherical slider having a cranial end and a caudal end, where the cranial end has at least one lateral curvate surface and the caudal end is anchored at or about the center of the ball portion of the ball-cylinder, such that the cranial end of the spherical slider extends generally perpendicular from the ball portion;
a socket having a cranial end and a caudal end with a curvate raceway cavity there between, wherein the cranial end has a superior planar surface and the caudal end has a concave inferior surface having a curvature that is compatible with and movable on the ball portion of the ball-cylinder; and
a socket cavity formed within the socket with an opening onto the concave inferior surface at the caudal end, such that the cranial end of the spherical slider can be moveably retained within the socket cavity,
so that the device when assembled forms a kinematic chain characterized by inseparably connected, articulating components.

41. The device, according to claim 40, further comprising a superior plate having a cranial end and a caudal end, wherein the caudal end comprises
a superior plate cavity with a planar surface, and
a socket-retainer bearing;
such that the cranial end of the socket can be positioned within the superior plate cavity, and moveably retained therein by the socket retainer bearing, which interacts with the curvate raceway of the socket, so that the planar surface can interact with the superior surface of the socket, and the superior plate forms part of the kinematic chain.

42. A device for providing at least one and up to three rotational degrees of freedom and at least one and up to three linear degrees of freedom comprising:

a prismatic pair, with a cranial end and a caudal end, having,
- an inferior plate wherein the cranial end forms an upper wall surface and wherein a cavity is formed within the inferior plate with one or more tab cavities peripheral to and contiguous with the cavity, such that the cavity and the one or more tab cavities are open at the cranial end;
- a ball-cylinder having a ball-cylinder wall, wherein one or more tabs are fixedly attached at or about the periphery of the caudal end of the ball-cylinder wall and the cranial end comprises a ball portion with at least two spherical cavities formed therein, which open to the cranial end, such that the caudal end of the ball-cylinder wall and the one or more tabs can be inserted into and slide within the cavity and the one or more tab cavities, respectively, within the inferior plate;
- a ball-cylinder retainer with an opening there through that can be placed over the cranial end of the ball-cylinder, such that the ball portion extends through the opening, and the ball-cylinder retainer can be fixedly attached to the upper wall surface and cover the tab cavities, so that the tabs are retained within the tab cavities and the ball-cylinder is prevented from disconnecting from the inferior plate;
- a socket having a cranial end and a caudal end with a curvate raceway cavity there between, wherein the cranial end has a superior planar surface and the caudal end has a concave inferior surface whose curvature is compatible with and movable on the ball portion of the ball-cylinder and at least two spherical sliders anchored thereto, where the at least two spherical sliders each have at least one lateral curvate surface and each have a cranial end and a caudal end, wherein the cranial ends are anchored to the caudal end of the socket, so that the caudal ends of the spherical sliders extend from the caudal end of the socket and are retained within the at least two spherical cavities within the ball-cylinder,
so that the device when assembled forms a kinematic chain characterized by inseparably connected, articulating components.

* * * * *

UNITED STATES PATENT AND TRADEMARK OFFICE
CERTIFICATE OF CORRECTION

PATENT NO. : 8,277,505 B1
APPLICATION NO. : 13/157539
DATED : October 2, 2012
INVENTOR(S) : Keith L. Doty Page 1 of 2

It is certified that error appears in the above-identified patent and that said Letters Patent is hereby corrected as shown below:

Title page, Item [57], Abstract,
Line 7, "In embodiment" should read --In one embodiment--.
Line 9, "links to spherical pair" should read --links to a spherical pair--.

Column 11,
Line 38, "stern, and cavity" should read --stem, and cavity--.

Column 12,
Line 59, "such modification are" should read --such modifications are--.

Column 13,
Line 36, "hall-bearing ring" should read --ball bearing ring--.

Column 18,
Line 27, "$2^{ndd}$ Addition" should read --$2^{nd}$ Edition--.

Column 19,
Line 11, "below the heads" should read --below the beads--.

Column 38,
Line 8, "hall-and-socket" should read --ball-and-socket--.

Column 39,
Line 40, "hall-cylinder 5-1 (5-2)" should read --ball-cylinder 5-1 (5-2)--.

Column 41,
Lines 38-39, "stainless steal, titanium, titanium coated stainless steal" should read
--stainless steel, titanium, titanium coated stainless steel--.

Signed and Sealed this
Twenty-seventh Day of November, 2012

David J. Kappos
*Director of the United States Patent and Trademark Office*

Column 42,
Line 16, "6 min" should read --6 mm--.

Column 44,
Line 41, "socket hearing raceway" should read --socket bearing raceway--.

Column 46,
Line 3, "hall-cylinder" should read --ball-cylinder--.

Column 51,
Line 23, ""fainted within" should read --formed within--.

Column 52,
Line 54, "hall-cylinder cavity" should read --ball-cylinder cavity--.